United States Patent
Cooke et al.

(10) Patent No.: US 9,108,939 B2
(45) Date of Patent: Aug. 18, 2015

(54) (1, 1, 1,3,3,3-HEXAFLUORO-2 HYDROXYPROPAN-2-YL) PHENYL DERIVATIVE, PHARMACEUTICAL COMPOSITIONS THEREOF AND THEIR USE FOR THE TREATMENT OF ATHEROSCLEROSIS

(75) Inventors: Andrew John Cooke, West Point, PA (US); Emma Louise Carswell, Cambridge (GB); David Jonathan Bennett, West Point, PA (US)

(73) Assignee: Merck Sharp & Dohme B.V., Haarlem (NL)

( * ) Notice: Subject to any disclaimer, the term of this patent is extended or adjusted under 35 U.S.C. 154(b) by 288 days.

(21) Appl. No.: 13/504,209

(22) PCT Filed: Oct. 26, 2010

(86) PCT No.: PCT/EP2010/066157
§ 371 (c)(1),
(2), (4) Date: May 25, 2012

(87) PCT Pub. No.: WO2011/051282
PCT Pub. Date: May 5, 2011

(65) Prior Publication Data
US 2012/0238574 A1    Sep. 20, 2012

Related U.S. Application Data

(60) Provisional application No. 61/255,312, filed on Oct. 27, 2009.

(30) Foreign Application Priority Data

Oct. 27, 2009 (EP) .................................... 09174106

(51) Int. Cl.
| | | |
|---|---|---|
| *A61K 31/445* | (2006.01) | |
| *C07D 211/28* | (2006.01) | |
| *C07D 295/135* | (2006.01) | |
| *C07D 213/75* | (2006.01) | |
| *C07D 237/20* | (2006.01) | |
| *C07D 239/42* | (2006.01) | |
| *C07D 261/12* | (2006.01) | |
| *C07D 295/096* | (2006.01) | |
| *C07D 295/192* | (2006.01) | |

(52) U.S. Cl.
CPC .......... *C07D 295/135* (2013.01); *C07D 211/28* (2013.01); *C07D 213/75* (2013.01); *C07D 237/20* (2013.01); *C07D 239/42* (2013.01); *C07D 261/12* (2013.01); *C07D 295/096* (2013.01); *C07D 295/192* (2013.01)

(58) Field of Classification Search
CPC .. C07D 211/28; C07D 213/75; C07D 237/20; C07D 239/42; C07D 261/12; C07D 295/96; C07D 295/135; C07D 295/192
USPC ......... 514/235.5, 252.03, 256, 275, 316, 318, 514/322, 326, 327; 544/130, 238, 329, 332; 546/188, 194, 199, 207, 209, 213, 214, 546/221
See application file for complete search history.

(56) References Cited

U.S. PATENT DOCUMENTS 8,357,679 B2 *    1/2013    Cooke et al. .................. 514/218

FOREIGN PATENT DOCUMENTS

| WO | WO 00/54759 A2 | 9/2000 |
|---|---|---|
| WO | WO 2004/048334 A1 | 6/2004 |
| WO | WO 2006/037480 A1 | 4/2006 |
| WO | WO 2009/138438 | 11/2009 |

OTHER PUBLICATIONS

Ahmad et al. "Synthesiss, docking . . . " J. Pharm Sci. vol. 21(47) p. 1-9, (2013).*
Lima et al. "Bioisosterism . . . " Curr. Med. Chem. v.12, p. 23-49 (2005).*
Thornber :Isosterism . . . Chem. Soc Rev. vol. 8, p. 563-580 (1979).*
Wolin et al. "Inhibitors of . . . " Bioorg. Med. Chem. Lett. vo. 8, p. 2521-2526 (1998).*
Lead Compound, Fed. Reg. p. 1-34 Sep. 1, 2010.*
International Search Report for: PCT/EP2010/066157; By Authorized officer: Jacques Rufet; Performed at European Patent Office; Date completed: Feb. 23, 2011.

* cited by examiner

*Primary Examiner* — Celia Chang
(74) *Attorney, Agent, or Firm* — Patricia A. Shatynski; Catherine D. Fitch

(57) ABSTRACT

The present invention relates to (1,1,1,3,3,3-hexafluoro-2-hydroxypropan-2-yl)phenyl derivatives having the general formula (I) to pharmaceutical compositions comprising the same and to the use of these (1,1,1,3,3,3-hexafluoro-2-hydroxy-propan-2-yl)phenyl derivatives in the treatment of atherosclerosis.

(I)

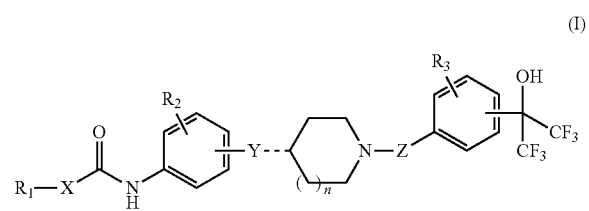

7 Claims, No Drawings

(1, 1, 1,3,3,3-HEXAFLUORO-2 HYDROXYPROPAN-2-YL) PHENYL DERIVATIVE, PHARMACEUTICAL COMPOSITIONS THEREOF AND THEIR USE FOR THE TREATMENT OF ATHEROSCLEROSIS

The present invention relates to (1,1,1,3,3,3-hexafluoro-2-hydroxypropan-2-yl)phenyl derivatives, to pharmaceutical compositions comprising the same and to the use of these (1,1,1,3,3,3-hexafluoro-2-hydroxypropan-2-yl)phenyl derivatives in the treatment of atherosclerosis.

The Liver X Receptors (LXRs) are a family o f nuclear receptors that are activated upon binding of the naturally occurring oxysterols inducing transcription of target genes. Two subtypes of LXR (α and β) have been identified and exhibit 77% homology at both their ligand- and DNA-binding domains. Both subtypes are highly conserved between humans and rodents however their tissue expression patterns differ significantly. The expression of LXRα is restricted to tissues involved in lipid metabolism with highest expression in the liver; there are also significant levels in kidney, spleen, small intestine and adipose tissue. LXRβ is very widely distributed and has been found in virtually every tissue examined, including liver and brain. Both LXRα and LXRβ are expressed in macrophages. See Costet et al., *J. Biol. Chem.* 275:28240-28245 (2000).

The roles of the LXR receptors are not fully understood, however LXR is well established as a master regulator of lipid metabolism in the liver and peripheral tissues, and as the key inducer of the ATP-binding cassette transporter A1 (ABCA1) gene. See Venkateswaran et al., *Proc. Natl. Acad. Sci. USA.* 22:12097-12102 (2000). In the human population, mutations of the ABCA1 gene lead to highly atherogenic lipoprotein profiles (Singaraja et al., *Arterioscler. Thromb. Vasc. Biol.* 8: 1322-1332 (2003)) which in the most severe form cause Tangier's Disease and associated premature atherosclerosis, (see Bodzioch et al., *Nat. Genet.* 22:347-351 (1999) and Rust et al., *Nat. Genet.* 22:352-355 (1999)). This rare inherited disorder is characterised by very low levels of high density lipoproteins (HDL), macrophage accumulation of cholesterol esters and significantly increased risk of atherosclerotic disease.

Evidence has demonstrated that up-regulation of ABCA1 in human macrophages and enterocytes of the small intestine, is mediated by LXR activation. See Costet et al., *J. Biol. Chem.* 275:28240-28245 (2000). Furthermore, LXR agonists have also been shown to promote cholesterol efflux. See Claudel et al., *Proc. Natl. Acad. Sci. USA.* 98:2610-2615 (2001). LXR receptors therefore play a critical role in cholesterol homeostasis in macrophages, and suppression within the local environment of the advanced atherosclerotic plaque may be a key feature of the pathology of the disease.

The first compounds specifically identified as LXR agonists for the treatment of atherosclerosis were disclosed by Tularik, Inc. (International Patent Application WO 00/54759) and contain the hexafluoroisopropanol group. Since then a number of different chemotypes have been identified as LXR agonists (for a review see: Bennett et al. Expert Opin. Ther. Patents 16, 1673-1699, 2006).

There is a remaining need for compounds that are effective as LXR modulators.

To this aim the present invention provides (1,1,1,3,3,3-hexafluoro-2-hydroxypropan-2-yl)phenyl derivatives having the general Formula I

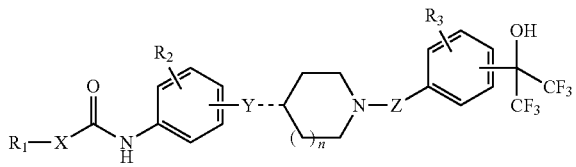

Formula I wherein
n is 0 or 1;
X is $NR_4$, O or bond;
Y is O, $CHR_5$, $C(OR_6)R_5$, CO, S, SO, $SO_2$, $NR_5$, $CONR_5$ or a bond, and the dotted bond represents a single bond; or
Y is $CR_5$, and the dotted bond represents a double bond;
Y has a meta or para substitution pattern on the phenyl ring in relation to the phenyl-NH position;
Z is $CH_2$ or CO;
the hexafluoroispopropanol substituent has an ortho, meta or para substitution pattern on the phenyl ring in relation to the phenyl-Z position;
$R_1$ is $(C_{1-8})$alkyl, $(C_{3-8})$cycloalkyl or $(C_{3-8})$cycloalkyl$(C_{1-4})$alkyl, each of the alkyl groups being optionally substituted by 1 or 2 substituents selected from hydroxy, hydroxylmethyl, $(C_{1-3})$alkyloxy, cyano, halogen, $CF_3$, $NR_7R_8$, $NR_7R_8CO$ and $R_9OCO$; or
$R_1$ is 5- or 6-membered aromatic ring, optionally comprising 1-3 heteroatoms selected from O, S and N, the ring being optionally substituted by $(C_{1-3})$alkyl, $(C_{3-6})$cycloalkyl, $(C_{1-3})$alkyloxy, $(C_{1-3})$alkylsulfonyl, cyano, $CF_3$, $OCF_3$, halogen or $R_9OCO$, and the ring being optionally linked to X via a $(C_{1-3})$alkylene group which is optionally substituted by hydroxy; or
$R_1$ is a 4-, 5- or 6-membered saturated or unsaturated heterocyclic ring, comprising 1 or 2 heteroatoms selected from $NR_{10}$, O, S, SO and $SO_2$, the ring being optionally substituted by $(C_{1-3})$alkyl, hydroxy, oxo, $NR_{11}R_{12}$ or $R_9OCO$, and the ring being optionally linked to X via a $(C_{1-3})$alkylene group which is optionally substituted by hydroxy; or
when X is $NR_4$, $R_1$ may together with $R_4$ and the N to which they are bonded form a 4-8 membered ring, which can be optionally substituted with hydroxy or hydroxymethyl;
$R_2$ is H or 1-3 halogens; or
when Y is $NR_5$, $R_2$ and $R_5$ may together with the 2 adjacent carbon atoms to which they are bonded form a fused 5-membered heteroaromatic ring, optionally comprising 1 or 2 additional N atoms;
$R_3$ is H or $(C_{1-3})$alkyl;
$R_4$, when present, is H or $(C_{1-3})$alkyl;
$R_5$, when present, is H or $(C_{1-3})$alkyl;
$R_6$, when present, is H or $(C_{1-3})$alkyl;
$R_7$ and $R_8$, when present, are independently H or $(C_{1-3})$alkyl;
$R_9$, when present, is H or $(C_{1-3})$alkyl;
$R_{10}$, when present, is H or $(C_{1-3})$alkyl;
$R_{11}$ and $R_{12}$, when present, are independently H or $(C_{1-3})$alkyl;
or a pharmaceutically acceptable salt thereof.

The term $(C_{1-8})$alkyl as used in the definition of Formula I means a branched or unbranched alkyl group having 1-8 carbon atoms, like octyl, hexyl, pentyl, isopentyl, butyl, isobutyl, tertiary butyl, propyl, isopropyl, ethyl and methyl.

The term $(C_{1-4})$alkyl as used in the definition of Formula I means a branched or unbranched alkyl group having 1-4 carbon atoms, like butyl, isobutyl, tertiary butyl, propyl, isopropyl, ethyl and methyl.

Likewise, the term $(C_{1-3})$alkyl used in the definition of Formula I means a branched or unbranched alkyl group having 1-3 carbon atoms, like propyl, isopropyl, ethyl and methyl.

The term $(C_{3-8})$cycloalkyl means a cycloalkyl group having 3-8 carbon atoms, like cycloheptyl, cyclohexyl, cyclopentyl, cyclobutyl and cyclopropyl.

In the term $(C_{3-8})$cycloalkyl($C_{(1-4)}$)alkyl, $(C_{3-8})$cycloalkyl and $(C_{1-4})$alkyl have the meaning as given above. In addition the term $(C_{3-8})$cycloalkyl($C_{(1-4)}$)alkyl encompasses compounds in which one of the cycloalkyl carbon atom is a spiro-carbon atom, such as 2-methyl-2-cyclopropylethyl and (1-methylcyclobutyl)methyl and the like.

The term $(C_{1-3})$alkylene means an alkanediyl functional group such as methylene, 1,2-ethanediyl, 1,3-propanediyl or 2-propanediyl.

The term 5- or 6-membered aromatic ring, optionally comprising 1-3 heteroatoms selected from O, S and N, as used in the definition of $R_1$ is exemplified by ring systems such as phenyl, pyridine-2-yl, pyridine-3-yl, pyridine-4-yl, pyrazin-2-yl, pyrimidin-4-yl, 1H-pyrazol-5-yl, pyridazin-4-yl, furan-2-yl, thien-2-yl, oxazol-3-yl, thiazol-2-yl, 1,3,4-thiaziazol-2-yl, 1,2,4-thiadiazol-5-yl, 1,2,4-oxadiazol-5-yl and the like.

The term 4-, 5- or 6-membered saturated or unsaturated heterocyclic ring, comprising 1 or 2 heteroatoms selected from $NR_{10}$, O, S, SO and $SO_2$, as used in the definition of $R_1$ is exemplified by tetrahydro-2H-pyran-4-yl, tetrahydro-2H-furan-2-yl, tetrahydrothiophen-3-yl, imidazolidin-1-yl, morpholin-1-yl, pyrrolidin-1-yl, piperidinyl, pyrrolidinyl, oxetan-3-yl, 1,2-dioxo-tetrahydro-$1\lambda^6$-thiophen-3-yl and the like.

The term halogen means F, Cl, Br or I.

There is a preference for (1,1,1,3,3,3-hexafluoro-2-hydroxypropan-2-yl)phenyl derivatives of Formula I wherein Z is $CH_2$.

Further preferred are the (1,1,1,3,3,3-hexafluoro-2-hydroxypropan-2-yl)phenyl derivatives of Formula I wherein Y is O or $CH_2$.

Also preferred are (1,1,1,3,3,3-hexafluoro-2-hydroxypropan-2-yl)phenyl derivatives of Formula I, wherein X is NH.

More preferred are the compounds of Formula I wherein $R_3$ is H and the hexafluoroisopopropanol substituent has the para substitution pattern on the phenyl ring in relation to the phenyl-Z position, and the compounds wherein $R_2$ represents H or 1 or 2 halogens selected from F and Cl.

Particular (1,1,1,3,3,3-hexafluoro-2-hydroxypropan-2-yl)phenyl derivatives of the invention are:

1-(4-(1-(4-(1,1,1,3,3,3-Hexafluoro-2-hydroxypropan-2-yl)benzyl)piperidin-4-yloxy)phenyl)-3-(tetrahydro-2H-pyran-4-yl)urea;

1-(4-(1-(4-(1,1,1,3,3,3-Hexafluoro-2-hydroxypropan-2-yl)benzyl)piperidin-4-yloxy)phenyl)-3-(2-hydroxy-2-methylpropyl)urea;

1-(4-(1-(4-(1,1,1,3,3,3-Hexafluoro-2-hydroxypropan-2-yl)benzyl)piperidin-4-yloxy)phenyl)-3-(pyridazin-4-yl)urea;

1-(4-(1-(4-(1,1,1,3,3,3-Hexafluoro-2-hydroxypropan-2-yl)benzyl)piperidin-4-yloxy)phenyl)-3-(pyridin-4-yl)urea;

1-(3-fluoropyridin-4-yl)-3-(4-(1-(4-(1,1,1,3,3,3-hexafluoro-2-hydroxypropan-2-yl)benzyl)piperidin-4-yloxy)phenyl) urea;

1-(4-(1-(4-(1,1,1,3,3,3-Hexafluoro-2-hydroxypropan-2-yl)benzyl)piperidin-4-yloxy)phenyl)-3-(pyrimidin-4-yl) urea;

1-(4-((1-(4-(1,1,1,3,3,3-Hexafluoro-2-hydroxypropan-2-yl)benzyl)piperidin-4-yl)methyl)phenyl)-3-(oxetan-3-yl) urea 1-(3-Fluoropyridin-4-yl)-3-(4-((1-(4-(1,1,1,3,3,3-hexafluoro-2-hydroxypropan-2-yl)benzyl)piperidin-4-yl) methyl)phenyl)urea;

1-(4-((1-(4-(1,1,1,3,3,3-Hexafluoro-2-hydroxypropan-2-yl)benzyl)piperidin-4-yl)methyl)phenyl)-3-(pyridin-4-yl) urea;

1-(4-((1-(4-(1,1,1,3,3,3-Hexafluoro-2-hydroxypropan-2-yl)benzyl)piperidin-4-yl)methyl)phenyl)-3-(pyrimidin-4-yl) urea;

1-(2-Fluoro-4-((1-(4-(1,1,1,3,3,3-hexafluoro-2-hydroxypropan-2-yl)benzyl)piperidin-4-yl)methyl)phenyl)-3-(isoxazol-4-yl)urea;

1-(2-Fluoro-4-((1-(4-(1,1,1,3,3,3-hexafluoro-2-hydroxypropan-2-yl)benzyl)piperidin-4-yl)methyl)phenyl)-3-(5-methylisoxazol-3-yl)urea;

(S)-1-(2-Fluoro-4-((1-(4-(1,1,1,3,3,3-hexafluoro-2-hydroxypropan-2-yl)benzyl)piperidin-4-yl)methyl)phenyl)-3-(tetrahydrofuran-3-yl)urea;

1-(2-Fluoro-4-((1-(4-(1,1,1,3,3,3-hexafluoro-2-hydroxypropan-2-yl)benzyl)piperidin-4-yl)methyl)phenyl)-3-(3,3,3-trifluoro-2-hydroxypropyl)urea;

1-(2-Fluoro-4-((1-(4-(1,1,1,3,3,3-hexafluoro-2-hydroxypropan-2-yl)benzyl)piperidin-4-yl)methyl)phenyl)-3-(3,3,3-trifluoro-2-hydroxy-2-methylpropyl)urea;

1-(2-Fluoro-4-((1-(4-(1,1,1,3,3,3-hexafluoro-2-hydroxypropan-2-yl)benzyl)piperidin-4-yl)methyl)phenyl)-3-(2-hydroxy-2-methylpropyl)urea;

1-(2-Fluoro-4-((1-(4-(1,1,1,3,3,3-hexafluoro-2-hydroxypropan-2-yl)benzyl)piperidin-4-yl)methyl)phenyl)-3-(oxetan-3-yl)urea;

1-(2-Fluoro-4-((1-(4-(1,1,1,3,3,3-hexafluoro-2-hydroxypropan-211)benzyl)piperidin-4-yl)methyl)phenyl)-3-(tetrahydro-2H-pyran-4-yl)urea;

1-(2-Fluoro-4-((1-(4-(1,1,1,3,3,3-hexafluoro-2-hydroxypropan-2-yl)benzyl)piperidin-4-yl)methyl)phenyl)-3-(pyridin-4-yl)urea;

1-(2-Fluoro-4-((1-(4-(1,1,1,3,3,3-hexafluoro-2-hydroxypropan-2-yl)benzyl)piperidin-4-yl)methyl)phenyl)-3-(pyrimidin-4-yl)urea;

1-(2,5-Difluoro-4-((1-(4-(1,1,1,3,3,3-hexafluoro-2-hydroxypropan-2-yl)benzyl)piperidin-4-yl)methyl)phenyl)-3-(2-hydroxy-2-methylpropyl)urea;

1-(2,5-Difluoro-4-((1-(4-(1,1,1,3,3,3-hexafluoro-2-hydroxypropan-2-yl)benzyl)piperidin-4-yl)methyl)phenyl)-3-(3,3,3-trifluoro-2-hydroxy-2-methylpropyl)urea; and 1-(2-Chloro-4-((1-(4-(1,1,1,3,3,3-hexafluoro-2-hydroxypropan-2-yl)benzyl)piperidin-4-yl)methyl)phenyl)-3-(2-hydroxy-2-methylpropyl)urea;

or a pharmaceutically acceptable salt thereof.

The (1,1,1,3,3,3-hexafluoro-2-hydroxypropan-2-yl)phenyl derivatives of the invention can be prepared using general synthetic methods known in the art of organic synthesis, for instance by using synthetic routes depicted in Schemes 1-9. Those skilled in the art will know that the order of addition of the key building blocks according to Formulas 2-47 can be altered and still give the desired products of Formula 1. Reaction schemes 1-8 represent generic methods for synthesising all the intermediates required to produce compounds of the invention according to Formula 1. The generic reaction scheme 9 provides the final synthetic steps required to convert the intermediates generated in reaction schemes 1-8 into compounds of the invention according to Formula 1.

Scheme 1

In this reaction scheme $R_3$ has the meaning as previously defined and L represents a leaving group e.g. $OSO_2Me$.

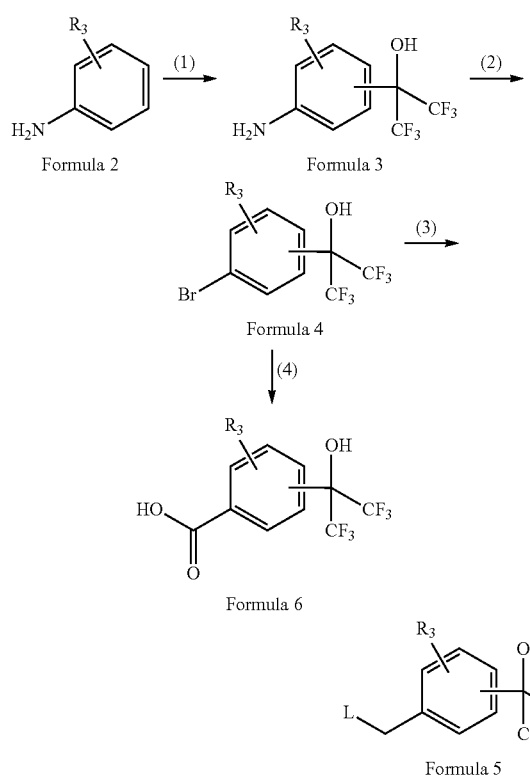

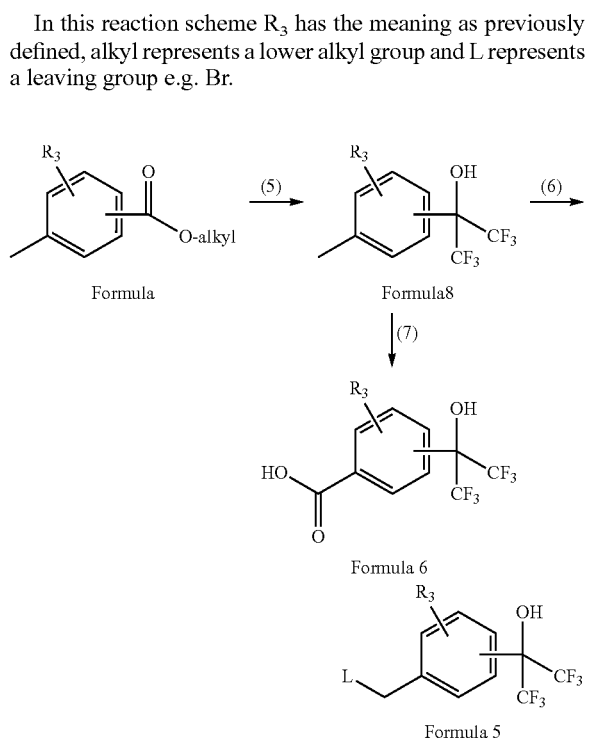

Scheme 2

In this reaction scheme $R_3$ has the meaning as previously defined, alkyl represents a lower alkyl group and L represents a leaving group e.g. Br.

Conditions: (1) hexafluoroacetone trihydrate, p-toluenesulfonic acid monohydrate, heat; (2) dioxane, water, hydrobromic acid (48% weight in water), sodium nitrite, copper (I) bromide; (3)(a) anhydrous tetrahydrofuran, −78° C., n-butyl lithium in hexane (2.5M), N,N-dimethylformamide; (b) sodium borohydride, methanol, dichloromethane; (c) When L is $OSO_2Me$: methanesulfonyl chloride, dichloromethane, triethylamine, 0° C.; (4) anhydrous tetrahydrofuran, −78° C., n-butyl lithium in hexane (2.5M), carbon dioxide.

Conditions: (5) cesium fluoride, (trifluoromethyl)trimethylsilane, N,N-dimethylformamide; (6) When L is Br: N-bromosuccinimide, 2,2'-azobis(isobutyronitrile), carbon tetrachloride, reflux; (7) potassium permanganate, water, elevated temperature.

Scheme 3 (when Y is CH and the Dotted Bond is a Single Bond; or Y is CH and the Dotted Bond is a Double Bond)

In this reaction scheme $R_2$ and n are as previously described.

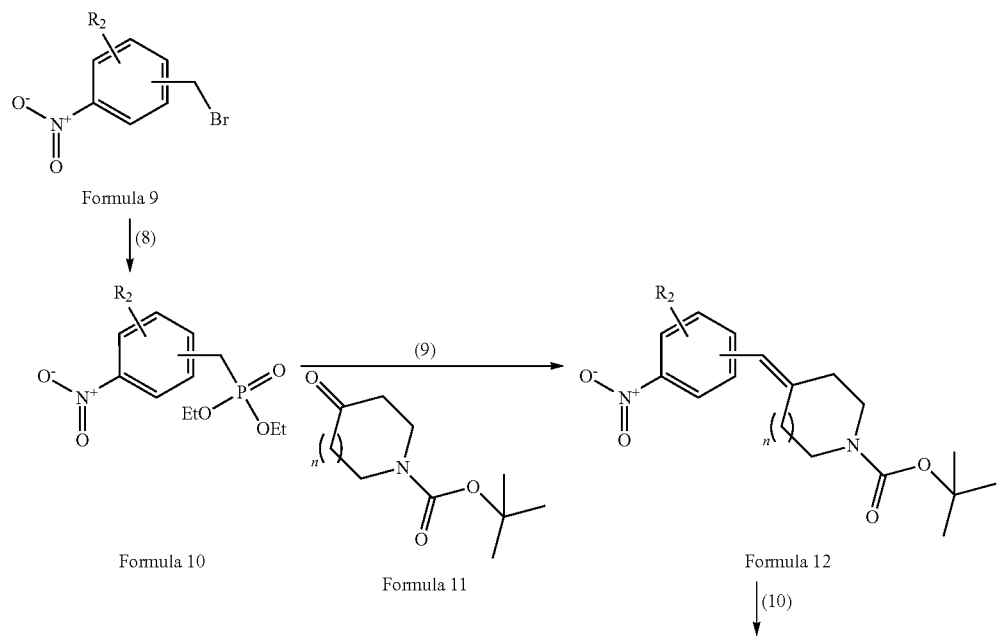

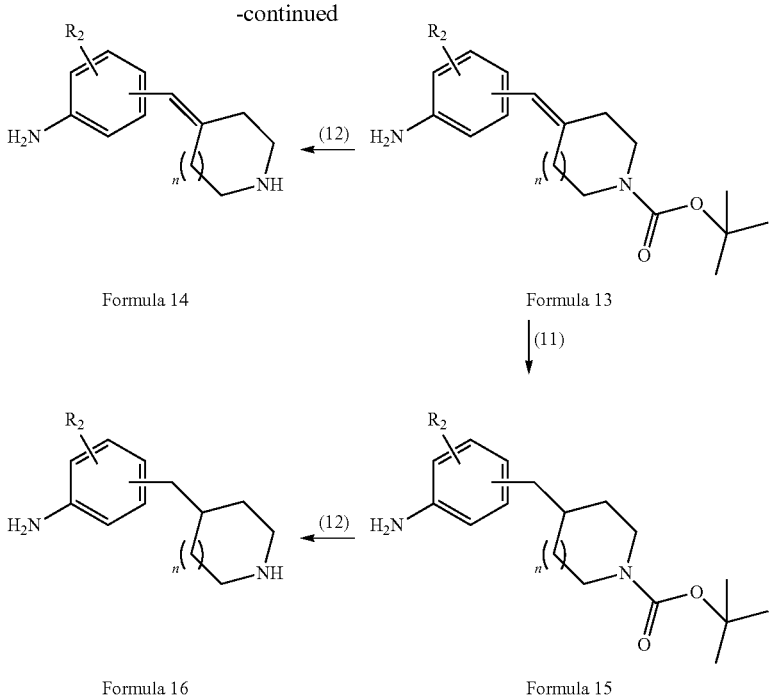

Formula 14      Formula 13

Formula 16      Formula 15

Conditions: (8) triethyl phosphate, 140° C.; (9) Formula 11, sodium hydride, tetrahydrofuran; (10) iron(II) sulfate heptahydrate, ammonia, ethanol, 85° C.; (11) platinum (IV) oxide, ethanol, hydrogen, 3 bar; or palladium on carbon, ethyl acetate, hydrogen, 3 bar; (12) trifluoroacetic acid, dichloromethane.

Scheme 4 (When Y is O, S or $NR_5$, Whereas $R_5$ is as Previously Described and the Dotted Bond is a Single Bond)

In this reaction scheme $R_2$ and n are as previously described.

Conditions: (13) potassium carbonate or sodium hydride, N,N-dimethylformamide or tetrahydrofuran, room or elevated temperature; (14) platinum (IV) oxide, ethanol, hydrogen, 3 bar; or palladium on carbon, ethyl acetate, hydrogen, 3 bar; (15) trifluoroacetic acid, dichloromethane.

Scheme 5 (When Y is $CONR_5$, Whereas $R_5$ is as Previously Described and the Dotted Bond is a Single Bond)

In this reaction scheme $R_2$ and n are as previously described.

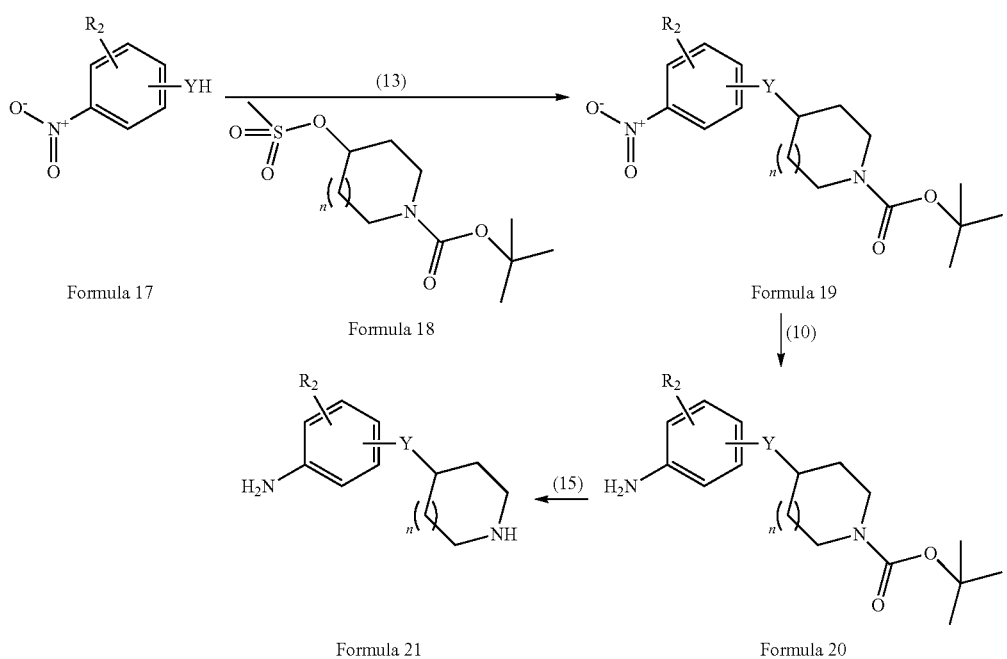

Formula 17      Formula 18      Formula 19

Formula 21      Formula 20

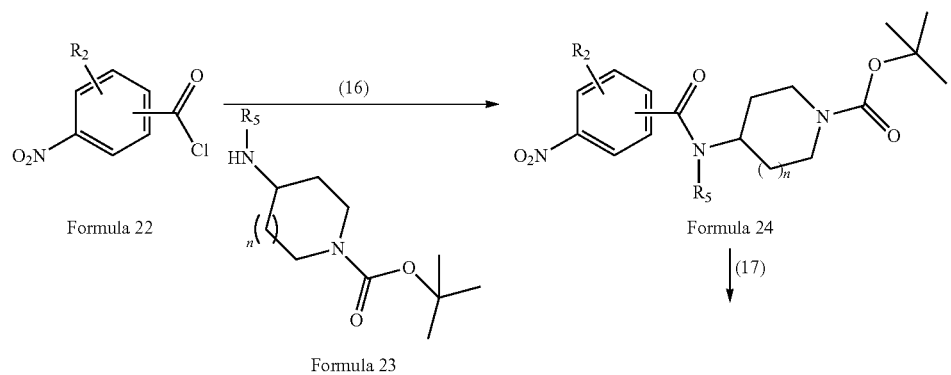
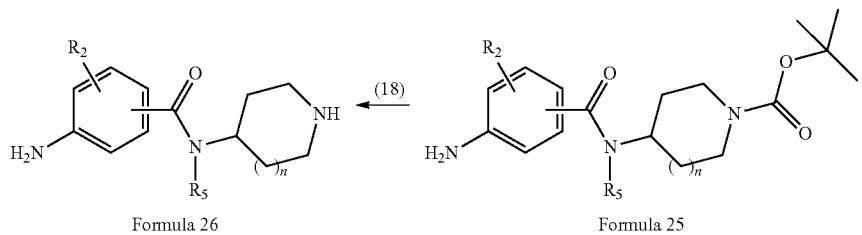
Conditions: (16) Formula 23, dichloromethane, triethylamine; (17) platinum (IV) oxide, ethanol, hydrogen, 3 bar; or palladium on carbon, ethyl acetate, hydrogen, 3 bar; (18) trifluoroacetic acid, dichloromethane.
Scheme 6 (When Y is SO or $SO_2$ and the Dotted Bond is a Single Bond)
In this reaction scheme $R_2$ and n are as previously described.
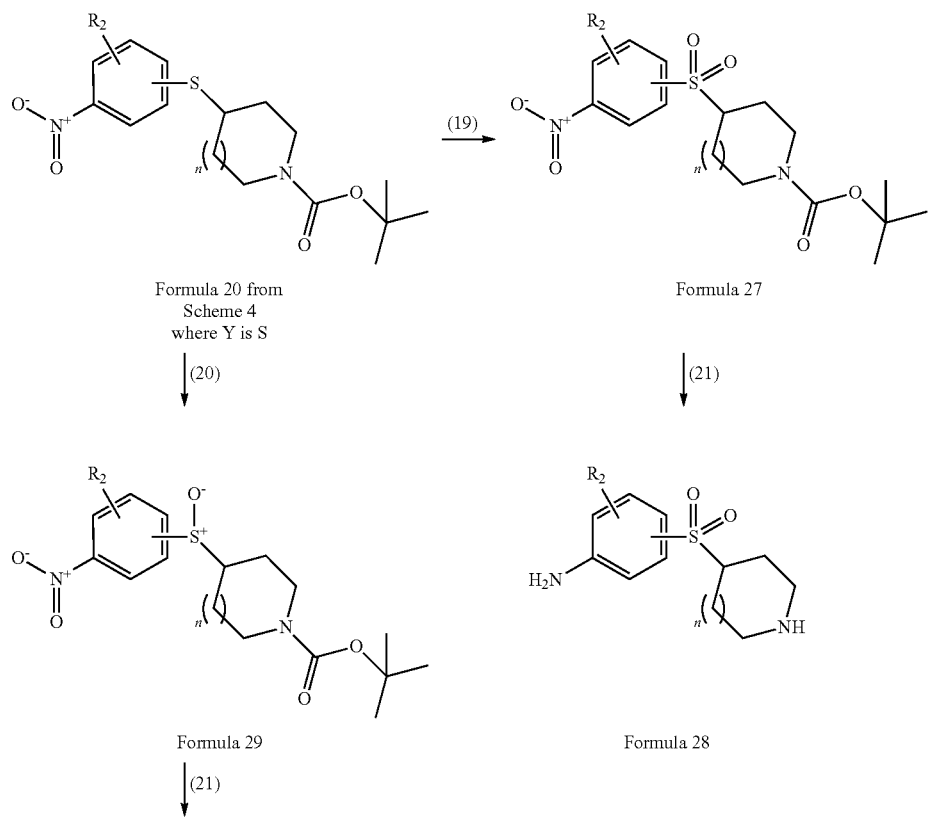

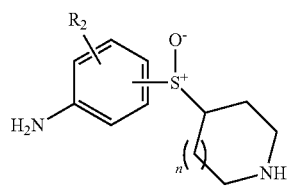

Formula 30

Conditions: (19) 3-chloroperoxybenzoic acid (2 eq.), dichloromethane; (20) 3-chloroperoxybenzoic acid (1 eq.), dichloromethane; (21) trifluoroacetic acid, dichloromethane.

Scheme 7 (When Y is CHR$_5$, C(OR$_5$)R$_6$ or CO and the Dotted Bond Represents a Single Bond; or Y is CR$_5$ and the Dotted Bond Represent a Double Bond; and R$_5$ and R$_6$ are as Previously Described)

In this reaction scheme R$_2$ and n are as previously described.

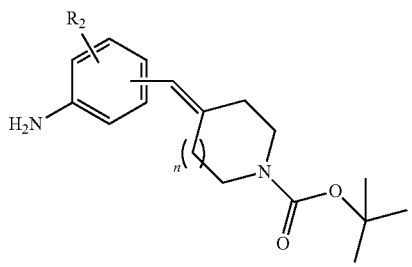

Formula 13
from Scheme 3

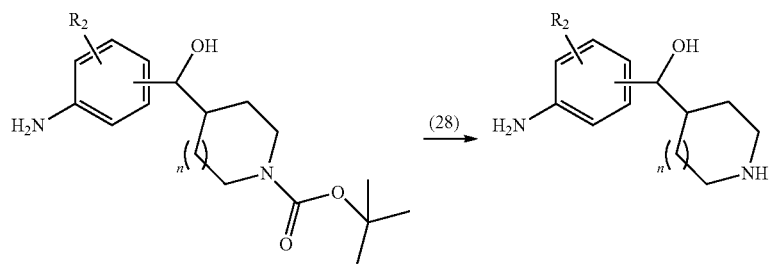

Formula 31      Formula 32

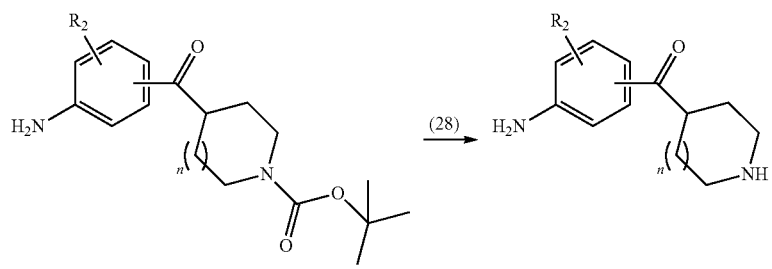

Formula 33      Formula 34

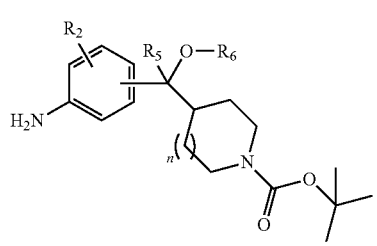

Formula 41

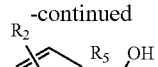

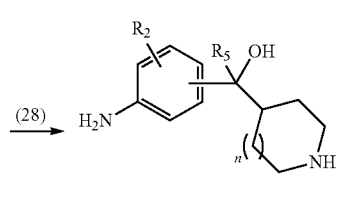

Formula 35

Formula 36

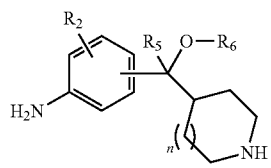

Formula 42

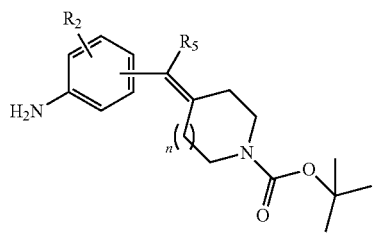

Formula 37

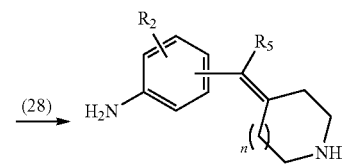

Formula 38

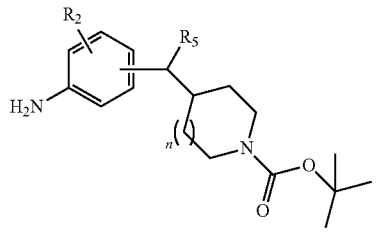

Formula 39

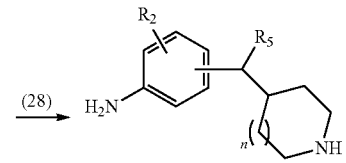

Formula 40

Conditions: (22) 1M diborane solution, tetrahydrofuran, 0° C. to room temperature; then ethanol, sodium hydroxide, hydrogen peroxide, 0° C. to room temperature; (23) Dess-Martin periodinane, dichloromethane; (24) a Grignard reagent of the type $R_5$-magnesium bromide, anhydrous tetrahydrofuran, nitrogen, −78° C. to room temperature; (25) hydrochloric acid (aqueous), ethanol, heat; (26) platinum (IV) oxide, ethanol, hydrogen, 3 bar; or palladium on carbon, ethyl acetate, hydrogen, 3 bar; (27) an alkylating agent of the type $R_6$-iodide, potassium tert-butoxide, tetrahydrofuran; (28) trifluoroacetic acid, dichloromethane.

Scheme 8 (When Y is a Bond and the Dotted Bond is a Single Bond)

In this reaction scheme $R_2$ and n are as previously described.

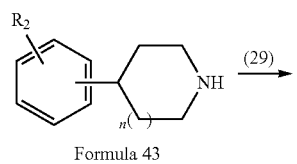

Formula 43

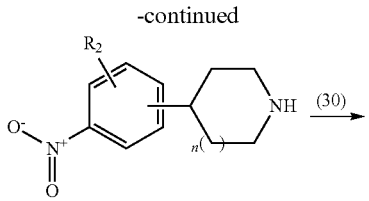

Formula 44

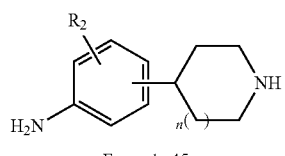

Formula 45

Conditions: (29) nitric acid, sulphuric acid, (30) platinum (IV) oxide, ethanol, hydrogen, 3 bar; or palladium on carbon, ethyl acetate, hydrogen, 3 bar.

Scheme 9 (Compounds of the Invention of Formula 1)

In this reaction scheme $R_1$, $R_2$, $R_3$, X, Y, Z and n have the meaning as previously defined.

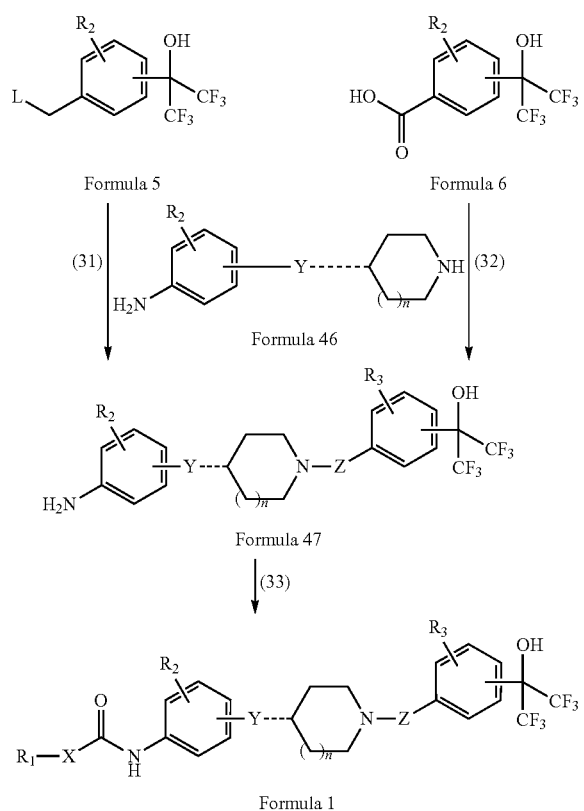

Conditions: (31) Formula 46, potassium carbonate, acetonitrile, room or elevated temperature; (32) Formula 46, N-(3-dimethylaminopropyl)-N'-ethylcarbodiimide hydrochloride or 1-propanephosphonic acid cyclic anhydride, dichloromethane, triethylamine; (33) When X is $NR_4$ or O: 4-nitrophenyl chloroformate or (bis(trichloromethyl)carbonate (triphosgene), dichloromethane, and an amine of Formula $R_1R_4NH$ or excess alcohol of Formula $R_1OH$, respectively; When X is bond: dichloromethane, triethylamine, and an acid chloride of Formula $R_1CO_2Cl$.

The amine derivatives of Formula 2, the ester derivatives of Formula 7, the benzyl bromide derivatives of Formula 9, the nitrophenyl derivatives of Formula 17, the acid chloride derivatives of Formula 22, and the amine derivatives of Formula 43 are compounds that can be prepared using methods well known in the art from commercially available intermediates.

An overview of protecting groups and methods for their removal is given in T. W. Greene and P. G. M. Wuts, "*Protective Groups in Organic Synthesis*", $2^{nd}$ edition, 1991, John Wiley & Sons, Inc.

The 1,1,1,3,3,3-hexafluoro-2-hydroxypropan-2-yl)phenyl derivatives of Formula I and their salts may contain at least one centre of chirality, and exist therefore as stereoisomers, including enantiomers and diastereomers. The present invention includes the aforementioned stereoisomers within its scope and each of the individual R and S enantiomers of the compounds of Formula I and their salts, substantially free, i.e. associated with less than 5%, preferably less than 2%, in particular less than 1% of the other enantiomer, and mixtures of such enantiomers in any proportions including the racemic mixtures containing substantially equal amounts of the two enantiomers. Methods for asymmetric synthesis whereby the pure stereoisomers are obtained are well known in the art, e.g. synthesis with chiral induction or starting from chiral intermediates, enantioselective enzymatic conversions, separation of stereoisomers or enantiomers using chromatography on chiral media. Such methods are for example described in *Chirality in Industry* (edited by A. N. Collins, G. N. Sheldrake and J. Crosby, 1992; John Wiley).

The present invention also embraces isotopically-labelled hexafluoroisopropanol derivatives of Formula I which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine, such as $^2H$, $^3H$, $^{13}C$, $^{14}C$, $^{15}N$, $^{18}O$, $^{17}O$, $^{35}S$, $^{18}F$, and $^{36}Cl$, respectively. Certain isotopically-labelled compounds of Formula (I) (e.g., those labelled with $^3H$ and $^{14}C$) are useful in compound and/or substrate tissue distribution assays. Tritiated (i.e., $^3H$) and carbon-14 (i.e., $^{14}C$) isotopes are particularly preferred for their ease of preparation and detectability. Further, substitution with heavier isotopes such as deuterium (i.e., $^2H$) may afford certain therapeutic advantages resulting from greater metabolic stability (e.g., increased in vivo half-life or reduced dosage requirements) and hence may be preferred in some circumstances. $^{11}C$ and $^{18}F$ are the preferred isotopes to be incorporated in a compound of the invention for use as a PET (Positron Emission Tomography) tracer. Isotopically labelled compounds of Formula (I) can generally be prepared by following procedures analogous to those disclosed in the Schemes and/or in the Examples hereinbelow, by substituting an appropriate isotopically labelled reagent for a non-isotopically labelled reagent.

Pharmaceutically acceptable salts may be obtained by treating a free base of a compound of Formula I with a mineral acid such as hydrochloric acid, hydrobromic acid, phosphoric acid and sulfuric acid, or an organic acid such as for example ascorbic acid, citric acid, tartaric acid, lactic acid, maleic acid, malonic acid, fumaric acid, glycolic acid, succinic acid, propionic acid, acetic acid, methane sulfonic acid, and the like.

The compounds of the invention may exist in unsolvated as well as in solvated forms with pharmaceutically acceptable solvents such as water, ethanol and the like. In general, the solvated forms are considered equivalent to the unsolvated forms for the purpose of the invention.

The present invention further provides pharmaceutical compositions comprising a hexafluoroisopropanol derivative having the general Formula I, or a pharmaceutically acceptable salt thereof, in admixture with pharmaceutically acceptable auxiliaries, and optionally other therapeutic agents. The term "acceptable" means being compatible with the other ingredients of the composition and not deleterious to the recipients thereof. Compositions include e.g. those suitable for oral, sublingual, subcutaneous, intravenous, epidural, intrathecal, intramuscular, transdermal, pulmonary, local, or rectal administration, and the like, all in unit dosage forms for administration.

For oral administration, the active ingredient may be presented as discrete units, such as tablets, capsules, powders, granulates, solutions, suspensions, and the like. For parenteral administration, the pharmaceutical composition of the invention may be presented in unit-dose or multi-dose containers, e.g. injection liquids in predetermined amounts, for example in sealed vials and ampoules, and may also be stored in a freeze dried (lyophilized) condition requiring only the addition of sterile liquid carrier, e.g. water, prior to use.

Mixed with such pharmaceutically acceptable auxiliaries, e.g. as described in the standard reference, Gennaro, A. R. et al., *Remington: The Science and Practice of Pharmacy* (20th Edition, Lippincott Williams & Wilkins, 2000, see especially Part 5: Pharmaceutical Manufacturing), the active agent may be compressed into solid dosage units, such as pills, tablets, or be processed into capsules, suppositories or patches. By means of pharmaceutically acceptable liquids the active agent can be applied as a fluid composition, e.g. as an injection preparation, in the form of a solution, suspension, emulsion, or as a spray, e.g. a nasal spray.

For making solid dosage units, the use of conventional additives such as fillers, colorants, polymeric binders and the like is contemplated. In general any pharmaceutically acceptable additive which does not interfere with the function of the active compounds can be used. Suitable carriers with which the active agent of the invention can be administered as solid compositions include lactose, starch, cellulose derivatives and the like, or mixtures thereof, used in suitable amounts. For parenteral administration, aqueous suspensions, isotonic saline solutions and sterile injectable solutions may be used, containing pharmaceutically acceptable dispersing agents and/or wetting agents, such as propylene glycol or butylene glycol.

The invention further includes a pharmaceutical composition, as hereinbefore described, in combination with packaging material suitable for said composition, said packaging material including instructions for the use of the composition for the use as hereinbefore described.

The hexafluoroisopropanol derivatives of the present invention were found to be modulators of LXRα and/or LXRβ, especially having agonistic activity thereon, and are as such useful in preventing and reducing the risk of atherosclerosis and related disorders associated with cholesterol and bile acids transport and metabolism, such as hypercholesterolemia (e.g. coronary heart disease), cholesterol gallstones, lipid storage diseases, diabetes and obesity.

The potential utility of LXR agonists in the treatment of atherosclerosis has been increasingly documented over the last few years (see for example Levin et al., *Arterioscler. Thromb. Vasc. Biol.* 1:135-142 (2005). Atherosclerosis is a disease of the arteries that exists for many years without causing symptoms. Advanced atherosclerotic plaques do however become vulnerable to rupture, promoting acute thrombosis and clinical events such as myocardial infarction (MI) and stroke. The primary cell type implicated in rupture of atherosclerotic plaques, and subsequent clinical events, is the macrophage.

The primary mechanism for achieving efficacy in atherosclerosis with an LXR agonist is expected to occur by lowering the cholesterol burden of arteries (via upregulation of ABCA1), to generate more stable lesions and thus reduce the clinical events. Additionally, LXR agonists may increase circulating HDL levels due to the role of ABCA1 in generation of nascent HDL by the liver.

The compounds of the invention are potentially also useful in further indications such as:

Inflammatory Disease:

Ligand activation of LXR has been shown to inhibit a number of inflammatory pathways e.g. Interleukin1-β, Interleukin-6, cyclooxygenase-2 and most recently shown to directly inhibit C-reactive protein expression. See Blaschke et al., *Circ. Res.* 99: 88-99. (2006). Compounds of the invention may have therapeutic utility in suppression of inflammation in inflammatory diseases such as contact dermitits (see Fowler et al., *J. Invest. Dermatol.* 120:246-55. (2003); neuroinflammatory diseases such as multiple sclerosis (Zhang-Gandhi and Drew. *J. Neuroimmunol.* 183:50-59. (2007)) and autoimmune encephalomyelitis. See Hindinger at al., *J. Neurosci. Res.* 84:1225-1234 (2006).

Proliferative Vascular Disease:

The LXR ligand T0901317 has been shown to inhibit vascular smooth muscle cell proliferation and neointima formation following balloon injury in vitro and in vivo. Compounds of the invention may therefore have therapeutic utility in proliferative vascular diseases. See Blaschke et al., *Circ. Res.* 95:110-123 (2004).

Diabetes/Metabolic Syndrome:

Recent literature has demonstrated efficacy of LXR agonists in animal models of insulin resistance and diabetes and thus compounds of the invention may have potential therapeutic utility in the treatment of diabetes and metabolic syndrome (see Liu et al., *Endocrinology.* 147:5061-5068 (2006); Fernandez-Veledo et al., *Diabetologia.* 49:3038-3048 (2006)).

Cancer:

The LXR agonist T0901317 delayed progression of tumours in an animal model of prostate cancer. Compounds of the invention may be potentially useful for treatment of prostate cancer. See Chuu et al., *Cancer. Res.* 66:6482-6486 (2006).

Neurodegenerative Disease:

Via modulation of cellular cholesterol levels, LXR agonists can reduce the deposition of (β-amyloid in the brain. In addition T0901317 has been shown to lower deposition of β-amyloid but also improve memory. See Riddell et al., *Mol. Cell. Neurosci.* 34: 621-628 (2007). The agonist derivatives of the present invention may therefore have therapeutic utility in neurodegenerative diseases such as Alzheimers disease.

Combination Therapies:

The compounds of the invention may be combined with another therapeutic agent that is useful in the treatment of other metabolic disorders such as; hypertension, hyperlipidaemias, dyslipidaemias, diabetes, chronic inflammatory disorders, obesity and in any condition where enhancement of reverse cholesterol transport and/or improvement of LDL: HDL ratios would be of potential clinical benefit. Examples of such therapies are: inhibitors of 3-hydroxy-3-methyl-glutaryl-CoA reductase (HMG CoA reductase) (e.g. atorvastatin, pravastatin, simvastatin, lovastatin, rosuvastatin and others), cholesterol absorption inhibitors (e.g. ezetimibe), bile sequestrants (e.g. cholestyramine), microsomal triglyceride transfer protein (MTP) inhibitors, peroxisome proliferator-activated receptor modulators (e.g. muraglitazar, rosiglitazone, fibrates and others), cholesterol ester transfer protein inhibitors, nicotinic acid derivatives (e.g. Niaspan® etc), Acyl coenzyme A: cholesterol acyl transferase (ACAT) inhibitors (e.g. eflucimibe), farnesoid X receptor modulators, therapies used for the treatment of metabolic syndrome or type 2 diabetes e.g. metformin. Compounds of the invention may be combined with anti-inflammatory therapies (e.g. aspirin) and with treatments for neurodegenerative diseases (e.g Aricept®, Exelon®, Reminyl® and Ebixa®).

The compounds of the invention may be administered for humans in a sufficient amount and for a sufficient amount of time to alleviate the symptoms. Illustratively, daily dosage levels for humans can be in the range of 0.001-50 mg per kg body weight, preferably in a daily dosage of 0.01-20 mg per kg body weight.

The invention is illustrated by the following Examples.

GENERAL EXPERIMENTAL

High Performance Liquid Chromatography (HPLC)

HPLC purification is used within this experimental section and refers to High Performance Liquid Chromatography. Some examples of general methods that may be used to purify compounds are: acidic reverse phase HPLC (water/acetonitrile/0.1% trifluoroacetic acid) using a standard gradient of 5% acetonitrile/95% water to 100% acetonitrile or basic reverse phase HPLC (water/acetonitrile/0.1% ammonia solution) using a standard gradient of 10% acetonitrile/90% water to 100% acetonitrile. UV detection e.g. 254 nM is used for the collection of fractions from HPLC. This description gives general methods and variations in types of equipment, columns, mobile phase, detection wavelength, solvent gradient and run time may also be used to purify compounds.

Free Base and Salts

After purification by acidic HPLC basic products can either be isolated as the trifluoroacetic acid salt or liberated as the free base by common generic methods e.g. strong cation exchange chromatography eluting with 2M ammonia in methanol or silica carbonate column chromatography or partitioning between an organic solvent e.g. ethyl acetate and aqueous base e.g. sodium hydrogen carbonate, separating the organic layer, drying with inorganic solid e.g. magnesium sulfate, filtering and concentration under reduced pressure.

The free base of products can also be converted to hydrochloride salts by standard methods e.g. dissolving the free base in dichloromethane and adding 2M hydrochloric acid in ether and concentrating under reduced pressure to give the hydrochloride salt.

Abbreviations $CDCl_3$: chloroform-d; $(CD_3)_2SO$: diemthylsulfoxide-$d_6$; HPLC: high performance liquid chromatography; SCX: strong cation exchange.

Example 1

1-(Cyclopropylmethyl)-3-(4-(1-(4-(1,1,1,3,3,3-hexafluoro-2-hydroxypropan-2-yl)benzyl)piperidin-4-yloxy)phenyl)urea

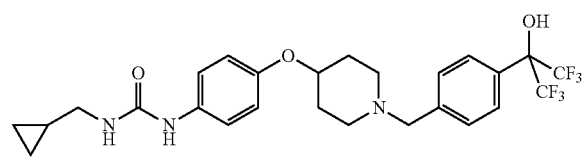 [SMILES: O=C(NCC1CC1)Nc1ccc(OC2CCN(Cc3ccc(C(O)(C(F)(F)F)C(F)(F)F)cc3)CC2)cc1]

A: 4-(4-Nitrophenoxy)piperidine

Tert-butyl 4-(4-nitrophenoxy)piperidine-1-carboxylate (3.10 mmol, 1 g) was dissolved in dichloromethane (10 mL). Trifluoroacetic acid (3 mL) was added and the reaction was stirred at room temperature for 30 minutes. The reaction mixture was concentrated under vacuum and purified by SCX chromatography to afford the title compound (600 mg). MS (ESI) m/z 223.3 [M+H]$^+$ B: 1,1,1,3,3,3-Hexafluoro-2-(4-((4-(4-nitrophenoxy)piperidin-1-yl)methyl)phenyl)propan-2-ol 4-(4-Nitrophenoxy)piperidine (2.70 mmol, 600 mg), 2-(4-(bromomethyl)phenyl)-1,1,1,3,3,3-hexafluoropropan-2-ol (2.70 mmol, 910 mg) and potassium carbonate (5.40 mmol, 746 mg) were combined and stirred at 70° C. in acetonitrile (20 mL) overnight. The reaction mixture was filtered and the filtrate concentrated under vacuum to afford the title compound. MS (ESI) m/z 490.0 [M+H]$^+$ C: 2-(4-((4-(4-Aminophenoxy)piperidin-1-yl)methyl)phenyl)-1,1,1,3,3,3-hexafluoropropan-2-ol 1,1,1,3,3,3-Hexafluoro-2-(4-((4-(4-nitrophenoxy)piperidin-1-yl)methyl)phenyl)propan-2-ol (4.01 mmol, 1.92 g) and palladium (10% on carbon, Degussa) (0.040 mmol, 0.085 g) were hydrogenated in methanol (20 mL) at 5 bar for 1 hour at room temperature. The reaction mixture was filtered and the filtrate concentrated under vacuum to afford the title compound. MS (ESI) m/z 449.1 [M+H]$^+$ D: 1-(Cyclopropylmethyl)-3-(4-(1-(4-(1,1,1,3,3,3-hexafluoro-2-hydroxypropan-2-yl)benzyl)piperidin-4-yloxy)phenyl)urea A solution of 2-(4-((4-(4-aminophenoxy)piperidin-1-yl)methyl)phenyl)-1,1,1,3,3,3-hexafluoropropan-2-ol (0.446 mmol, 200 mg) and 4-nitrophenyl carbonochloridate (0.446 mmol, 90 mg) in dichloromethane (1 mL) were stirred at room temperature for 30 minutes. Cyclopropylmethanamine (0.892 mmol, 0.091 mL, 63.4 mg) was added, followed by triethylamine (1.338 mmol, 0.187 mL, 135 mg) and the reaction stirred at room temperature overnight. The reaction mixture was diluted with dichloromethane and saturated sodium bicarbonate solution was added. The organic layer was separated and concentrated under vacuum. The residue was purified by silica column chromatography (eluent 2-8% methanol in dichloromethane) to give the title compound (55.3 mg). MS (ESI) m/z 546.2 [M+H]$^+$ The following compounds were prepared in a similar manner:

1B: 1-(4-(1-(4-(1,1,1,3,3,3-Hexafluoro-2-hydroxypropan-2-yl)benzyl)piperidin-4-yloxy)phenyl)-3-((1r,4r)-4-hydroxycyclohexyl)urea

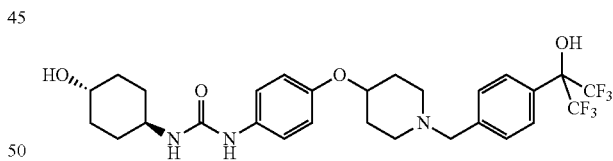

MS (ESI) m/z 590.3 [M+H]$^+$

1C: 1-(4-(1-(4-(1,1,1,3,3,3-Hexafluoro-2-hydroxypropan-2-yl)benzyl)piperidin-4-yloxy)phenyl)-3-(tetrahydro-2H-pyran-4-yl)urea

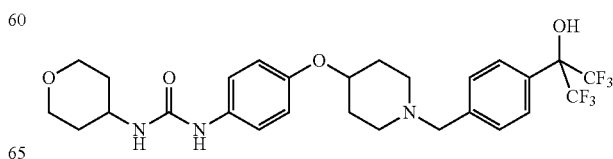

MS (ESI) m/z 576.3 [M+H]$^+$

1D: 1-(4-(1-(4-(1,1,1,3,3,3-Hexafluoro-2-hydroxypropan-2-yl)benzyl)piperidin-4-yloxy)phenyl)-3-(2-hydroxy-2-methylpropyl)urea

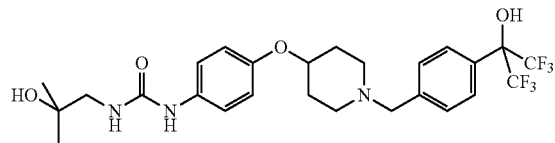 [SMILES: CC(C)(O)CNC(=O)Nc1ccc(OC2CCN(Cc3ccc(C(O)(C(F)(F)F)C(F)(F)F)cc3)CC2)cc1]

MS (ESI) m/z 564.2 [M+H]$^+$

1E: 1-(4-(1-(4-(1,1,1,3,3,3-Hexafluoro-2-hydroxypropan-2-yl)benzyl)piperidin-4-yloxy)phenyl)-3-(4-hydroxy-1,1-dioxo-tetrahydro-1λ$^6$-thiophen-3-yl)urea

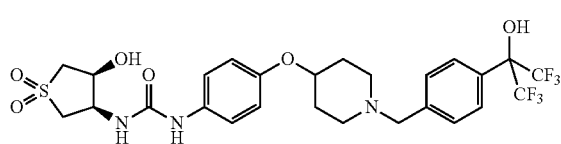 [SMILES: O=C(Nc1ccc(OC2CCN(Cc3ccc(C(O)(C(F)(F)F)C(F)(F)F)cc3)CC2)cc1)N[C@H]1CS(=O)(=O)C[C@H]1O]

MS (ESI) m/z 626.0 [M+H]$^+$

1F: 1-(4-(1-(4-(1,1,1,3,3,3-Hexafluoro-2-hydroxypropan-2-yl)benzyl)piperidin-4-yloxy)phenyl)-3-(pyridazin-4-yl)urea

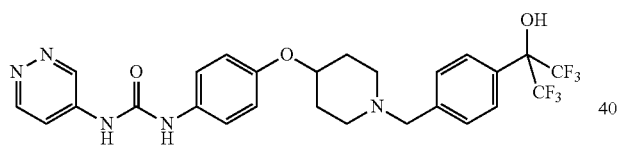

MS (ESI) m/z 570.2 [M+H]$^+$

Example 2

1-(4-(1-(4-(1,1,1,3,3,3-Hexafluoro-2-hydroxypropan-2-yl)benzyl)piperidin-4-yloxy)phenyl)-3-(pyridin-4-yl)urea

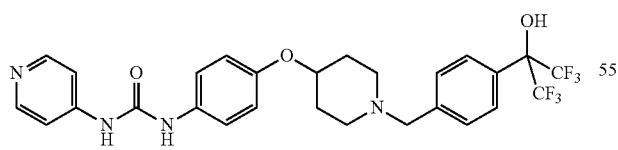

2-(4-((4-(4-Aminophenoxy)piperidin-1ll)methyl)phenyl)-1,1,1,3,3,3-hexafluoro-propan-2-ol (0.223 mmol, 100 mg) and phenyl pyridin-4-ylcarbamate (0.335 mmol, 71.7 mg) were combined in tetrahydrofuran (2 mL) and heated to 80° C. overnight. The reaction mixture was concentrated under vacuum and the residue was purified by prep-HPLC (acidic conditions) to give the title compound (30.6 mg).
MS (ESI) m/z 569.3 [M+H]$^+$ The following compounds were prepared in a similar manner:

2B: 1-(5-Cyanopyridin-2-yl)-3-(4-(1-(4-(1,1,1,3,3,3-hexafluoro-2-hydroxypropan-2-yl)benzyl)piperidin-4-yloxy)phenyl)urea

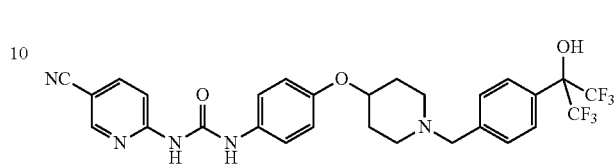

MS (ESI) m/z 594.2 [M+H]$^+$

2C: 1-(3-Fluoropyridin-4-yl)-3-(4-(1-(4-(1,1,1,3,3,3-hexafluoro-2-hydroxypropan-2-yl)benzyl)piperidin-4-yloxy)phenyl)urea

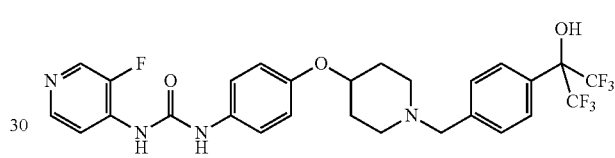

MS (ESI) m/z 587.0 [M+H]$^+$

2D: 1-(4-(1-(4-(1,1,1,3,3,3-Hexafluoro-2-hydroxypropan-2-yl)benzyl)piperidin-4-yloxy)phenyl)-3-(pyrimidin-2-yl)urea

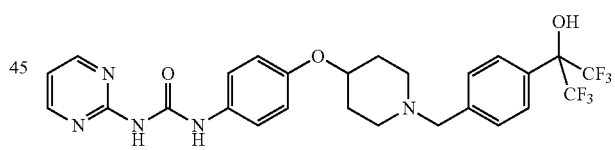

MS (ESI) m/z 570.2 [M+H]$^+$

2E: 1-(4-(1-(4-(1,1,1,3,3,3-Hexafluoro-2-hydroxypropan-2-yl)benzyl)piperidin-4-yloxy)phenyl)-3-(pyrimidin-4-yl)urea

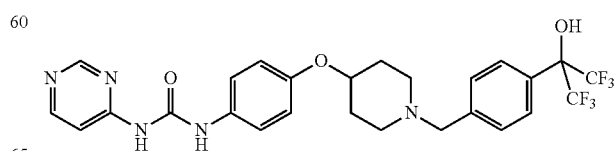

MS (ESI) m/z 570.5 [M+H]$^+$

Example 3

1-(Cyclopropylmethyl)-3-(4-(1-(4-(1,1,1,3,3,3-hexafluoro-2-hydroxypropan-2-yl)benzyl)pyrrolidin-3-yloxy)phenyl)urea

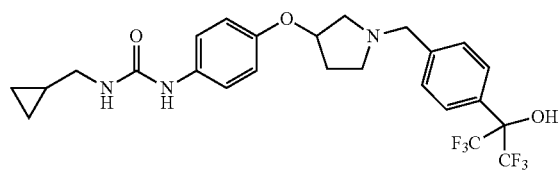 [SMILES: O=C(NCC1CC1)Nc1ccc(OC2CCN(Cc3ccc(C(O)(C(F)(F)F)C(F)(F)F)cc3)C2)cc1]

A: 3-(4-Nitrophenoxy)pyrrolidine tert-Butyl 3-(4-nitrophenoxy)pyrrolidine-1-carboxylate (9.73 mmol, 3 g) was dissolved in dichloromethane (2.5 mL). Trifluoroacetic acid (1 mL) was added and the reaction mixture stirred at room temperature for 30 minutes. The reaction was purified by SCX chromatography to give the title compound (2.11 g). MS (ESI) m/z 209.0 [M+H]$^+$

B: 2-(4-((3-(4-Aminophenoxy)pyrrolidin-1-yl)methyl)phenyl)-1,1,1,3,3,3-hexafluoropropan-2-ol Step 1: 2-(4-(Bromomethyl)phenyl)-1,1,1,3,3,3-hexafluoropropan-2-ol (9.61 mmol, 4.63 mL, 3.24 g), 3-(4-nitrophenoxy)pyrrolidine (9.61 mmol, 2 g) and potassium carbonate (19.21 mmol, 2.65 g) were combined and stirred at room temperature in acetonitrile (50 mL) for 1 hour. The reaction mixture was filtered and concentrated under vacuum. The residue was purified by silica column chromatography (eluent: dichloromethane to 15% methanol in dichloromethane) and SCX chromatography to afford the intermediate 1,1,1,3,3,3-hexafluoro-2-(4-((3-(4-nitrophenoxy)pyrrolidin-1-yl)methyl)phenyl)propan-2-ol (750 mg).

Step 2: 1,1,1,3,3,3-Hexafluoro-2-(4-((3-(4-nitrophenoxy)pyrrolidin-1-yl)methyl)-phenyl)propan-2-ol (1.572 mmol, 730 mg) and palladium (10% on carbon, Degussa) (0.016 mmol, 33.5 mg) were hydrogenated in ethanol (15 mL) at 3 bar at room temperature for 1 hour. The reaction mixture was filtered through celite and concentrated under vacuum to give the title compound (700 mg).

MS (ESI) m/z 435.0 [M+H]$^+$

C: 1-(Cyclopropylmethyl)-3-(4-(1-(4-(1,1,1,3,3,3-hexafluoro-2-hydroxypropan-2-yl)benzyl)pyrrolidin-3-yloxy)phenyl)urea A solution of 2-(4-((3-(4-aminophenoxy)pyrrolidin-1-yl)methyl)phenyl)-1,1,1,3,3,3-hexafluoropropan-2-ol (0.345 mmol, 150 mg) and 4-nitrophenyl carbonochloridate (0.345 mmol, 69.6 mg) in tetrahydrofuran (5 mL) was stirred at room temperature for 30 minutes. Cyclopropylmethanamine (0.691 mmol, 49.1 mg) was added, followed by triethylamine (0.691 mmol, 0.096 mL, 69.9 mg) and the reaction stirred at room temperature overnight. The reaction mixture was diluted with dichloromethane/saturated sodium bicarbonate solution and filtered through a hydrophobic frit. The organic layer was concentrated under vacuum. The residue was purified by prep-HPLC (acidic conditions) and SCX chromatography to give title compound (30 mg).

MS (ESI) m/z 532.2 [M+H]$^+$

The following compound was prepared in a similar manner:

3B: 1-(4-(1-(4-(1,1,1,3,3,3-Hexafluoro-2-hydroxypropan-2-yl)benzyl)pyrrolidin-3-yloxy)phenyl)-3-(3,3,3-trifluoro-2-hydroxy-2-methylpropyl)urea

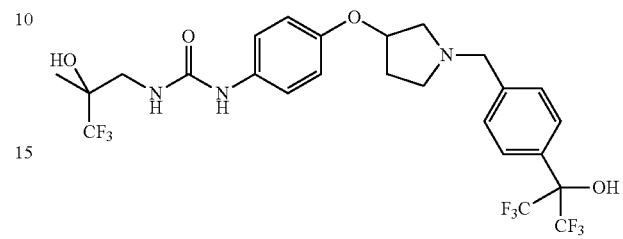

MS (ESI) m/z 604.0 [M+H]$^+$

Example 4

1-(Cyclopropylmethyl)-3-(4-(1-(4-(1,1,1,3,3,3-hexafluoro-2-hydroxypropan-2-yl)benzoyl)piperidin-4-yloxy)phenyl)urea

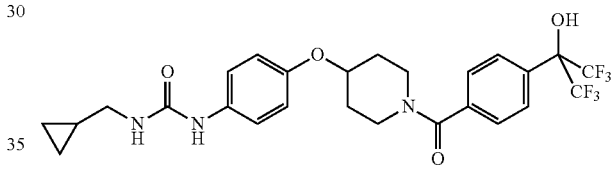

A: 1-(Cyclopropylmethyl)-3-(4-hydroxyphenyl)urea

4-Aminophenol (18.33 mmol, 2 g) and 4-nitrophenyl carbonochloridate (18.33 mmol, 3.69 g) in dichloromethane (10 mL) were stirred at room temperature for 30 minutes. Cyclopropylmethanamine (36.7 mmol, 3.72 mL, 2.61 g) was added followed triethylamine (55.0 mmol, 7.66 mL, 5.56 g). The reaction was allowed to stir at room temperature overnight. The reaction mixture was diluted with dichloromethane/saturated sodium hydrogen carbonate solution and filtered through a hydrophobic frit. The organic layer was concentrated and the residue was purified by silica column chromatography (eluent: 2-8% methanol in dichloromethane) to give the title compound (1.4 g). MS (ESI) m/z 207.1 [M+H]$^+$

B: tert-Butyl 4-(4-(3-(cyclopropylmethyl)ureido)phenoxy)piperidine-1-carboxylate To a stirring solution of 1-(cyclopropylmethyl)-3-(4-hydroxyphenyl)urea (6.79 mmol, 1.4 g) in dimethylacetamide (50 mL) was added cesium fluoride (20.36 mmol, 3.09 g) followed by a solution of tert-butyl 4-(methylsulfonyloxy)piperidine-1-carboxylate (8.15 mmol, 2.276 g) in dimethylacetamide (50 mL). The resulting suspension was heated to 85° C. overnight. The reaction mixture was filtered and the filtrate concentrated under vacuum. The residue was dissolved in dichloromethane and washed with water. The organic layer was separated, dried over magnesium sulfate and concentrated under vacuum. The residue was dissolved in dichloromethane and purified by column chromatography (eluent 2-8% methanol in dichloromethane) to afford the title compound. MS (ESI) m/z 390.0 [M+H]+

C: 1-(Cyclopropylmethyl)-3-(4-(piperidin-4-yloxy) phenyl)urea

To a stirring solution of tert-butyl 4-(4-(3-(cyclopropylmethyl)ureido)phenoxy)piperidine-1-carboxylate (2.57 mmol, 1 g) in dichloromethane (10 mL) was added trifluoroacetic acid (2 mL). The resulting solution was stirred at room temperature for 30 minutes then was concentrated under vacuum. The residue was dissolved in dichloromethane and purified by SCX chromatography to give the title compound (350 mg). MS (ESI) m/z 290.1 [M+H]+

D: 1-(Cyclopropylmethyl)-3-(4-(1-(4-(1,1,1,3,3,3-hexafluoro-2-hydroxypropan-2-yl)benzoyl)piperidin-4-yloxy)phenyl)urea 1-(cyclopropylmethyl)-3-(4-(piperidin-4-yloxy)phenyl) urea (1.037 mmol, 300 mg), 4-(1,1,1,3,3,3-hexafluoro-2-hydroxypropan-2-yl)benzoic acid (1.037 mmol, 299 mg) and triethylamine (3.11 mmol, 0.432 mL, 315 mg) were combined and stirred at room temperature in dichloromethane (5 mL). 1-Propanephosphonic acid cyclic anhydride (1.555 mmol, 0.926 mL, 990 mg; 50% solution in ethyl acetate) was added and the reaction stirred at room temperature for 1 hour. The reaction mixture was washed with saturated sodium bicarbonate solution and the organic layer was separated, dried and concentrated under vacuum. The residue was dissolved in dichloromethane and purified by silica column chromatography (eluent 2-8% methanol in dichloromethane) to afford the title compound (24 mg). MS (ESI) m/z 560.2 [M+H]+

Example 5

1-(3-Bromo-4-(1-(4-(1,1,1,3,3,3-hexafluoro-2-hydroxypropan-2-yl)benzyl)piperidin-4-yloxy)phenyl)-3-(tetrahydro-2H-pyran-4-yl)urea

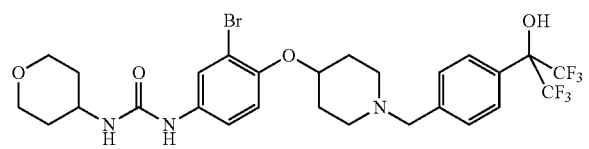 [SMILES: O=C(Nc1ccc(OC2CCN(Cc3ccc(C(O)(C(F)(F)F)C(F)(F)F)cc3)CC2)c(Br)c1)NC1CCOCC1]

A: 4-(2-Bromo-4-nitrophenoxy)piperidine tert-Butyl 4-(2-bromo-4-nitrophenoxy)piperidine-1-carboxylate (12.21 mmol, 4.9 g) was dissolved in dichloromethane (40 mL) and trifluoroacetic acid (73.3 mmol, 8.35 g) added. The mixture was stirred at room temperature for 3 hours before concentrating under reduced pressure. The resulting residue was dissolved in dichloromethane (150 mL) and washed with a saturated solution of sodium bicarbonate (3×50 mL). The organic phase was dried over magnesium sulfate, filtered and concentrated under reduced pressure to afford the title compound (3.3 g).
MS (ESI) m/z 303.1 [M+H]+

B: 2-(4-((4-(2-Bromo-4-nitrophenoxy)piperidin-1-yl)methyl)phenyl)-1,1,1,3,3,3-hexafluoropropan-2-ol 4-(2-Bromo-4-nitrophenoxy)piperidine (10.96 mmol, 3.3 g), 2-(4-(bromomethyl)-phenyl)-1,1,1,3,3,3-hexafluoropropan-2-ol (10.96 mmol, 3.69 g) and potassium carbonate (32.9 mmol, 4.54 g) were combined in acetonitrile (40 mL) and the mixture stirred at room temperature overnight. The mixture was concentrated under reduced pressure and the resulting residue dissolved in dichloromethane (150 mL). The organic phase was washed with water (2×50 mL) then brine (50 mL). The organic phase was dried over magnesium sulfate, filtered and concentrated under reduced pressure. The resulting residue was purified by silica gel column chromatography (eluting with dichloromethane to 10% methanol/dichloromethane) to afford the title compound (5.25 g). MS (ESI) m/z 558.8 [M+H]+

C: 2-(4-((4-(4-Amino-2-bromophenoxy)piperidin-1-yl)methyl)phenyl)-1,1,1,3,3,3-hexafluoropropan-2-ol Iron (94 mmol, 5.24 g) (reduced powder) was added to a suspension 2-(4-((4-(2-bromo-4-nitrophenoxy)piperidin-1-yl)methyl)phenyl)-1,1,1,3,3,3-hexafluoropropan-2-ol (9.40 mmol, 5.24 g) in 2-propanol (100 mL) containing concentrated hydrochloric acid (1 mL) and the mixture refluxed for 4.5 hours. The mixture was cooled, diluted with dichloromethane and filtered through dicalite. The filtrate was washed with sodium carbonate solution, the organic phase dried over magnesium sulfate and concentrated under reduced pressure to afford the title compound (4.5 g).
MS (ESI) m/z 526.8 [M+H]+

D: 1-(3-Bromo-4-(1-(4-(1,1,1,3,3,3-hexafluoro-2-hydroxypropan-2-yl)benzyl)piperidin-4-yloxy)phenyl)-3-(tetrahydro-2H-pyran-4-yl)urea 2-(4-((4-(4-Amino-2-bromophenoxy)piperidin-1-yl)methyl)phenyl)-1,1,1,3,3,3-hexafluoropropan-2-ol (0.379 mmol, 200 mg) and 4-nitrophenyl chloroformate (0.379 mmol, 76 mg) were combined in tetrahydrofuran (1 mL) and the mixture stirred at room temperature for 45 minutes. Tetrahydro-2H-pyran-4-amine (0.379 mmol, 38.4 mg) followed by triethylamine (1.138 mmol, 115 mg) were added and the mixture stirred overnight. The mixture was concentrated under reduced pressure and the resulting residue was purified by HPLC then treated with strong cation exchange column chromatography to afford the title compound (107 mg).
MS (ESI) m/z 655.0 [M+H]+

Example 6

1-((4-(Dimethylamino)tetrahydro-2H-pyran-4-yl) methyl)-3-(4-((1-(4-(1,1,1,3,3,3-hexafluoro-2-hydroxypropan-2-yl)benzyl)piperidin-4-yl)methyl) phenyl)urea

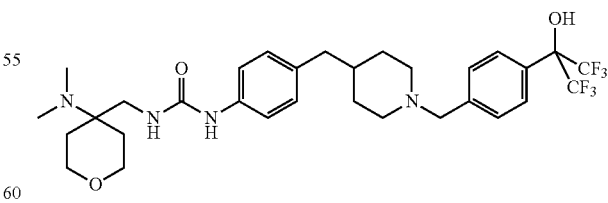

A: tert-Butyl 4-(4-nitrobenzylidene)piperidine-1-carboxylate

Diethyl 4-nitrobenzylphosphonate (36 g, 132 mmol) and tert-butyl 4-oxopiperidine-1-carboxylate (26.3 g, 132 mmol)

were stirred in tetrahydrofuran (230 mL) and cooled in an ice bath. Sodium hydride was added (6.85 g, 171 mmol) and the reaction was taken off the ice bath and stirred for 3 hours at room temperature. The reaction was quenched with water and extracted with dichloromethane, dried (magnesium sulphate), filtered and evaporated under reduced pressure. The crude material was purified by silica chromatography using a dichloromethane solvent system. The oil obtained was triturated with heptane and filtered to give the title compound as a yellow solid (34.24 g). $^1$H NMR (CDCl$_3$, 400 MHz): δ 8.18 (d, 2H), 7.33 (d, 2H), 6.40 (s, 1H), 3.54 (t, 2H), 3.43 (t, 2H), 2.46 (t, 2H), 2.38 (t, 2H), 1.48 (s, 9H)

B: 4-(4-Nitrobenzylidene)piperidine tert-Butyl 4-(4-nitrobenzylidene)piperidine-1-carboxylate (31.4 mmol, 10 g) was stirred in a mixture of dichloromethane/trifluoroacetic acid for 3 hours. The reaction was concentrated under reduced pressure and water was added. Solid sodium hydrogen carbonate was added portionwise until no further gas was evolved. The aqueous mixture was extracted with ethyl acetate. The organic phase was dried (magnesium sulfate), filtered and concentrated under reduced pressure to give the title compound (5.2 g). MS (ESI) m/z 219.1 [M+H]$^+$ C: 1,1,1,3,3,3-Hexafluoro-2-(4-((4-(4-nitrobenzylidene)piperidin-1-yl)methyl)phenyl)propan-2-ol

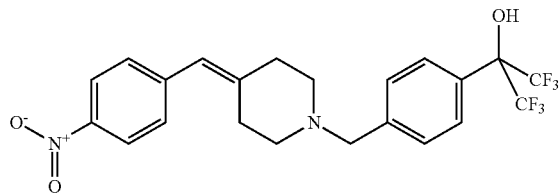 [SMILES: O=[N+]([O-])c1ccc(C=C2CCN(Cc3ccc(C(O)(C(F)(F)F)C(F)(F)F)cc3)CC2)cc1]

To a stirred mixture of 4-(4-nitrobenzylidene)piperidine (23.83 mmol, 5.2 g) and potassium carbonate (31.0 mmol, 4.28 g) in acetonitrile was added a solution of 2-(4-(bromomethyl)phenyl)-1,1,1,3,3,3-hexafluoropropan-2-ol (23.83 mmol, 8.03 g) in acetonitrile. The reaction was stirred for 5 hours then was concentrated under reduced pressure. Dichloromethane was added and the reaction was filtered. The filtrate was chromatographed on silica (eluting with a gradient of dichloromethane to dichloromethane/ethyl acetate) to give the title compound (7.3 g).
MS (ESI) m/z 475.2 [M+H]$^+$ D: 2-(4-((4-(4-Aminobenzyl)piperidin-1-yl)methyl)phenyl)-1,1,1,3,3,3-hexafluoropropan-2-ol

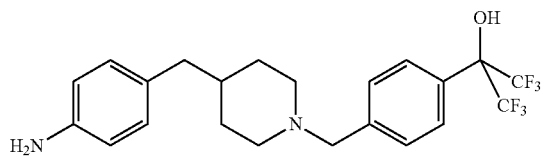 [SMILES: Nc1ccc(CC2CCN(Cc3ccc(C(O)(C(F)(F)F)C(F)(F)F)cc3)CC2)cc1]

A stirred mixture of 1,1,1,3,3,3-hexafluoro-2-(4-((4-(4-nitrobenzylidene)piperidin-1-yl)methyl)phenyl)propan-2-ol (15.39 mmol, 7.3 g) and palladium on carbon (5%) (0.308 mmol, 0.328 g) in ethyl acetate was hydrogenated at 3 bar until the desired amount of hydrogen was consumed. The mixture was filtered through celite washing with ethyl acetate. The filtrate was concentrated under reduced pressure. The residue was chromatographed on silica (eluting with a gradient of dichloromethane to ethyl acetate) to give the title compound (4.3 g). MS (ESI) m/z 447.2 [M+H]$^+$ E: 1-((4-(Dimethylamino)tetrahydro-2H-pyran-4-yl) methyl)-3-(4-((1-(4-(1,1,1,3,3,3-hexafluoro-2-hydroxypropan-2-yl)benzyl)piperidin-44)methyl)phenyl)urea 2-(4-((4-(4-Aminobenzyl)piperidin-1-yl)methyl)phenyl)-1,1,1,3,3,3-hexafluoropropan-2-ol (0.448 mmol, 200 mg) and 4-nitrophenyl carbonochloridate (0.448 mmol, 90 mg) in tetrahydrofuran (5 mL) were stirred at room temperature for 30 minutes. 4-(Aminomethyl)-N,N-dimethyltetrahydro-2H-pyran-4-amine (0.896 mmol, 0.203 mL, 142 mg) was added. The reaction was allowed to stir at room temperature overnight. The reaction was purified by silica column chromatography (eluent: dichloromethane to 15% methanol in dichloromethane) to give the title compound (105 mg).

MS (ESI) m/z 631.2 [M+H]$^+$

The following compounds were prepared in a similar manner:

6B: 1-((4-Aminotetrahydro-2H-pyran-4-yl)methyl)-3-(4-((1-(4-(1,1,1,3,3,3-hexafluoro-2-hydroxypropan-2-yl)benzyl)piperidin-4-yl)methyl)phenyl)urea

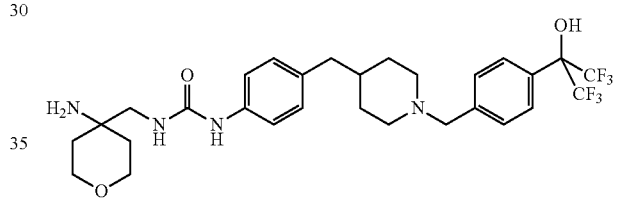

MS (ESI) m/z 603.2 [M+H]$^+$

6C: 1-(4-((1-(4-(1,1,1,3,3,3-Hexafluoro-2-hydroxypropan-2-yl)benzyl)piperidin-4-yl)methyl)phenyl)-3-(tetrahydro-2H-pyran-3-yl)urea

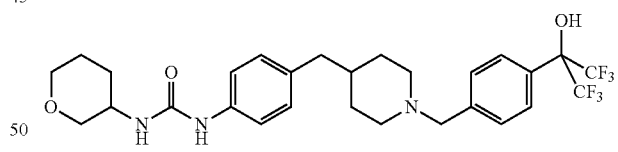

MS (ESI) m/z 574.2 [M+H]$^+$

6D: 1-Cyclopropyl-3-(4-((1-(4-(1,1,1,3,3,3-hexafluoro-2-hydroxypropan-2-yl)benzyl)piperidin-4-yl)methyl)phenyl)urea

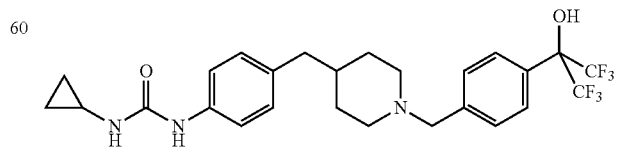

MS (ESI) m/z 530.2 [M+H]$^+$

6E: 1-(4-((1-(4-(1,1,1,3,3,3-Hexafluoro-2-hydroxypropan-2-yl)benzyl)piperidin-4-yl)methyl)phenyl)-3-propylurea

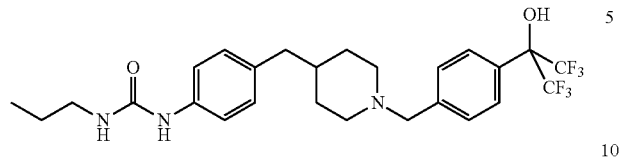

MS (ESI) m/z 532.2 [M+H]$^+$

6F: 1-(2-Ethoxyethyl)-3-(4-((1-(4-(1,1,1,3,3,3-hexafluoro-2-hydroxypropan-2-yl)benzyl)piperidin-4-yl)methyl)phenyl)urea

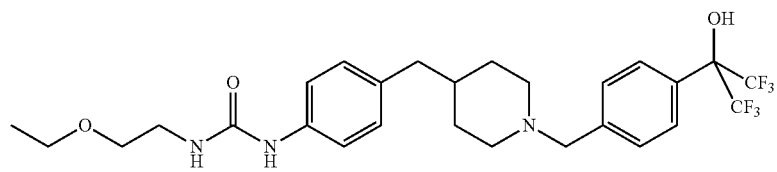 [SMILES: CCOCCNC(=O)Nc1ccc(CC2CCN(Cc3ccc(C(O)(C(F)(F)F)C(F)(F)F)cc3)CC2)cc1]

MS (ESI) m/z 562.2 [M+H]$^+$

6G: 1-(2,3-Dihydroxypropyl)-3-(4-((1-(4-(1,1,1,3,3,3-hexafluoro-2-hydroxypropan-2-yl)benzyl)piperidin-4-yl)-methyl)phenyl)urea

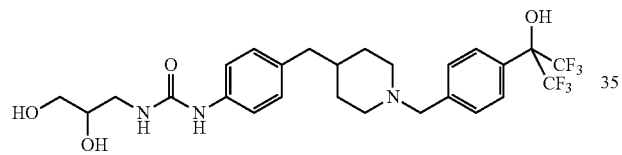

MS (ESI) m/z 564.2 [M+H]$^+$

6H: 1-(4-((1-(4-(1,1,1,3,3,3-Hexafluoro-2-hydroxypropan-2-yl)benzyl)piperidin-4-yl)methyl)phenyl)-3-(2-morpholinoethyl)urea

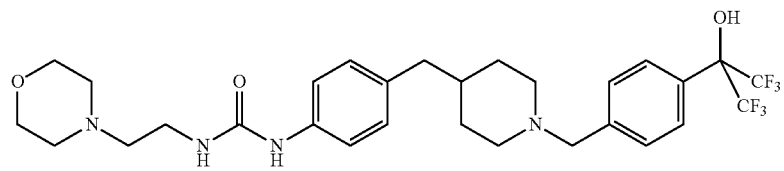 [SMILES: O=C(NCCN1CCOCC1)Nc1ccc(CC2CCN(Cc3ccc(C(O)(C(F)(F)F)C(F)(F)F)cc3)CC2)cc1]

MS (ESI) m/z 603.2 [M+H]$^+$

6I: 1-(4-((1-(4-(1,1,1,3,3,3-Hexafluoro-2-hydroxypropan-2-yl)benzyl)piperidin-4-yl)methyl)phenyl)-3-(pyridin-4-ylmethyl)urea

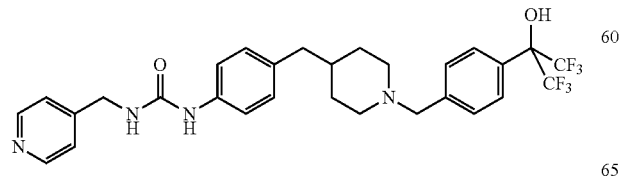

MS (ESI) m/z 581.2 [M+H]$^+$

6J: 1-(4-((1-(4-(1,1,1,3,3,3-Hexafluoro-2-hydroxypropan-2-yl)benzyl)piperidin-4-yl)methyl)phenyl)-3-(2-(pyridin-4-yl)ethyl)urea

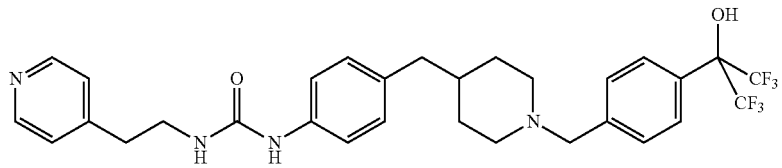 [SMILES: O=C(NCCc1ccncc1)Nc1ccc(CC2CCN(Cc3ccc(C(O)(C(F)(F)F)C(F)(F)F)cc3)CC2)cc1]

MS (ESI) m/z 595.2 [M+H]+

6K: 1-(4-((1-(4-(1,1,1,3,3,3-Hexafluoro-2-hydroxypropan-2-yl)benzyl)piperidin-4-yl)methyl)phenyl)-3-((5-methylisoxazol-3-yl)methyl)urea

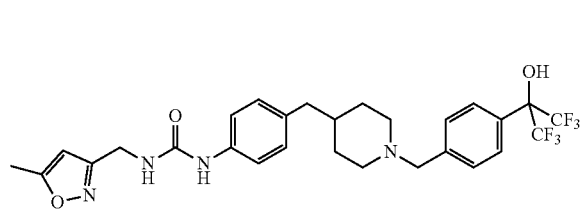 [SMILES: Cc1cc(CNC(=O)Nc2ccc(CC3CCN(Cc4ccc(C(O)(C(F)(F)F)C(F)(F)F)cc4)CC3)cc2)no1]

MS (ESI) m/z 585.2 [M+H]+

6L: 1-(2-(Furan-2-yl)-2-hydroxyethyl)-3-(4-((1-(4-(1,1,1,3,3,3-hexafluoro-2-hydroxypropan-2-yl)benzyl)piperidin-4-yl)methyl)phenyl)urea

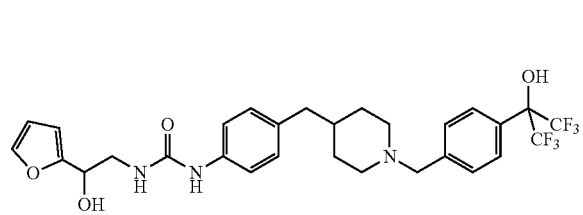 [SMILES: O=C(NCC(O)c1ccco1)Nc1ccc(CC2CCN(Cc3ccc(C(O)(C(F)(F)F)C(F)(F)F)cc3)CC2)cc1]

MS (ESI) m/z 600.2 [M+H]+

6M: N-(4-((1-(4-(1,1,1,3,3,3-Hexafluoro-2-hydroxypropan-2-yl)benzyl)piperidin-4-yl)methyl)phenylpiperidine-1-carboxamide

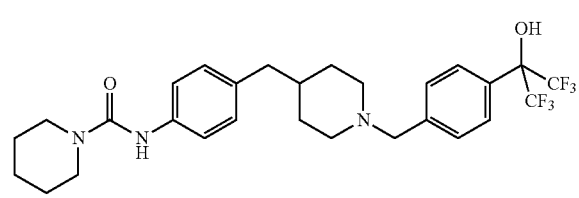 [SMILES: O=C(Nc1ccc(CC2CCN(Cc3ccc(C(O)(C(F)(F)F)C(F)(F)F)cc3)CC2)cc1)N1CCCCC1]

MS (ESI) m/z 558.2 [M+H]+

6N: 1-(4-((1-(4-(1,1,1,3,3,3-Hexafluoro-2-hydroxypropan-2-yl)benzyl)piperidin-4-yl)methyl)phenyl)-3-(1-methyl-6-oxopiperidin-3-yl)urea

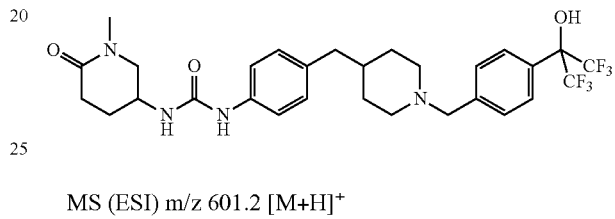

MS (ESI) m/z 601.2 [M+H]+

6O: 1-(4-((1-(4-(1,1,1,3,3,3-Hexafluoro-2-hydroxypropan-2-yl)benzyl)piperidin-4-yl)methyl)phenyl)-3-((3-methyloxetan-3-yl)methyl)urea

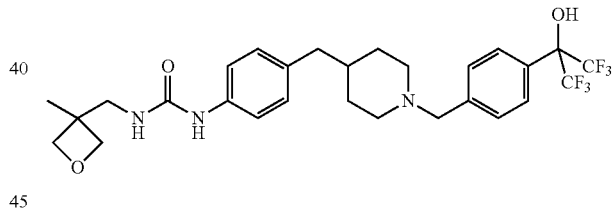

MS (ESI) m/z 574.2 [M+H]+

6P: 1-(4-((1-(4-(1,1,1,3,3,3-Hexafluoro-2-hydroxypropan-2-yl)benzyl)piperidin-4-yl)methyl)phenyl)-3-(oxetan-3-yl)urea

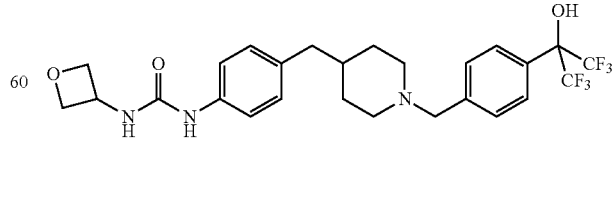

MS (ESI) m/z 546.2 [M+H]+

6Q: 1-(Cyclopropylmethyl)-3-(4-((1-(4-(1,1,1,3,3,3-hexafluoro-2-hydroxypropan-2-yl)benzyl)piperidin-4-yl)methyl)phenyl)urea

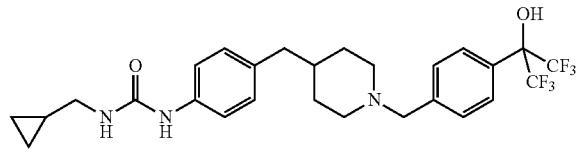 [SMILES: O=C(NCC1CC1)Nc1ccc(CC2CCN(Cc3ccc(C(O)(C(F)(F)F)C(F)(F)F)cc3)CC2)cc1]

MS (ESI) m/z 544.2 [M+H]$^+$

6U: 1-(4-((1-(4-(1,1,1,3,3,3-Hexafluoro-2-hydroxypropan-2-yl)benzyl)piperidin-4-yl)methyl)phenyl)-3-(tetrahydrothiophen-3-yl)urea

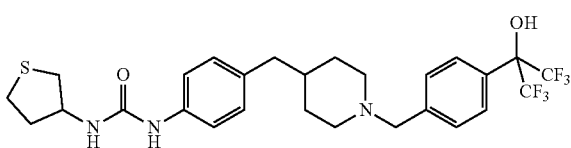

MS (ESI) m/z 576.2 [M+H]$^+$

6R: 1-(4-((1-(4-(1,1,1,3,3,3-Hexafluoro-2-hydroxypropan-2-yl)benzyl)piperidin-4-yl)methyl)phenyl)-3-(tetrahydro-2H-pyran-4-yl)urea

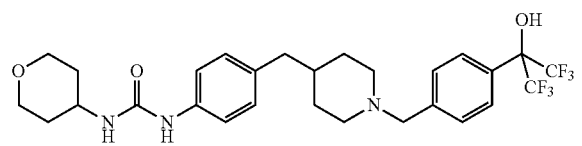 [SMILES: O=C(Nc1ccc(CC2CCN(Cc3ccc(C(O)(C(F)(F)F)C(F)(F)F)cc3)CC2)cc1)NC1CCOCC1]

MS (ESI) m/z 574.2 [M+H]$^+$

Example 7

1-(4-((1-(4-(1,1,1,3,3,3-Hexafluoro-2-hydroxypropan-2-yl)benzyl)piperidin-4-yl)methyl)phenyl)-3-(pyridin-4-yl)urea

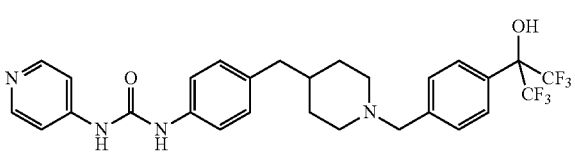

Phenyl pyridin-4-ylcarbamate (1.680 mmol, 0.36 g) was added to a stirred solution of 2-(4-((4-(4-aminobenzyl)piperidin-1-yl)methyl)phenyl)-1,1,1,3,3,3-hexafluoropropan-2-ol (1.120 mmol, 0.5 g) in dioxane (20 mL) and the mixture heated in a microwave for 10 minutes at 130° C. followed by 5 minutes at 130° C. The mixture was washed with water (10 mL) and the organic phase dried over magnesium sulfate, filtered and concentrated under reduced pressure. The resulting residue was purified by HPLC and concentrated under reduced pressure to afford the title compound (168 mg). MS (ESI) m/z 567.5 [M+H]$^+$ The following compounds were prepared in a similar manner:

6S: 1-(3-Fluoropyridin-4-yl)-3-(4-((1-(4-(1,1,1,3,3,3-hexafluoro-2-hydroxypropan-2-yl)benzyl)piperidin-4-yl)methyl)phenyl)urea

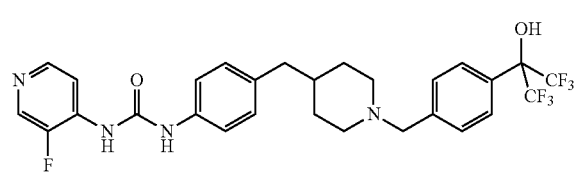 [SMILES: O=C(Nc1ccc(CC2CCN(Cc3ccc(C(O)(C(F)(F)F)C(F)(F)F)cc3)CC2)cc1)Nc1ccncc1F]

MS (ESI) m/z 585.2 [M+H]$^+$

6T: 1-(4-((1-(4-(1,1,1,3,3,3-Hexafluoro-2-hydroxypropan-2-yl)benzyl)piperidin-4-yl)methyl)phenyl)-3-(2-hydroxy-2-methylpropyl)urea

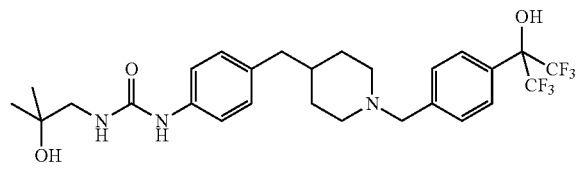

MS (ESI) m/z 562.2 [M+H]$^+$

7B: 1-(4-((1-(4-(1,1,1,3,3,3-Hexafluoro-2-hydroxypropan-2-yl)benzyl)piperidin-4-yl)methyl)phenyl)-3-(pyrimidin-4-yl)urea

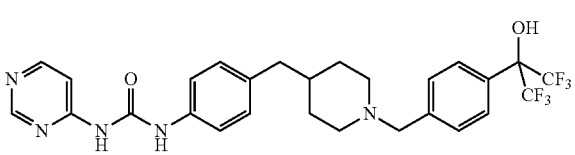 [SMILES: O=C(Nc1ccc(CC2CCN(Cc3ccc(C(O)(C(F)(F)F)C(F)(F)F)cc3)CC2)cc1)Nc1ccncn1]

MS (ESI) m/z 568.2 [M+H]$^+$

7C: 1-(4-((1-(4-(1,1,1,3,3,3-Hexafluoro-2-hydroxypropan-2-yl)benzyl)piperidin-4-yl)methyl)phenyl)-3-(pyridazin-4-yl)urea

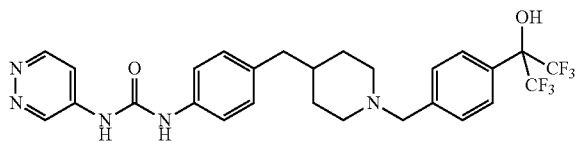 [SMILES: O=C(Nc1ccc(CC2CCN(Cc3ccc(C(O)(C(F)(F)F)C(F)(F)F)cc3)CC2)cc1)Nc1ccnnc1]

MS (ESI) m/z 568.2 [M+H]$^+$

Example 8

1-(4-((1-(4-(1,1,1,3,3,3-Hexafluoro-2-hydroxypropan-2-yl)benzyl)piperidin-4-yl)methyl)phenyl)-3-(1-oxo-tetrahydro-thiophen-3-yl)urea

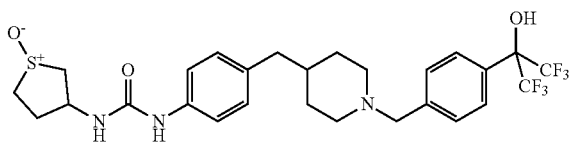 [SMILES: O=C(Nc1ccc(CC2CCN(Cc3ccc(C(O)(C(F)(F)F)C(F)(F)F)cc3)CC2)cc1)NC1CC[S+]([O-])C1]

To an ice-cooled solution of 1-(4-((1-(4-(1,1,1,3,3,3-hexafluoro-2-hydroxypropan-2-yl)benzyl)piperidin-4-yl)methyl)phenyl)-3-(tetrahydrothiophen-3-yl)urea (0.243 mmol, 140 mg) in dichloromethane was added 3-chloroperoxybenzoic acid (0.243 mmol, 54.5 mg) and the resulting mixture was stirred for 30 minutes. Additional 3-chloroperoxybenzoic acid (0.243 mmol, 54.5 mg) was added and reaction stirred for 1.5 hours. The reaction was concentrated under vacuum. The residue was purified by silica column chromatography (eluent: 2% methanol in dichloromethane-7% methanol in dichloromethane) and SCX chromatography to give the title compound (77.1 mg).

MS (ESI) m/z 592.0 [M+H]$^+$

Example 9

2-Amino-2-methylpropyl 4-((1-(4-(1,1,1,3,3,3-hexafluoro-2-hydroxypropan-2-yl)benzyl)piperidin-4-yl)methyl)phenylcarbamate

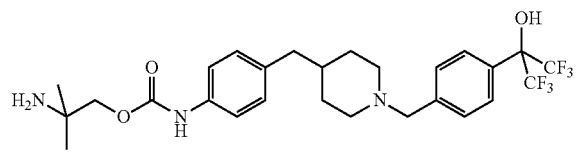 [SMILES: CC(C)(N)COC(=O)Nc1ccc(CC2CCN(Cc3ccc(C(O)(C(F)(F)F)C(F)(F)F)cc3)CC2)cc1]

2-(4-((4-(4-Aminobenzyl)piperidin-1-yl)methyl)phenyl)-1,1,1,3,3,3-hexafluoropropan-2-ol (0.448 mmol, 200 mg) and 4-nitrophenyl carbonochloridate (0.448 mmol, 90 mg) were combined and stirred in dichloromethane at room temperature for 30 minutes. 2-Amino-2-methylpropan-1-ol (0.896 mmol, 114 µl, 80 mg) was added and the reaction stirred at room temperature overnight. The reaction mixture was concentrated and purified by basic prep-HPLC to give the title compound (94.7 mg).

MS (ESI) m/z 562.2 [M+H]$^+$

Example 10

N-(4-((1-(4-(1,1,1,3,3,3-Hexafluoro-2-hydroxypropan-2-yl)benzyl)piperidin-4-yl)methyl)phenyl)-2-phenylacetamide

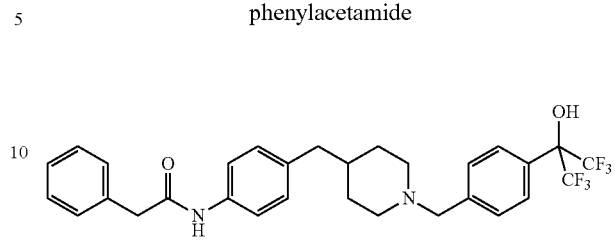

2-(4-((4-(4-Aminobenzyl)piperidin-1-yl)methyl)phenyl)-1,1,1,3,3,3-hexafluoropropan-2-ol (0.336 mmol, 150 mg) and 2-phenylacetyl chloride (0.504 mmol, 0.067 mL, 78 mg) were combined in dichloromethane (3 mL) and cooled to 0° C. Triethylamine (0.672 mmol, 0.093 mL, 68.0 mg) was added and the mixture allowed to stir at 0° C. for 2 hours before allowing to warm to room temperature and stirring overnight. The reaction was diluted with dichloromethane and washed with water. The mixture was filtered through a hydrophobic frit and concentrated under vacuum. The residue was purified by flash chromatography on silica gel (eluent: dichloromethane-10% methanol/dichloromethane gradient) to afford the title compound (124.4 mg).

MS (ESI) m/z 565.2 [M+H]$^+$

The following compound was prepared in a similar manner:

10B: 2-Cyclopentyl-N-(4-((1-(4-(1,1,1,3,3,3-hexafluoro-2-hydroxypropan-2-yl)benzyl)piperidin-4-yl)methyl)phenyl)acetamide

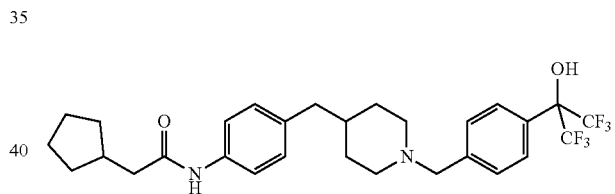

MS (ESI) m/z 557.2 [M+H]$^+$

Example 11

1-(4-((1-(4-(1,1,1,3,3,3-Hexafluoro-2-hydroxypropan-2-yl)benzyl)piperidin-4-ylidene)methyl)phenyl)-3-(2-hydroxy-2-methylpropyl)urea

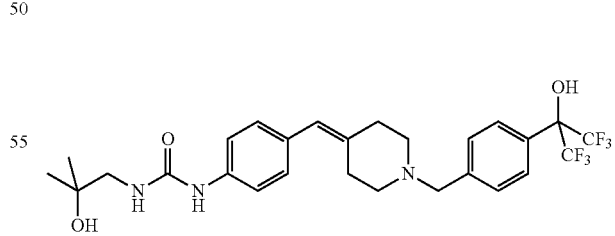

A: 4-(Piperidin-4-ylidenemethyl)aniline

Step 1: tert-Butyl 4-(3-fluoro-4-nitrobenzylidene)piperidine-1-carboxylate (2.97 mmol, 1 g), iron(II) sulfate heptahydrate (20.42 mmol, 5.68 g) and ammonia (10.02 mmol, 11.39 ml) were combined in ethanol (20 mL) and heated at 85° C. overnight. The reaction mixture was diluted with dichloromethane and water then filtered through celite. The organic phase of the filtrate was dried and concentrated under reduced pressure. The resulting residue was purified by silica gel column chromatography (eluting with dichloromethane to 3% methanol/dichloromethane) to afford the intermediate tert-butyl 4-(4-aminobenzylidene)piperidine-1-carboxylate (600 mg).

Step 2: A solution of tert-butyl 4-(4-aminobenzylidene)piperidine-1-carboxylate (20.22 mmol, 5.83 g) in dichloromethane (60 mL) was stirred with 2,2,2-trifluoroacetic acid (20.22 mmol, 2.305 g) at room temperature for 18 hours. The mixture was concentrated under reduced pressure and the resulting residue dissolved in dichloromethane (200 mL). The mixture was washed with water (75 mL) and the organic phase separated. The aqueous phase was basified with 4M sodium hydroxide solution, and extracted with dichloromethane (200 mL). The organic phase was dried over magnesium sulfate, filtered and concentrated under reduced pressure to afford the title compound (3.12 g). MS (ESI) m/z 189.6 [M+H]$^+$ B: 1-(4-((1-(4-(1,1,1,3,3,3-Hexafluoro-2-hydroxypropan-2-yl)benzyl)piperidin-4-ylidene)methyl)phenyl)-3-(2-hydroxy-2-methylpropyl)urea Step 1: 2-(4-(Bromomethyl)phenyl)-1,1,1,3,3,3-hexafluoropropan-2-ol (16.57 mmol, 5.59 g), 4-(piperidin-4-ylidenemethyl) (16.57 mmol, 3.12 g) and potassium carbonate (138.21 mmol, 2.75 g) were combined in acetonitrile (60 mL) and the mixture stirred at room temperature for 2.5 hours. The mixture was filtered, washed with dichloromethane (100 mL) and the filtrate concentrated under reduced pressure. The resulting residue was purified by silica gel column chromatography (eluting with dichloromethane to 4% methanol/dichloromethane) to afford the intermediate 2-(4-((4-(4-aminobenzylidene)piperidin-1-yl)methyl)phenyl)-1,1,1,3,3,3-hexafluoropropan-2-ol (4.98 g).

Step 2: 4-Nitrophenyl carbonochloridate (0.225 mmol, 45.4 mg) was added to a stirred solution of 2-(4-((4-(4-aminobenzylidene)piperidin-1-yl)methyl)phenyl)-1,1,1,3,3,3-hexafluoropropan-2-ol (0.225 mmol, 100 mg) in dioxane (1 mL) and the mixture stirred at room temperature for 1 hour. 1-Amino-2-methylpropan-2-ol (0.675 mmol, 60.2 mg) was added and the mixture stirred at room temperature for 1.5 hours. The mixture was washed with water (1 mL), the organic phase dried over magnesium sulfate, filtered and concentrated under reduced pressure. The resulting residue was purified by HPLC and treated with strong cation exchange column to afford the title compound (17 mg). MS (ESI) m/z 560.2 [M+H]$^+$ Example 12

1-(2-Amino-2-methylpropyl)-3-(2-fluoro-4-((1-(4-(1,1,1,3,3,3-hexafluoro-2-hydroxypropan-2-yl)benzyl)piperidin-4-yl)methyl)phenyl)urea

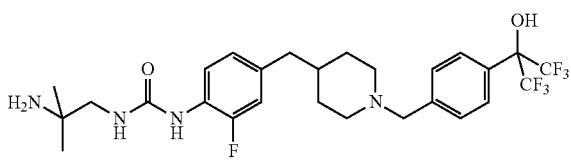 [SMILES: CC(C)(N)CNC(=O)Nc1ccc(CC2CCN(Cc3ccc(C(O)(C(F)(F)F)C(F)(F)F)cc3)CC2)cc1F]

A: Diethyl 3-fluoro-4-nitrobenzylphosphonate 4-(Bromomethyl)-2-fluoro-1-nitrobenzene (34.72 g, 148 mmol) and triethyl phosphite (25.8 mL) were heated at 140° C. for 4 hours. Water was added and the mixture was extracted with diethyl ether. The organics were dried with magnesium sulphate, filtered and evaporated under reduced pressure to afford the title compound (40.94 g). $^1$H NMR (CDCl$_3$, 400 MHz): δ 8.03 (t, 1H), 7.24 (s, 1H) 7.21 (s, 1H) 4.08 (m, 4H), 3.20 (d, 2H), 1.27 (m, 6H)

B: tert-Butyl 4-(3-fluoro-4-nitrobenzylidene)piperidine-1-carboxylate tert-Butyl 4-oxopiperidine-1-carboxylate (126 mmol, 25.04 g) and diethyl 3-fluoro-4-nitrobenzylphosphonate (126 mmol, 36.6 g) in tetrahydrofuran (220 mL) were stirred and sodium hydride (163 mmol, 6.54 g, 60% in oil) was added. The reaction was stirred for 4 hours and then water was added. The reaction was extracted with dichloromethane and the organics were dried (magnesium sulfate), filtered and concentrated under reduced pressure. The residue was purified by silica column chromatography eluting with dichloromethane to give a bright yellow solid. This solid was filtered, washed with heptane and vacuum dried to afford the title compound (27.47 g). $^1$H NMR (CDCl$_3$, 400 MHz): δ 8.1 (t, 1H), 7.1 (s, 1H), 7.05 (s, 1H), 6.35 (s, 1H), 3.55 (m, 2H), 3.45 (m, 2H), 2.52 (m, 2H), 2.4 (m, 2H), 1.49 (s, 9H)

C: 2-(4-((4-(4-Amino-3-fluorobenzyl)piperidin-1-yl)methyl)phenyl)-1,1,1,3,3,3-hexafluoropropan-2-ol Step 1: A flask was charged with palladium (II)acetate (1.486 mmol, 0.334 g), tert-butyl 4-(3-fluoro-4-nitrobenzylidene)piperidine-1-carboxylate (29.7 mmol, 10 g) and tetrahydrofuran (15 mL) and sealed and purged with nitrogen. A solution of potassium fluoride (59.5 mmol, 3.45 g, in 50 ml water) was added via a syringe. Polymethylhydrosiloxane (119 mmol, 7.13 mL) was added dropwise (caution, gas evolution) and the reaction stirred at room temperature for 1 hour. Diethyl ether (10 mL) was added to the reaction mixture. After 5 minutes of stirring the reaction mixture was filtered through celite and diluted with water and ethyl acetate. The organic layer was washed with water and brine, dried over magnesium sulfate and concentrated under vacuum. The residue was purified by silica column chromatography (eluent: 20%-50% ethyl acetate in heptane) to give the intermediate tert-butyl 4-(4-amino-3-fluorobenzyl)piperidine-1-carboxylate (9.23 g).

Step 2: Tert-butyl 4-(4-amino-3-fluorobenzyl)piperidine-1-carboxylate (6.49 mmol, 2 g) was dissolved in dichloromethane (5 mL). Trifluoroacetic acid (3 mL) was added and the reaction mixture stirred at room temperature for 30 minutes. The reaction mixture was purified by SCX chromatography to give the intermediate 2-fluoro-4-(piperidin-4-ylmethyl)aniline (1.6 g) as a colourless oil.

Step 3: 2-Fluoro-4-(piperidin-4-ylmethyl)aniline (7.68 mmol, 1.6 g), 2-(4-(bromomethyl)phenyl)-1,1,1,3,3,3-hexafluoropropan-2-ol (7.68 mmol, 2.59 g) and potassium carbonate (15.36 mmol, 2.123 g) were combined and stirred at room temperature in acetonitrile (20 mL) for 2 hours. The reaction mixture was filtered and the filtrate concentrated under vacuum. The residue was purified by column chromatography (eluent: dichloromethane-7% methanol in dichloromethane) to give the title compound (800 mg). MS (ESI) m/z 465.2 [M+H]$^+$ D: 1-(2-Amino-2-methylpropyl)-3-(2-fluoro-4-((1-(4-(1,1,1,3,3,3-hexafluoro-2-hydroxypropan-2-yl)benzyl)piperidin-4-yl)methyl)phenyl)urea A solution of 2-(4-((4-(4-amino-3-fluorobenzyl)piperidin-1-yl)methyl)phenyl)-1,1,1,3,3,3-hexafluoropropan-2-ol (0.861 mmol, 0.4 g) and 4-nitrophenyl carbonochloridate (0.861 mmol, 0.174 g) in tetrahydrofuran (5 mL) was stirred at room temperature for 30 minutes. 2-Methylpropane-1,2-diamine (1.723 mmol, 0.152 g) was added, followed by triethylamine (2.58 mmol, 0.360 mL, 0.261 g) and the reaction stirred at room temperature overnight. The reaction mixture was concentrated under vacuum. The residue was purified by prep-HPLC (acidic conditions) and SCX chromatography to afford the title compound (45.3 mg). MS (ESI) m/z 579.2 [M+H]+

The following compounds were prepared in a similar manner:

12B: 1-(2-Fluoro-4-((1-(4-(1,1,1,3,3,3-hexafluoro-2-hydroxypropan-2-yl)benzyl)piperidin-4-yl)methyl)phenyl)-3-((1S,2R)-2-hydroxycyclopentyl)urea

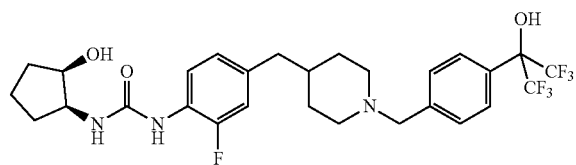 [SMILES: O=C(Nc1ccc(CC2CCN(Cc3ccc(C(O)(C(F)(F)F)C(F)(F)F)cc3)CC2)cc1F)N[C@H]1CCC[C@H]1O]

MS (ESI) m/z 592.2 [M+H]+

12C: 1-(2-Fluoro-4-((1-(4-(1,1,1,3,3,3-hexafluoro-2-hydroxypropan-2-yl)benzyl)piperidin-4-yl)methyl)phenyl)-3-((1S,2R)-2-hydroxycyclohexyl)urea

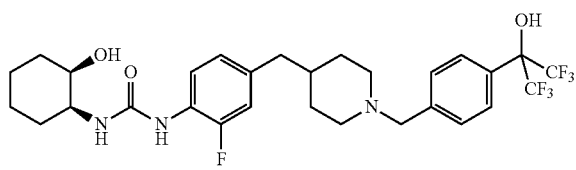 [SMILES: O=C(Nc1ccc(CC2CCN(Cc3ccc(C(O)(C(F)(F)F)C(F)(F)F)cc3)CC2)cc1F)N[C@H]1CCCC[C@H]1O]

MS (ESI) m/z 606.2 [M+H]+

12D: 1-(2-Fluoro-4-((1-(4-(1,1,1,3,3,3-hexafluoro-2-hydroxypropan-2-yl)benzyl)piperidin-4-yl)methyl)phenyl)-3-(isoxazol-4-yl)urea

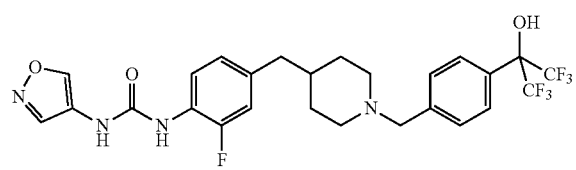 [SMILES: O=C(Nc1cnoc1)Nc1ccc(CC2CCN(Cc3ccc(C(O)(C(F)(F)F)C(F)(F)F)cc3)CC2)cc1F]

MS (ESI) m/z 575.2 [M+H]+

12E: 1-(2-Fluoro-4-((1-(4-(1,1,1,3,3,3-hexafluoro-2-hydroxypropan-2-yl)benzyl)piperidin-4-yl)methyl)phenyl)-3-(5-methylisoxazol-3-yl)urea

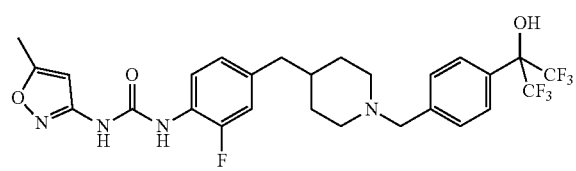 [SMILES: Cc1cc(NC(=O)Nc2ccc(CC3CCN(Cc4ccc(C(O)(C(F)(F)F)C(F)(F)F)cc4)CC3)cc2F)no1]

MS (ESI) m/z 589.2 [M+H]+

12F: (S)-1-(2-Fluoro-4-((1-(4-(1,1,1,3,3,3-hexafluoro-2-hydroxypropan-2-yl)benzyl)piperidin-4-yl)methyl)phenyl)-3-(tetrahydrofuran-3-yl)urea

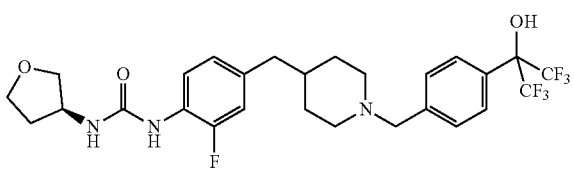 [SMILES: O=C(Nc1ccc(CC2CCN(Cc3ccc(C(O)(C(F)(F)F)C(F)(F)F)cc3)CC2)cc1F)N[C@H]1CCOC1]

MS (ESI) m/z 578.2 [M+H]+

12G: 1-(1,1-Dioxo-tetrahydro-1$\lambda^6$-thiophen-3-yl)-3-(2-fluoro-4-((1-(4-(1,1,1,3,3,3-hexafluoro-2-hydroxypropan-2-yl)benzyl)piperidin-4-yl)methyl)phenyl)urea

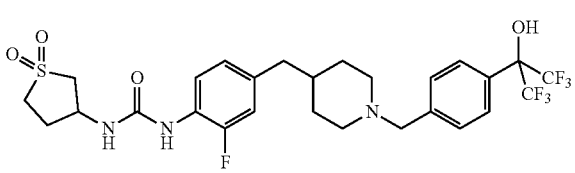 [SMILES: O=C(Nc1ccc(CC2CCN(Cc3ccc(C(O)(C(F)(F)F)C(F)(F)F)cc3)CC2)cc1F)NC1CCS(=O)(=O)C1]

MS (ESI) m/z 626.2 [M+H]+

12H: 1-(2-Fluoro-4-((1-(4-(1,1,1,3,3,3-hexafluoro-2-hydroxypropan-2-yl)benzyl)piperidin-4-yl)methyl)phenyl)-3-((4-hydroxytetrahydro-2H-pyran-4-yl)methyl)urea

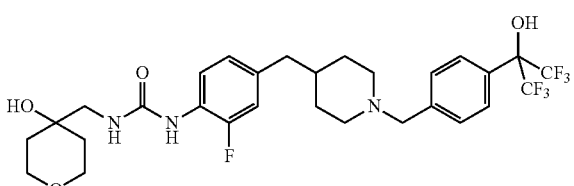

MS (ESI) m/z 622.2 [M+H]+

12I: 1-(2-Fluoro-4-((1-(4-(1,1,1,3,3,3-hexafluoro-2-hydroxypropan-2-yl)benzyl)piperidin-4-yl)methyl)phenyl)-3-(3,3,3-trifluoro-2-hydroxypropyl)urea

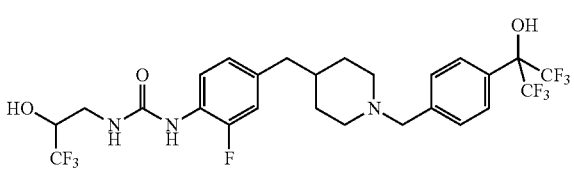 [SMILES: O=C(NCC(O)C(F)(F)F)Nc1ccc(CC2CCN(Cc3ccc(C(O)(C(F)(F)F)C(F)(F)F)cc3)CC2)cc1F]

MS (ESI) m/z 620.2 [M+H]+

12J: 1-(2-Fluoro-4-((1-(4-(1,1,1,3,3,3-hexafluoro-2-hydroxypropan-2-yl)benzyl)piperidin-4-yl)methyl)phenyl)-3-((1-hydroxycyclobutyl)methyl)urea

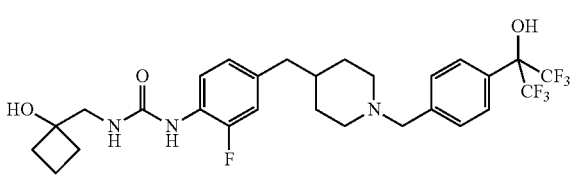 [SMILES: O=C(NCC1(O)CCC1)Nc1ccc(CC2CCN(Cc3ccc(C(O)(C(F)(F)F)C(F)(F)F)cc3)CC2)cc1F]

MS (ESI) m/z 592.2 [M+H]+

12K: 1-(2-Fluoro-4-((1-(4-(1,1,1,3,3,3-hexafluoro-2-hydroxypropan-2-yl)benzyl)piperidin-4-yl)methyl)phenyl)-3-((1r,4r)-4-hydroxycyclohexyl)urea

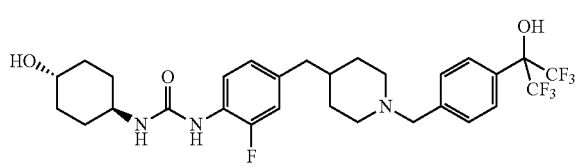 [SMILES: O=C(Nc1ccc(CC2CCN(Cc3ccc(C(O)(C(F)(F)F)C(F)(F)F)cc3)CC2)cc1F)N[C@H]1CC[C@H](O)CC1]

MS (ESI) m/z 606.2 [M+H]$^+$

12L: 1-(2-Fluoro-4-((1-(4-(1,1,1,3,3,3-hexafluoro-2-hydroxypropan-2-yl)benzyl)piperidin-4-yl)methyl)phenyl)-3-((1s,4s)-4-hydroxycyclohexyl)urea

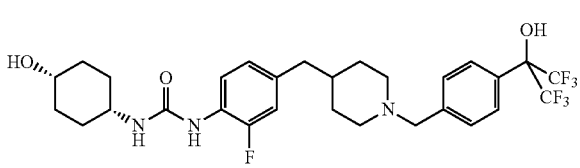 [SMILES: O=C(Nc1ccc(CC2CCN(Cc3ccc(C(O)(C(F)(F)F)C(F)(F)F)cc3)CC2)cc1F)N[C@H]1CC[C@@H](O)CC1]

MS (ESI) m/z 606.2 [M+H]$^+$

12M: 1-(2-Fluoro-4-((1-(4-(1,1,1,3,3,3-hexafluoro-2-hydroxypropan-2-yl)benzyl)piperidin-4-yl)methyl)phenyl)-3-((1-hydroxycyclopropyl)methyl)urea

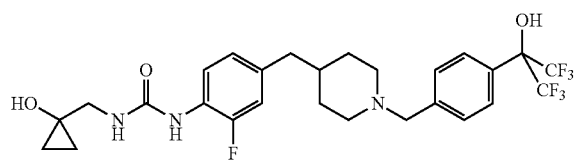 [SMILES: O=C(NCC1(O)CC1)Nc1ccc(CC2CCN(Cc3ccc(C(O)(C(F)(F)F)C(F)(F)F)cc3)CC2)cc1F]

MS (ESI) m/z 578.2 [M+H]$^+$

12N: 3-(3-(2-Fluoro-4-((1-(4-(1,1,1,3,3,3-hexafluoro-2-hydroxypropan-2-yl)benzyl)piperidin-4-yl)methyl)phenyl)ureido)-2,2-dimethylpropanamide

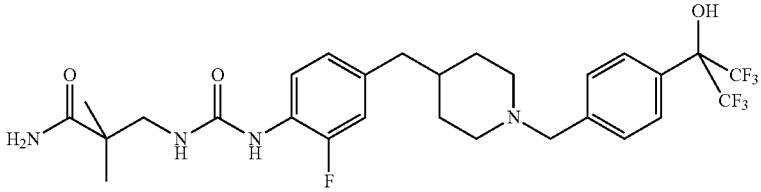 [SMILES: CC(C)(CNC(=O)Nc1ccc(CC2CCN(Cc3ccc(C(O)(C(F)(F)F)C(F)(F)F)cc3)CC2)cc1F)C(N)=O]

MS (ESI) m/z 607.2 [M+H]$^+$

12O: 1-(2-Fluoro-4-((1-(4-(1,1,1,3,3,3-hexafluoro-2-hydroxypropan-2-yl)benzyl)piperidin-4-yl)methyl)phenyl)-3-(3-hydroxy-3-methylbutyl)urea

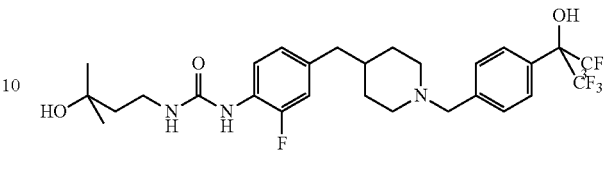

MS (ESI) m/z 594.2 [M+H]$^+$

12P: (R)-1-(2-Fluoro-4-((1-(4-(1,1,1,3,3,3-hexafluoro-2-hydroxypropan-2-yl)benzyl)piperidin-4-yl)methyl)phenyl)-3-(tetrahydrofuran-3-yl)urea

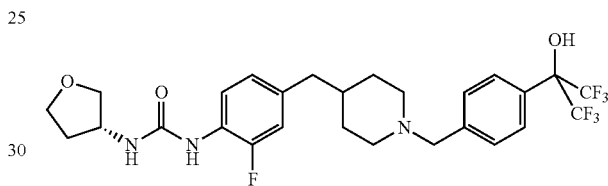

MS (ESI) m/z 578.2 [M+H]$^+$

12Q: 1-((1-Aminocyclopentyl)methyl)-3-(2-fluoro-4-((1-(4-(1,1,1,3,3,3-hexafluoro-2-hydroxypropan-2-yl)benzyl)piperidin-4-yl)methyl)phenyl)urea

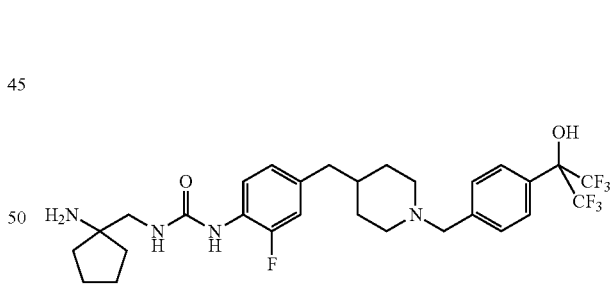

MS (ESI) m/z 605.2 [M+H]$^+$

12R: 1-((1-Aminocyclopropyl)methyl)-3-(2-fluoro-4-((1-(4-(1,1,1,3,3,3-hexafluoro-2-hydroxypropan-2-yl)benzyl)piperidin-4-yl)methyl)phenyl) urea

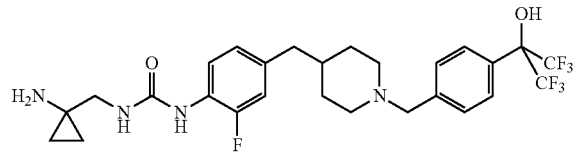 [SMILES: NC1(CNC(=O)Nc2ccc(CC3CCN(Cc4ccc(C(O)(C(F)(F)F)C(F)(F)F)cc4)CC3)cc2F)CC1]

MS (ESI) m/z 577.6 [M+H]⁺

12S: 1-((1-Aminocyclobutyl)methyl)-3-(2-fluoro-4-((1-(4-(1,1,1,3,3,3-hexafluoro-2-hydroxypropan-2-yl)benzyl)piperidin-4-yl)methyl)phenyl)urea

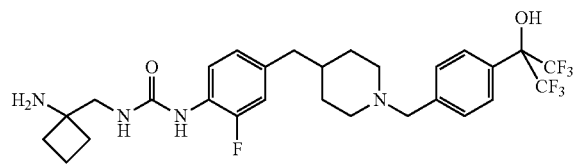 [SMILES: NC1(CNC(=O)Nc2ccc(CC3CCN(Cc4ccc(C(O)(C(F)(F)F)C(F)(F)F)cc4)CC3)cc2F)CCC1]

MS (ESI) m/z 591.2 [M+H]⁺

12T: 1-(2-Fluoro-4-((1-(4-(1,1,1,3,3,3-hexafluoro-2-hydroxypropan-2-yl)benzyl)piperidin-4-yl)methyl)phenyl)-3-(4-hydroxytetrahydrofuran-3-yl)urea, trans racemate

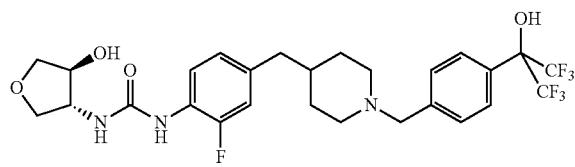 [SMILES: O=C(Nc1ccc(CC2CCN(Cc3ccc(C(O)(C(F)(F)F)C(F)(F)F)cc3)CC2)cc1F)N[C@@H]1COC[C@H]1O]

MS (ESI) m/z 594.2 [M+H]⁺

12U: 1-(2-Fluoro-4-((1-(4-(1,1,1,3,3,3-hexafluoro-2-hydroxypropan-2-yl)benzyl)piperidin-4-yl)methyl)phenyl)-3-(2-hydroxypropyl)urea

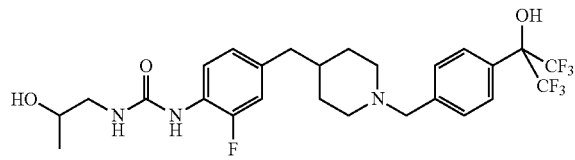 [SMILES: CC(O)CNC(=O)Nc1ccc(CC2CCN(Cc3ccc(C(O)(C(F)(F)F)C(F)(F)F)cc3)CC2)cc1F]

MS (ESI) m/z 566.3 [M+H]⁺

12V: 1-(2-Fluoro-4-((1-(4-(1,1,1,3,3,3-hexafluoro-2-hydroxypropan-2-yl)benzyl)piperidin-4-yl)methyl)phenyl)-3-(2-methyl-2-(methylamino)propyl)urea

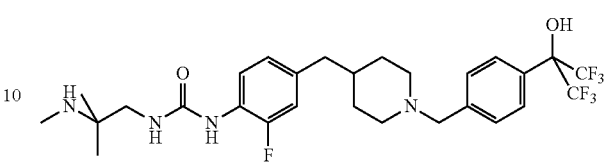

MS (ESI) m/z 593.2 [M+H]⁺

12W: 1-(2-Amino-2-cyclopropylpropyl)-3-(2-fluoro-4-((1-(4-(1,1,1,3,3,3-hexafluoro-2-hydroxypropan-2-yl)benzyl)piperidin-4-yl)methyl)phenyl)urea

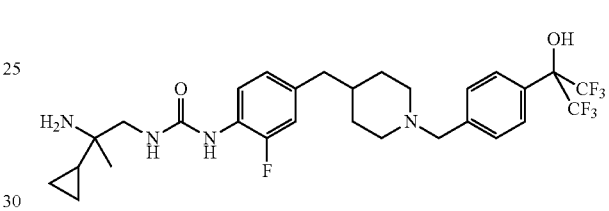

MS (ESI) m/z 605.7 [M+H]⁺

12X: 1-(2-Amino-2,3-dimethylbutyl)-3-(2-fluoro-4-((1-(4-(1,1,1,3,3,3-hexafluoro-2-hydroxypropan-2-yl)benzyl)piperidin-4-yl)methyl)phenyl)urea

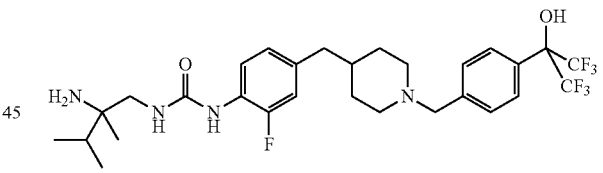

MS (ESI) m/z 607.9 [M+H]⁺

12Y: 1-(2-Amino-3,3,3-trifluoro-2-methylpropyl)-3-(2-fluoro-4-((1-(4-(1,1,1,3,3,3-hexafluoro-2-hydroxypropan-2-yl)benzyl)piperidin-4-yl)methyl)phenyl)urea

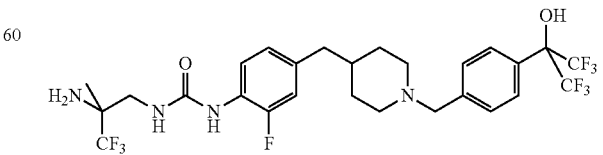

MS (ESI) m/z 633.9 [M+H]⁺

12Z: 1-(2-(Dimethylamino)-2-methylpropyl)-3-(2-fluoro-4-((1-(4-(1,1,1,3,3,3-hexafluoro-2-hydroxypropan-2-yl)benzyl)piperidin-4-yl)methyl)phenyl)urea

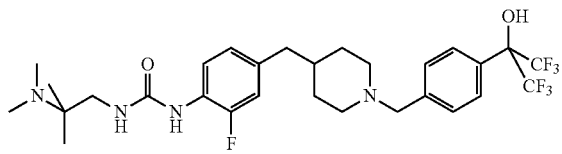 [SMILES: CN(C)C(C)(C)CNC(=O)Nc1ccc(CC2CCN(Cc3ccc(C(O)(C(F)(F)F)C(F)(F)F)cc3)CC2)cc1F]

MS (ESI) m/z 607.2 [M+H]⁺

12AA: 1-(2-Fluoro-4-((1-(4-(1,1,1,3,3,3-hexafluoro-2-hydroxypropan-2-yl)benzyl)piperidin-4-yl)methyl)phenyl)-3-(3,3,3-trifluoro-2-hydroxy-2-methylpropyl)urea

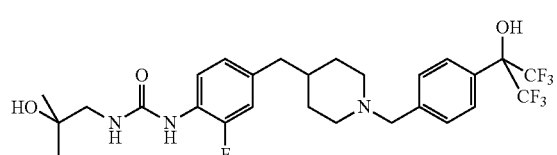

MS (ESI) m/z 634.2 [M+H]⁺

12AB: 1-(2-Fluoro-4-((1-(4-(1,1,1,3,3,3-hexafluoro-2-hydroxypropan-2-yl)benzyl)piperidin-4-yl)methyl)phenyl)-3-(2-hydroxy-2-phenylethyl)urea

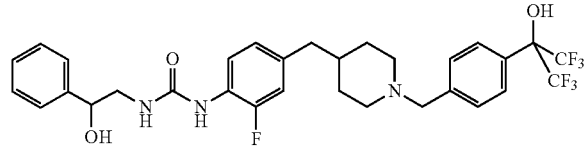 [SMILES: O=C(NCC(O)c1ccccc1)Nc1ccc(CC2CCN(Cc3ccc(C(O)(C(F)(F)F)C(F)(F)F)cc3)CC2)cc1F]

MS (ESI) m/z 628.2 [M+H]⁺

12AC: 1-(2-Fluoro-4-((1-(4-(1,1,1,3,3,3-hexafluoro-2-hydroxypropan-2-yl)benzyl)piperidin-4-yl)methyl)phenyl)-3-(2-hydroxy-2-methylpropyl)urea

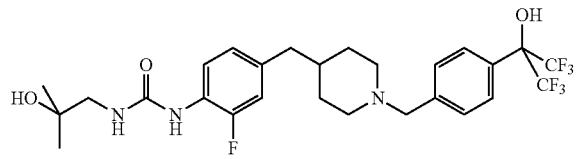 [SMILES: CC(C)(O)CNC(=O)Nc1ccc(CC2CCN(Cc3ccc(C(O)(C(F)(F)F)C(F)(F)F)cc3)CC2)cc1F]

MS (ESI) m/z 580.5 [M+H]⁺

12AD: 1-(2-Fluoro-4-((1-(4-(1,1,1,3,3,3-hexafluoro-2-hydroxypropan-2-yl)benzyl)piperidin-4-yl)methyl)phenyl)-3-((1R,3R)-3-hydroxycyclopentyl)urea

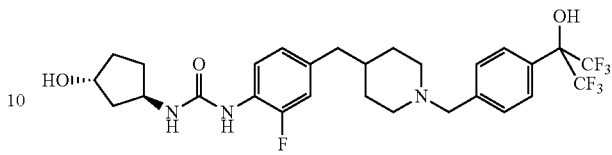

MS (ESI) m/z 592.2 [M+H]⁺

12AE: 1-(2-Fluoro-4-((1-(4-(1,1,1,3,3,3-hexafluoro-2-hydroxypropan-2-yl)benzyl)piperidin-4-yl)methyl)phenyl)-3-(oxetan-3-yl)urea

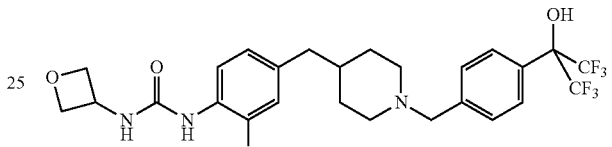

MS (ESI) m/z 564.2 [M+H]⁺

12AF: 1-((3-Aminooxetan-3-yl)methyl)-3-(2-fluoro-4-((1-(4-(1,1,1,3,3,3-hexafluoro-2-hydroxypropan-2-yl)benzyl)piperidin-4-yl)methyl)phenyl)urea

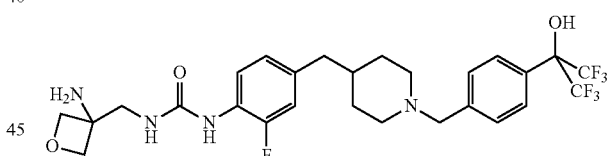

MS (ESI) m/z 593.2 [M+H]⁺

12AG: 1-(2-Fluoro-4-((1-(4-(1,1,1,3,3,3-hexafluoro-2-hydroxypropan-2-yl)benzyl)piperidin-4-yl)methyl)phenyl)-3-(tetrahydro-2H-pyran-4-yl)urea

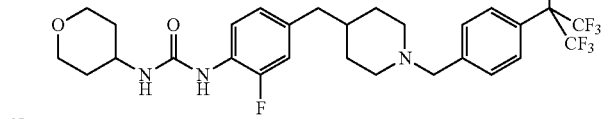

MS (ESI) m/z 592.2 [M+H]⁺

Example 13

1-(2-Fluoro-4-((1-(4-(1,1,1,3,3,3-hexafluoro-2-hydroxypropan-2-yl)benzyl)piperidin-4-yl)methyl)phenyl)-3-(pyridin-4-yl)urea

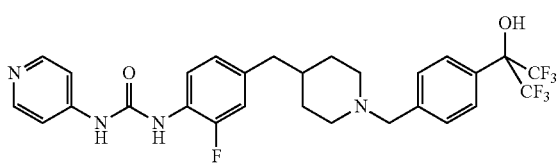

Phenyl pyridin-4-ylcarbamate (1.933 mmol, 0.414 g) was added to a stirred solution of 2-(4-((4-(4-amino-3-fluorobenzyl)piperidin-1-yl)methyl)phenyl)-1,1,1,3,3,3-hexafluoropropan-2-ol (1.292 mmol, 0.6 g) in dioxane (6 mL) and the mixture heated in a microwave for 10 minutes at 130° C. The mixture was washed with water (10 mL) and the organic phase dried over magnesium sulfate, filtered and concentrated under reduced pressure. The resulting residue was purified by silica gel column chromatography (eluting with 1% to 10% methanol/dichloromethane) to afford the title compound (271 mg). MS (ESI) m/z 585.3 [M+H]$^+$ The following compound was prepared in a similar manner:

13B: 1-(2-Fluoro-4-((1-(4-(1,1,1,3,3,3-hexafluoro-2-hydroxypropan-2-yl)benzyl)piperidin-4-yl)methyl)phenyl)-3-(pyrimidin-4-yl)urea

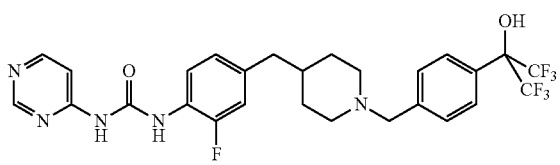 [SMILES: O=C(Nc1ccncn1)Nc1ccc(CC2CCN(Cc3ccc(C(O)(C(F)(F)F)C(F)(F)F)cc3)CC2)cc1F]

MS (ESI) m/z 586.2 [M+H]$^+$

Example 14

1-(2-Amino-2-methylpropyl)-3-(2-fluoro-4-((1-(4-(1,1,1,3,3,3-hexafluoro-2-hydroxypropan-2-yl)-2-propylbenzyl)piperidin-4-yl)methyl)phenyl)urea

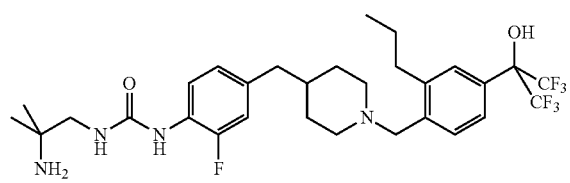 [SMILES: CCCc1cc(C(O)(C(F)(F)F)C(F)(F)F)ccc1CN1CCC(Cc2ccc(NC(=O)NCC(C)(C)N)c(F)c2)CC1]

A: 2-(4-Bromo-3-propyl)phenyl)-1,1,1,3,3,3-hexafluoropropan-2-ol 2-(4-Amino-3-propylphenyl)-1,1,1,3,3,3-hexafluoropropan-2-ol (33.2 mmol, 10 g) was dissolved in dioxane (15 mL) and water (30 mL) was added. The suspension was heated to reflux then hydrobromic acid (48% weight in water, 149 mmol, 17 mL) was added drop wise via an addition funnel over a 20 minute period. The mixture was heated for a further 20 minutes before cooling to 0° C. A solution of sodium nitrite (33.2 mmol, 2.290 g) in water (30 mL) was added to the mixture over a 30 minute period and the mixture stirred at 0° C. for 30 minutes. A solution of copper (I) bromide (38.2 mmol, 5.48 g) in water (30 mL) and hydrobromic acid (48% weight in water, 149 mmol, 17 mL) was added drop wise to the mixture over a 20 minute period at 0° C. and the mixture was allowed to stir at 0° C. for 20 minutes. The mixture was warmed to 60° C. for 20 minutes then allowed to stir at room temperature overnight. The reaction mixture was extracted with diethyl ether (3×100 mL), the organic phase was dried over magnesium sulfate, filtered and the filtrate was concentrated under vacuum. The resulting residue was purified by silica gel column chromatography (eluting with 10% ethyl acetate/90% heptane) to afford the title compound (6.1 g).

MS (ESI) m/z 365.5 [M−H]$^-$

B: 4-(1,1,1,3,3,3-Hexafluoro-2-hydroxypropan-2-yl)-2-propylbenzaldehyde

To a nitrogen purged 3-necked flask was added 2-(4-bromo-3-propylphenyl)-1,1,1,3,3,3-hexafluoropropan-2-ol (2.74 mmol, 1 g) in anhydrous tetrahydrofuran (15 mL). The solution was cooled to −78° C. before the addition of n-butyl lithium in hexane (2.5M, 8.22 mmol, 3.29 mL). The mixture was stirred at −78° C. for 15 minutes before the drop wise addition of N,N-dimethylformamide (3.01 mmol, 0.220 g). The mixture was stirred at −78° C. for 10 minutes and was then allowed to warm to room temperature and stir for 30 minutes. The mixture was quenched with water (10 mL) and diluted with ethyl acetate (100 mL). The organic phase was separated, washed with water (2×50 mL), dried over magnesium sulfate, filtered and the filtrate was concentrated under reduced pressure. The resulting residue was purified by silica gel column chromatography (eluting with 10% ethyl acetate/90% heptane) to afford the title compound (417 mg). MS (ESI) m/z 313.3 [M−H]$^-$

C: 1,1,1,3,3,3-Hexafluoro-2-(4-(hydroxymethyl)-3-propylphenyl)propan-2-ol 4-(1,1,1,3,3,3-Hexafluoro-2-hydroxypropan-2-yl)-2-propylbenzaldehyde (0.636 mmol, 200 mg) was dissolved in methanol (4 mL)/dichloromethane (1 mL) and sodium borohydride (1.909 mmol, 72.2 mg) was added. The mixture was stirred at room temperature for 90 minutes then was concentrated under reduced pressure. The residue was dissolved in dichloromethane (50 mL) and washed with a saturated solution of sodium bicarbonate (25 mL). The organic phase was filtered through a hydrophobic frit and concentrated to afford the title compound (161 mg).

MS (ESI) m/z 315.1 [M−H]$^-$

D: tert-Butyl 4-(4-(3-(2-amino-2-methylpropyl)ureido)-3-fluorobenzyl)piperidine-1-carboxylate tert-Butyl 4-(4-amino-3-fluorobenzyl)piperidine-1-carboxylate (3.44 mmol, 1.06 g) and 4-nitrophenyl chloroformate (3.44 mmol, 0.693 g) were combined in tetrahydrofuran (5 mL) and the reaction stirred at room temperature for 1 hour. 2-Methylpropane-1,2-diamine (3.44 mmol, 0.303 g) and triethylamine (10.31 mmol, 1.043 g) were added and the mixture stirred at room temperature overnight. The mixture was concentrated under reduced pressure and the resulting residue purified by silica gel column chromatography (eluting with dichloromethane to 20% methanol/dichloromethane) to afford the title compound (960 mg). MS (ESI) m/z 423.2 [M+H]+

E: 1-(2-Amino-2-methylpropyl)-3-(2-fluoro-4-(piperidin-4-ylmethyl)phenyl)urea tert-Butyl 4-(4-(3-(2-amino-2-methylpropyl)ureido)-3-fluorobenzyl)piperidine-1-carboxylate (2.272 mmol, 960 mg) was dissolved in dichloromethane (40 mL) and trifluoroacetic acid (45.4 mmol, 5181 mg) added. The mixture was stirred at room temperature for 3 hours before concentrating under reduced pressure. The resulting residue was purified by strong cation exchange column chromatography to afford the title compound (110 mg). MS (ESI) m/z 323.5 [M+H]+

F: 1-(2-Amino-2-methylpropyl)-3-(2-fluoro-4-((1-(4-(1,1,1,3,3,3-hexafluoro-2-hydroxypropan-2-yl)-2-propylbenzyl)piperidin-4-yl)methyl)phenyl)urea 1,1,1,3,3,3-Hexafluoro-2-(4-(hydroxymethyl)-3-propylphenyl)propan-2-ol (0.474 mmol, 150 mg) was dissolved in dichloromethane (5 mL) and triethylamine (1.423 mmol, 144 mg) added. The mixture was cooled to 0° C. before the addition of methanesulfonyl chloride (0.611 mmol, 70.0 mg). The mixture was stirred at 0° C. for 90 min. The reaction mixture was diluted with dichloromethane (50 mL) and washed with water (2×10 mL). The organic phase was dried over magnesium sulfate, filtered and the filtrate was concentrated under reduced pressure. The resulting residue was dissolved in acetonitrile (4 mL) and 1-(2-amino-2-methylpropyl)-3-(2-fluoro-4-(piperidin-4-ylmethyl)phenyl)urea (0.341 mmol, 110 mg) was added followed by potassium carbonate (1.023 mmol, 141 mg). The mixture was heated to reflux for 16 hours. The mixture was cooled, filtered and the filtrate was concentrated under reduced pressure. The resulting residue was purified by HPLC and treated with strong cation exchange column chromatography to afford the title compound (12 mg).
MS (ESI) m/z 621.2 [M+H]+

Example 15

1-(2-Amino-2-methylpropyl)-3-(5-chloro-2-fluoro-4-((1-(4-(1,1,1,3,3,3-hexafluoro-2-hydroxypropan-2-yl)benzyl)piperidin-4-yl)methyl)phenyl)urea

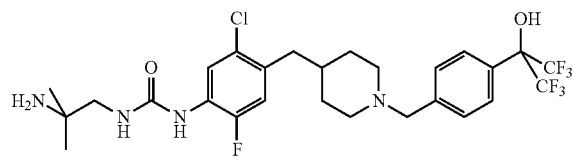 [SMILES: CC(C)(N)CNC(=O)Nc1cc(Cl)c(CC2CCN(Cc3ccc(C(O)(C(F)(F)F)C(F)(F)F)cc3)CC2)cc1F]

A: 1-Chloro-4-fluoro-2-methyl-5-nitrobenzene

To concentrated sulfuric acid (23.81 g), cooled to 0° C., under a nitrogen atmosphere, was added concentrated nitric acid (27.5 g) dropwise. 2-Chloro-5-fluorotoluene (9 g) was added dropwise and the reaction was stirred for 2 hours. The reaction was poured into ice and extracted with ethyl acetate. The organic phase was washed with aqueous sodium hydrogen carbonate, dried over sodium sulfate and concentrated under reduced pressure. The residue was purified by silica column chromatography [eluting with ethyl acetate/heptane (1:2)] to yield the title compound (9.4 g).
$^1$H NMR (CDCl$_3$, 400 MHz): δ 8.1 (d, 1H), 7.15 (d, 1H), 2.49 (s, 3H)

B: 1-(Bromomethyl)-2-chloro-5-fluoro-4-nitrobenzene

1-Chloro-4-fluoro-2-methyl-5-nitrobenzene (1 g) was dissolved in chlorobenzene (6 mL) and N-bromosuccinimide (1.408 g) was added followed by benzoyl peroxide (0.183 mg). The reaction mixture was stirred at reflux for 4 hours. The reaction mixture was cooled and water was added. The mixture was extracted with dichloromethane (3×) and concentrated under reduced pressure. The crude oil obtained was triturated with diethyl ether, filtered and the filtrate concentrated under reduced pressure (3×) to yield the title compound (1.55 g).
$^1$H NMR (CDCl$_3$, 400 MHz): δ 8.14 (d, 1H), 7.45 (d, 1H), 4.56 (d, 2H)

C: Diethyl 2-chloro-5-fluoro-4-nitrobenzylphosphonate 1-(Bromomethyl)-2-chloro-5-fluoro-4-nitrobenzene (6.7 g, 18.62 mmol) and triethyl phosphate (5.64 mL) were heated in an oil bath for 3 hours at 140° C. The reaction mixture was concentrated and chromatographed on silica eluting with dichloromethane/methanol (1:0-1%) to give the title compound (4.06 g).
$^1$H NMR (CDCl$_3$, 400 MHz): δ 8.13 (d, 1H), 7.43 (dd, 1H), 4.10 (m, 4H), 3.40 (d, 2H), 1.32 (m, 6H)

D: tert-Butyl 4-(2-chloro-5-fluoro-4-nitrobenzylidene)piperidine-1-carboxylate Diethyl 2-chloro-5-fluoro-4-nitrobenzylphosphonate (4.06 g, 12.47 mmol) and tert-butyl 4-oxopiperidine-1-carboxylate (2.48 g, 12.47 mmol) were stirred in tetrahydrofuran (47.9 ml) and cooled in an ice bath. Sodium hydride (0.65 g, 16.21 mmol) was added and the reaction taken off the ice bath and stirred for 3.5 hours at room temperature. The reaction was quenched with water and extracted with dichloromethane, dried (magnesium sulphate), filtered and evaporated under reduced pressure. The crude material was purified by silica chromatography using a dichloromethane solvent system. The oil obtained was triturated with heptane and filtered to give the title compound as a yellow solid (1.32 g).
$^1$H NMR (CDCl$_3$, 400 MHz): δ 8.12 (d, 1H), 7.13 (d, 1H), 6.33 (s, 1H), 3.55 (t, 2H), 3.44 (t, 2H), 2.41 (t, 2H), 2.34 (t, 2H), 1.48 (s, 9H)

E: 5-Chloro-2-fluoro-4-(piperidin-4-ylmethyl)aniline

Step 1: A slurry of platinum (IV) oxide (0.074 mmol, 16.84 mg) in ethanol was added to a solution of tert-butyl 4-(2-chloro-5-fluoro-4-nitrobenzylidene)piperidine-1-carboxylate (1.483 mmol, 550 mg) in ethanol and the resulting suspension was hydrogenated at 3 bar for 45 minutes. The reaction mixture was filtered through celite, washing with ethanol. The filtrate was concentrated under vacuum to afford the intermediate tert-butyl 4-(4-amino-2-chloro-5-fluorobenzyl)piperidine-1-carboxylate (580 mg).
Step 2: tert-Butyl 4-(4-amino-2-chloro-5-fluorobenzyl)piperidine-1-carboxylate (1.692 mmol, 580 mg) was dissolved in dichloromethane (5 mL). Trifluoroacetic acid (1 mL) was added and the reaction stirred at room temperature for 30 minutes. The reaction mixture was purified by SCX chromatography to give the title compound (420 mg). MS (ESI) m/z 243.0 [M+H]+

F: 2-(4-((4-(4-Amino-3-fluorobenzyl)piperidin-1-yl)methyl)phenyl)-1,1,1,3,3,3-hexafluoropropan-2-ol 5-Chloro-2-fluoro-4-(piperidin-4-ylmethyl)aniline (1.730 mmol, 420 mg), 2-(4-(bromomethyl)phenyl)-1,1,1,3,3,3-hexafluoropropan-2-ol (1.730 mmol, 583 mg) and potassium carbonate (3.46 mmol, 478 mg) were combined and stirred at room temperature in acetonitrile (20 mL) for 2 hours. The reaction mixture was filtered and the filtrate concentrated under vacuum. The residue was purified by SCX chromatography to afford the title compound (800 mg). MS (ESI) m/z 499.5 [M+H]+

G: 1-(2-Amino-2-methylpropyl)-3-(5-chloro-2-fluoro-4-((1-(4-(1,1,1,3,3,3-hexafluoro-2-hydroxypropan-2-yl)benzyl)piperidin-4-yl)methyl)phenyl)urea A solution of 2-(4-((4-(4-amino-2-chloro-5-fluorobenzyl)piperidin-1-yl)methyl)phenyl)-1,1,1,3,3,3-hexafluoropropan-2-ol (0.200 mmol, 100 mg) and 4-nitrophenyl carbonochloridate (0.200 mmol, 40.4 mg) in tetrahydrofuran (5 mL) was stirred at room temperature for 30 minutes. 1-Amino-2-methylpropan-2-ol (0.401 mmol, 0.051 mL, 35.7 mg) was added and the reaction was kept at room temperature overnight. The reaction mixture was concentrated under vacuum and residue purified by silica column chromatography (eluent: dichloromethane-5% methanol in dichloromethane) to afford the title compound (58.5 mg). MS (ESI) m/z 614.1 [M+H]+

Example 16

1-(2,5-Difluoro-4-((1-(4-(1,1,1,3,3,3-hexafluoro-2-hydroxypropan-2-yl)benzyl)piperidin-4-yl)methyl)phenyl)-3-(2-hydroxy-2-methylpropyl)urea

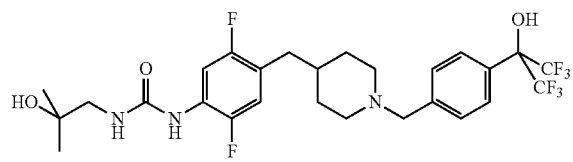

A: 1-(Bromomethyl)-2,5-difluoro-4-nitrobenzene 1,4-Difluoro-2-methyl-5-nitrobenzene (1 g) was dissolved in chlorobenzene (6 mL) and N-bromosuccinimide (1.54 g) added followed by benzoyl peroxide (0.2 g). The reaction mixture was stirred at reflux for 2.5 hours then additional benzoyl peroxide (0.2 g) and N-bromosuccinimide (1.54 g) were added. The reaction was refluxed for 2 hours then was cooled to room temperature, quenched with water and extracted with dichloromethane (3×). The combined organics were dried and concentrated under reduced pressure. The oil obtained was triturated with diethyl ether, filtered and the filtrate concentrated under reduced pressure to yield the title compound (3.21 g).

1H NMR (CDCl3, 400 MHz): δ 7.82 (dd, 1H), 7.40 (dd, 1H), 4.46 (s, 2H)

B: Diethyl 2,5-difluoro-4-nitrobenzylphosphonate 1-(Bromomethyl)-2,5-difluoro-4-nitrobenzene (8.3 g, 32.9 mmol) and triethyl phosphite (12.03 mL) were heated in an oil bath for 2.5 hours at 140° C. Additional triethyl phosphite (5 mL) was added and the reaction was stirred at 140° C. for 1 hour. The reaction mixture was evaporated under reduced pressure and chromatographed on silica eluting with dichloromethane/methanol (1:0-1%) to give the title compound (11 g, 35.6 mmol). 1H NMR (CDCl3, 400 MHz): δ 7.82 (dd, 1H), 7.37 (ddd, 1H), 4.11 (m, 4H), 3.24 (d, 2H), 1.30 (m, 6H)

C: tert-Butyl 4-(2,5-difluoro-4-nitrobenzylidene)piperidine-1-carboxylate

Diethyl 2,5-difluoro-4-nitrobenzylphosphonate (0.67 g, 2.17 mmol) and tert-butyl 4-oxopiperidine-1-carboxylate (0.43 g, 2.17 mmol) were stirred in tetrahydrofuran (8.3 mL) and cooled in an ice bath. Sodium hydride (0.133 g, 2.82 mmol) was added then the reaction was taken off ice bath and stirred for 4 hours at room temperature. The reaction was quenched with water and extracted with dichloromethane, dried (magnesium sulphate), filtered and evaporated under reduced pressure. The crude material was purified by silica chromatography using a dichloromethane solvent system. The solid obtained was triturated with heptane to give the title compound as a yellow solid (0.24 g). 1H NMR (CDCl3, 400 MHz): δ 7.80 (dd, 1H), 7.12 (dd, 1H), 6.24 (s, 1H), 3.54 (t, 2H), 3.45 (t, 2H), 2.40 (t, 2H), 2.56 (t, 2H), 1.48 (s, 9H)

D: 2,5-Difluoro-4-(piperidin-4-ylmethyl)aniline

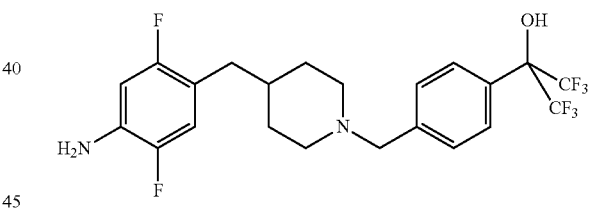

Step 1: A mixture of tert-butyl 4-(2,5-difluoro-4-nitrobenzylidene)piperidine-1-carboxylate (4.52 mmol, 1.6 g) and palladium on carbon (10%) (0.135 mmol, 0.144 g) in ethyl acetate was hydrogenated at 3 bar until the desired amount of hydrogen was consumed. The reaction was filtered through celite and concentrated under reduced pressure to give the intermediate tert-butyl 4-(4-amino-2,5-difluorobenzyl)piperidine-1-carboxylate.

Step 2: The intermediate tert-butyl 4-(4-amino-2,5-difluorobenzyl)piperidine-1-carboxylate was dissolved in dichloromethane and trifluoroacetic acid was added.

The reaction was stirred for 1 hour then was concentrated under reduced pressure. The residue was purified by SCX chromatography to give the intermediate 2,5-difluoro-4-(piperidin-4-ylmethyl)aniline (700 mg).

Step 3: To a stirred mixture of 2,5-difluoro-4-(piperidin-4-ylmethyl)aniline (3.09 mmol, 700 mg) and potassium carbonate (4.02 mmol, 556 mg) in acetonitrile was added 2-(4-(bromomethyl)phenyl)-1,1,1,3,3,3-hexafluoropropan-2-ol (3.09 mmol, 1043 mg). The reaction was stirred for 20 hours then was concentrated under reduced pressure. Dichloromethane was added and the reaction was filtered. The filtrate was chromatographed on silica (eluting with a gradient of dichloromethane to dichloromethane/ethyl acetate) to give the title compound (1.4 g).
MS (ESI) m/z 483.2 [M+H]+

E: 1-(2,5-Difluoro-4-((1-(4-(1,1,1,3,3,3-hexafluoro-2-hydroxypropan-2-yl)benzyl)piperidin-4-yl)methyl)phenyl)-3-(2-hydroxy-2-methylpropyl)urea A solution of 2-(4-((4-(4-amino-2,5-difluorobenzyl)piperidin-1-yl)methyl)phenyl)-1,1,1,3,3,3-hexafluoropropan-2-ol (0.311 mmol, 150 mg) and 4-nitrophenyl carbonochloridate (0.311 mmol, 62.7 mg) in tetrahydrofuran (5 mL) was stirred at room temperature for 30 minutes. 1-Amino-2-methylpropan-2-ol (0.622 mmol, 0.079 mL, 55.4 mg) was added and the reaction was stirred at room temperature overnight. The reaction mixture was concentrated under vacuum and the residue purified by column chromatography (eluent: 2-10% methanol in dichloromethane) to afford the title compound (89.5 mg). MS (ESI) m/z 598.2 [M+H]+

The following compounds were prepared in a similar manner:

16B: 1-(2,5-Difluoro-4-((1-(4-(1,1,1,3,3,3-hexafluoro-2-hydroxypropan-2-yl)benzyl)piperidin-4-yl)methyl)phenyl)-3-(3,3,3-trifluoro-2-hydroxy-2-methylpropyl)urea

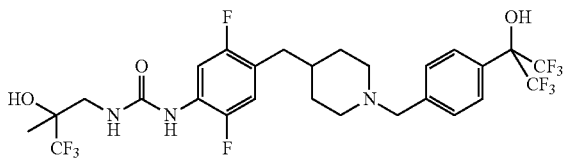 [SMILES: CC(O)(CNC(=O)Nc1cc(F)c(CC2CCN(Cc3ccc(C(O)(C(F)(F)F)C(F)(F)F)cc3)CC2)cc1F)C(F)(F)F]

MS (ESI) m/z 652.2 [M+H]+

16C: 1-(2,5-Difluoro-4-((1-(4-(1,1,1,3,3,3-hexafluoro-2-hydroxypropan-2-yl)benzyl)piperidin-4-yl)methyl)phenyl)-3-(oxetan-3-yl)urea

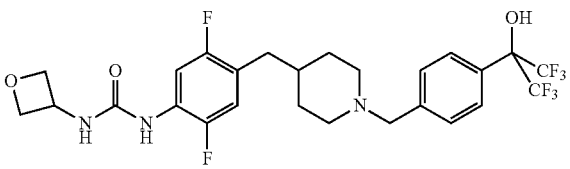 [SMILES: O=C(Nc1cc(F)c(CC2CCN(Cc3ccc(C(O)(C(F)(F)F)C(F)(F)F)cc3)CC2)cc1F)NC1COC1]

MS (ESI) m/z 582.2 [M+H]+

Example 17

1-(2-Chloro-4-((1-(4-(1,1,1,3,3,3-hexafluoro-2-hydroxypropan-2-yl)benzyl)piperidin-4-yl)methyl)phenyl)-3-(2-hydroxy-2-methylpropyl)urea

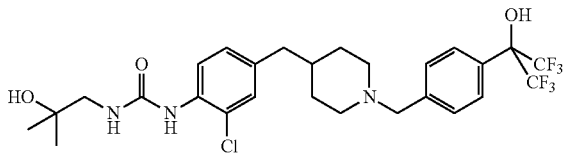 [SMILES: CC(C)(O)CNC(=O)Nc1ccc(CC2CCN(Cc3ccc(C(O)(C(F)(F)F)C(F)(F)F)cc3)CC2)cc1Cl]

A: 2-Chloro-4-(piperidin-4-ylmethyl)aniline

Step 1: 4-(Bromomethyl)-2-chloro-1-nitrobenzene (17.21 mmol, 4.31 g) and triethyl phosphite (25.8 mmol, 4.34 mL, 4.29 g) were combined and heated to 100° C. for 4 hours. The reaction mixture was quenched with water and extracted into ether. The organic phase was concentrated under vacuum. The resulting residue was purified by silica chromatography (eluting with dichloromethane-2% dichloromethane/methanol) to give the intermediate diethyl 3-chloro-4-nitrobenzylphosphonate (2.54 g).

Step 2: Diethyl 3-chloro-4-nitrobenzylphosphonate (2.80 mmol, 0.86 g), tert-butyl 4-oxopiperidine-1-carboxylate (2.80 mmol, 0.557 g) and tetrahydrofuran (4.89 mL) were stirred and sodium hydride (4.19 mmol, 0.168 g) was added. The reaction was stirred overnight at room temperature. Water was added and the reaction extracted with dichloromethane. The organic phase was dried over sodium sulfate and concentrated under vacuum to afford the intermediate tert-butyl 4-(3-chloro-4-nitrobenzylidene)-piperidine-1-carboxylate (0.85 g).

Step 3: A slurry of platinum (IV) oxide (0.037 mmol, 8.37 mg) in ethanol was added to a solution of tert-butyl 4-(3-chloro-4-nitrobenzylidene)piperidine-1-carboxylate (0.737 mmol, 260 mg) in ethanol and the resulting suspension was hydrogenated at 3 bar for 45 minutes. The reaction mixture was filtered through celite, washing with ethanol. The filtrate was concentrated under vacuum to afford the intermediate tert-butyl 4-(4-amino-3-chlorobenzyl)piperidine-1-carboxylate (200 mg).

Step 4: To a solution of tert-butyl 4-(4-amino-3-chlorobenzyl)piperidine-1-carboxylate (0.616 mmol, 200 mg) in dichloromethane (5 mL) was added trifluoroacetic acid (1 mL) and the reaction mixture stirred at room temperature for 1 hour. The reaction mixture was concentrated under vacuum and residue purified by SCX chromatography to afford the title compound (100 mg). MS (ESI) m/z 480.9 [M+H]+

B: 2-(4-((4-(4-Amino-3-chlorobenzyl)piperidin-1-yl)methyl)phenyl)-1,1,1,3,3,3-hexafluoropropan-2-ol 2-Chloro-4-(piperidin-4-ylmethyl)aniline (0.445 mmol, 100 mg), 2-(4-(bromomethyl)-phenyl)-1,1,1,3,3,3-hexafluoropropan-2-ol (0.445 mmol, 150 mg) and potassium carbonate (0.890 mmol, 123 mg) were combined and stirred at room temperature in acetonitrile (5 mL) for 1.5 hours. The reaction mixture was filtered and filtrate was concentrated under vacuum. The residue was purified by SCX chromatography to give the title compound (200 mg). MS (ESI) m/z 480.9 [M+H]+

C: 1-(2-Chloro-4-((1-(4-(1,1,1,3,3,3-hexafluoro-2-hydroxypropan-2-yl)benzyl)piperidin-4-yl)methyl)phenyl)-3-(2-hydroxy-2-methylpropyl)urea A solution of 2-(4-((4-(4-amino-3-chlorobenzyl)piperidin-1-yl)methyl)phenyl)-1,1,1,3,3,3-hexafluoropropan-2-ol (0.416 mmol, 200 mg) and 4-nitrophenyl carbonochloridate (0.416 mmol, 84 mg) in tetrahydrofuran (5 mL) was stirred at room temperature for 30 minutes. 1-Amino-2-methylpropan-2-ol (0.832 mmol, 0.106 mL, 74.1 mg) was added and the reaction was stirred at room temperature overnight. The reaction mixture was concentrated under vacuum and the residue purified by silica column chromatography (eluent: dichloromethane-5% methanol in dichloromethane) to afford the title compound (58.5 mg). MS (ESI) m/z 596.5 [M+H]+

The following compound was prepared in a similar manner:

17B: 1-(2-Chloro-4-((1-(4-(1,1,1,3,3,3-hexafluoro-2-hydroxypropan-2-yl)benzyl)piperidin-4-yl)methyl)phenyl)-3-(oxetan-3-yl)urea

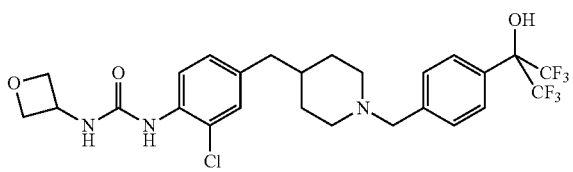 [SMILES: O=C(Nc1ccc(CC2CCN(Cc3ccc(C(O)(C(F)(F)F)C(F)(F)F)cc3)CC2)cc1Cl)NC1COC1]

MS (ESI) m/z 580.2 [M+H]$^+$

Example 18

(S)-1-(4-(1-(4-(1,1,1,3,3,3-Hexafluoro-2-hydroxypropan-2-yl)benzyl)piperidin-4-ylthio)phenyl)-3-(tetrahydrofuran-3-yl)urea

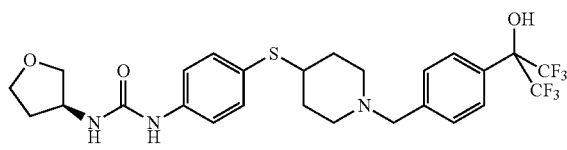 [SMILES: O=C(Nc1ccc(SC2CCN(Cc3ccc(C(O)(C(F)(F)F)C(F)(F)F)cc3)CC2)cc1)N[C@H]1CCOC1]

A: tert-Butyl 4-(4-nitrophenylthio)piperidine-1-carboxylate

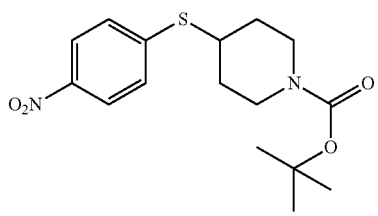

4-Nitrobenzenethiol (23.99 mmol, 4.653 g) and sodium hydride (32.9 mmol, 1.314 g) were combined in tetrahydrofuran and stirred at 0° C. for 30 minutes. tert-Butyl 4-(methylsulfonyloxy)piperidine-1-carboxylate (36.0 mmol, 10.05 g) was added and the reaction mixture stirred and heated overnight at 60° C. The reaction mixture was concentrated under vacuum and the residue partitioned between dichloromethane and water, the organic layer was separated, dried, and concentrated under vacuum. The residue was purified by silica column chromatography (eluting with a 0-10% methanol/dichloromethane gradient) to afford the title compound (2.90 g).

$^1$H NMR (CDCl$_3$, 400 MHz): δ 8.14 (d, 2H), 7.40 (d, 2H), 3.97 (d, 2H), 3.48 (m, 1H), 3.04 (t, 2H), 2.01 (dd, 2H), 1.62 (qd, 2H), 1.47 (s, 9H)

B: tert-Butyl 4-(4-aminophenylthio)piperidine-1-carboxylate

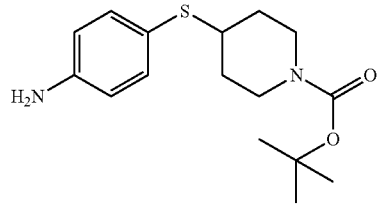 [SMILES: CC(C)(C)OC(=O)N1CCC(Sc2ccc([N+](=O)[O-])cc2)CC1]

tert-Butyl 4-(4-nitrophenylthio)piperidine-1-carboxylate (8.56 mmol, 2.8973 g) and palladium (3.77 mmol, 0.401 g) were combined in ethanol (30 mL) and the reaction mixture hydrogenated at 5 bar for 2 hours. The reaction mixture was filtered and concentrated under vacuum, reaction incomplete. Hydrogenation resumed with fresh palladium and left overnight. The reaction mixture was filtered and concentrated under vacuum to afford the title compound (2.86 g).

$^1$H NMR (CDCl$_3$, 400 MHz): δ 7.26 (dd, 2H), 6.61 (dd, 2H), 3.96 (d, 2H), 2.94 (m, 1H), 2.84 (t, 2H), 1.85 (d, 2H), 1.46 (d, 2H), 1.44 (s, 9H)

C: 4-(Piperidin-4-ylthio)aniline

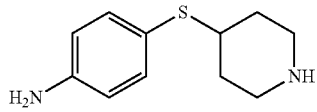

tert-Butyl 4-(4-aminophenylthio)piperidine-1-carboxylate (9.27 mmol, 2.859 g) was dissolved in dichloromethane (10 ml) and trifluoroacetic acid (10 mL) and the reaction mixture stirred at room temperature for 30 minutes. The reaction mixture was purified via SCX column chromatography to afford the title compound (1.39 g).

$^1$H NMR (CDCl$_3$, 400 MHz): δ 7.25 (d, 2H), 6.61 (d, 2H), 3.72 (s, 1H), 3.07 (dt, 2H), 2.91 (s, 1H), 2.58 (t, 2H), 1.89 (dd, 2H), 1.66 (s, 2H), 1.45 (qd, 2H)

D: 2-(4-((4-(4-Aminophenylthio)piperidin-1-yl)methyl)phenyl)-1,1,1,3,3,3-hexafluoropropan-2-ol

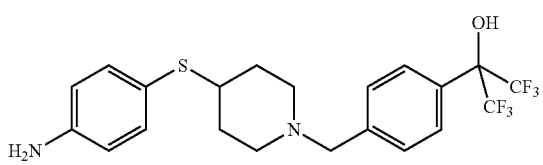 [SMILES: Nc1ccc(SC2CCN(Cc3ccc(C(O)(C(F)(F)F)C(F)(F)F)cc3)CC2)cc1]

4-(Piperidin-4-ylthio)aniline (6.69 mmol, 1.3946 g), 2-(4-(bromomethyl)phenyl)-1,1,1,3,3,3-hexafluoropropan-2-ol (6.69 mmol, 2.256 g), and potassium carbonate (13.39 mmol, 1.850 g) were combined in acetonitrile (20 mL) and the reaction mixture stirred at room temperature for 1 hour. The reaction mixture was concentrated under vacuum, and partitioned between dichloromethane and water. The organic layer was separated, dried, and concentrated under vacuum. The residue was purified by silica column chromatography (eluting with 2.5-5% methanol/dichloromethane gradient) to afford the title compound (1.93 g). MS m/z 465.0 [M+H]+

E: (S)-1-(4-(1-(4-(1,1,1,3,3,3-Hexafluoro-2-hydroxypropan-2-yl)benzyl)piperidin-4-ylthio)phenyl)-3-(tetrahydrofuran-3-yl)urea 2-(4-((4-(4-Aminophenylthio)piperidin-1-yl)methyl)phenyl)-1,1,1,3,3,3-hexafluoro-propan-2-ol (1.076 mmol, 500 mg), and 4-nitrophenyl carbonochloridate (1.076 mmol, 217 mg) were combined in dichloromethane (10 mL) and the reaction mixture stirred at room temperature for 1 hour. (S)-Tetrahydrofuran-3-amine hydrochloride (2.153 mmol, 266 mg), and N-ethyl-N-isopropylpropan-2-amine (2.153 mmol, 0.356 mL, 278 mg) were added and the reaction mixture stirred for 30 minutes. The reaction mixture was washed with water, and the organic layer separated, dried, and concentrated under vacuum. The residue was purified by silica column chromatography (eluting with 0-10% methanol/dichloromethane gradient) to afford the title compound (284 mg). MS m/z 578.2 [M+H]+

Example 19

1-(4-(1-(4-(1,1,1,3,3,3-Hexafluoro-2-hydroxypropan-2-yl)benzyl)piperidin-4-ylsulfinyl)phenyl)-3-((S)-tetrahydrofuran-3-yl)urea

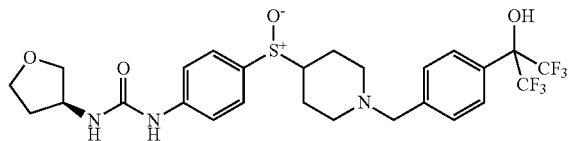 [SMILES: O=C(Nc1ccc([S+]([O-])C2CCN(Cc3ccc(C(O)(C(F)(F)F)C(F)(F)F)cc3)CC2)cc1)N[C@H]1CCOC1]

(S)-1-(4-(1-(4-(1,1,1,3,3,3-Hexafluoro-2-hydroxypropan-2-yl)benzyl)piperidin-4-ylthio)phenyl)-3-(tetrahydrofuran-3-yl)urea (0.246 mmol, 142 mg) was dissolved in dichloromethane (5 mL) and the solution cooled to 0° C. 3-Chlorobenzoperoxoic acid (0.246 mmol, 42.4 mg) was added and the reaction mixture stirred for 2 hours. The reaction mixture was diluted with methanol and dichloromethane. The reaction mixture was washed with water and the organic layer separated, dried, and concentrated under vacuum. The residue was purified by silica column chromatography (eluting with a dichloromethane/methanol/ammonia gradient) to afford the title compound. MS m/z 594.5 [M+H]+

Example 20

1-(4-(1-(4-(1,1,1,3,3,3-Hexafluoro-2-hydroxypropan-2-yl)benzyl)piperidin-4-ylsulfonyl)phenyl)-3-(2-hydroxy-2-methylpropyl)urea

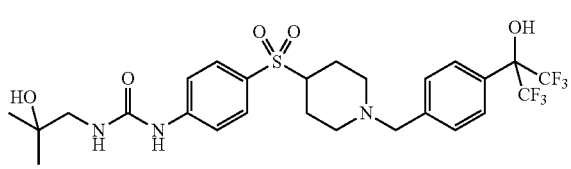 [SMILES: CC(C)(O)CNC(=O)Nc1ccc(S(=O)(=O)C2CCN(Cc3ccc(C(O)(C(F)(F)F)C(F)(F)F)cc3)CC2)cc1]

A: Tert-butyl 4-(4-nitrophenylthio)piperidine-1-carboxylate

4-Nitrobenzenethiol (5.93 mmol, 1.15 g), and sodium hydride (8.12 mmol, 0.325 g) were combined in tetrahydrofuran and stirred at 0° C. for 30 minutes. tert-Butyl 4-(methylsulfonyloxy)piperidine-1-carboxylate (8.89 mmol, 2.484 g) was added and the reaction mixture heated at 60° C. overnight. The reaction mixture was concentrated under vacuum and residue dissolved in dichloromethane and washed with water. The organic layer was separated, dried and concentrated under vacuum. The residue was purified by silica column chromatography (eluent: dichloromethane) to afford the title compound (1.45 g). MS (ESI) m/z 339.5 [M+H]+

B: 4-(Piperidin-4-ylsulfonyl)aniline

Step 1: To an ice-cooled solution of tert-butyl 4-(4-nitrophenylthio)piperidine-1-carboxylate (2.216 mmol, 0.75 g) in dichloromethane was added 3-chloroperoxy-benzoic acid (4.43 mmol, 0.993 g). The reaction was stirred at 0° C. for 30 minutes then was allowed to warm to room temperature and stir for a further 2 hours. The reaction mixture was diluted with dichloromethane and 1M hydrochloric acid. The organic layer was separated and dried to give the intermediate tert-butyl 4-(4-nitrophenyl-sulfonyl)piperidine-1-carboxylate.

Step 2: tert-Butyl 4-(4-nitrophenylsulfonyl)piperidine-1-carboxylate (2.214 mmol, 820 mg) was dissolved in dichloromethane (10 mL). Trifluoroacetic acid (2 mL) was added and the reaction stirred at room temperature for 1 hour. The reaction mixture was concentrated under vacuum and purified by SCX chromatography to give the intermediate 4-(4-nitrophenylsulfonyl)piperidine (640 mg).

Step 3: 4-(4-Nitrophenylsulfonyl)piperidine (2.368 mmol, 640 mg) and palladium (10% on carbon, Degussa) (0.024 mmol, 50.4 mg) were hydrogenated in ethanol at 3 bar at room temperature for 1 hour. The reaction mixture was filtered through celite and concentrated under vacuum to give the title compound MS (ESI) m/z 241.3 [M+H]+

C: 2-(4-((4-(4-Aminophenylsulfonyl)piperidin-1-yl)methyl)phenyl)-1,1,1,3,3,3-hexafluoropropan-2-ol 4-(Piperidin-4-ylsulfonyl)aniline (1.748 mmol, 420 mg), 2-(4-(bromomethyl)phenyl)-1,1,1,3,3,3-hexafluoropropan-2-ol (1.748 mmol, 589 mg) and potassium carbonate (3.50 mmol, 483 mg) were combined in acetonitrile (5 mL). Dimethylsulfoxide (0.5 mL) was added and the reaction stirred at room temperature for 1.5 hours. The reaction mixture was filtered and filtrate was concentrated under vacuum. The residue was purified by SCX chromatography to give the title compound (700 mg).
MS (ESI) m/z 497.0 [M+H]+

D: 1-(4-(1-(4-(1,1,1,3,3,3-Hexafluoro-2-hydroxypropan-2-yl)benzyl)piperidin-4-ylsulfonyl)phenyl)-3-(2-hydroxy-2-methylpropyl)urea A solution of 2-(4-((4-(4-aminophenylsulfonyl)piperidin-111)methyl)phenyl)-1,1,1,3,3,3-hexafluoropropan-2-ol (0.201 mmol, 100 mg) and 4-nitrophenyl carbonochloridate (0.201 mmol, 40.6 mg) in tetrahydrofuran (5 mL) was stirred at room temperature for 30 minutes. 1-Amino-2-methylpropan-2-ol (0.403 mmol, 0.051 mL, 35.9 mg) was added and the reaction was stirred at room temperature overnight. The reaction mixture was concentrated under vacuum and the residue was purified by silica column chromatography (eluent:

dichloromethane-5% methanol in dichloromethane) to afford the title compound (35.5 mg). MS (ESI) m/z 612.2 [M+H]+

The following compounds were prepared in a similar manner:

20B: (S)-1-(4-(1-(4-(1,1,1,3,3,3-Hexafluoro-2-hydroxypropan-2-yl)benzyl)piperidin-4-ylsulfonyl(phenyl)-3-(tetrahydrofuran-3-yl)urea

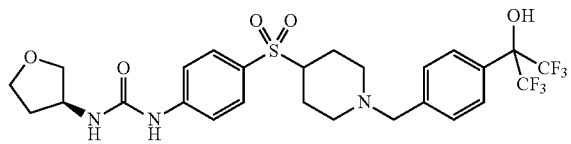 [SMILES: O=C(Nc1ccc(S(=O)(=O)C2CCN(Cc3ccc(C(O)(C(F)(F)F)C(F)(F)F)cc3)CC2)cc1)N[C@H]1CCOC1]

MS (ESI) m/z 610.5 [M+H]+

20C: 1-(4-(1-(4-(1,1,1,3,3,3-Hexafluoro-2-hydroxypropan-2-yl)benzyl)piperidin-4-ylsulfonyl)phenyl)-3-(oxetan-3-yl)urea

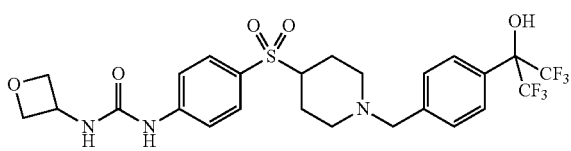 [SMILES: O=C(Nc1ccc(S(=O)(=O)C2CCN(Cc3ccc(C(O)(C(F)(F)F)C(F)(F)F)cc3)CC2)cc1)NC1COC1]

MS (ESI) m/z 596.0 [M+H]+

Example 21

4-(3-(Cyclopropylmethyl)ureido)-N-(1-(4-(1,1,1,3,3,3-hexafluoro-2-hydroxypropan-2-yl)benzyl)piperidin-4-yl)-N-methylbenzamide

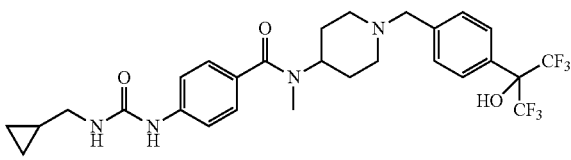 [SMILES: CN(C(=O)c1ccc(NC(=O)NCC2CC2)cc1)C1CCN(Cc2ccc(C(O)(C(F)(F)F)C(F)(F)F)cc2)CC1]

A: Ethyl 4-(3-(cyclopropylmethyl)ureido)benzoate

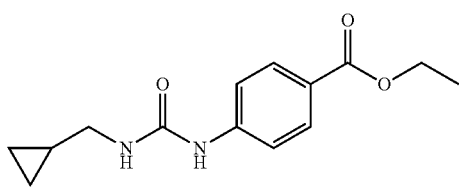 [SMILES: CCOC(=O)c1ccc(NC(=O)NCC2CC2)cc1]

To cyclopropylmethanamine (57.5 mmol, 4.99 mL, 4.09 g) in dichloromethane (40 mL) was added to ethyl 4-isocyanatobenzoate (52.3 mmol, 10 g) in dichloromethane (45 mL) and the reaction stirred overnight. The reaction was then concentrated under reduced pressure to give the title compound (14.7 g).

¹H NMR (CDCl₃, 400 MHz): δ 0.2 (2H, m) 0.5, (2H, m) 0.95 (1H, m) 1.4 (3H, t), 3.1 (2H, m) 4.35 (2H, q), 5.15 (1H, br s), 7.0 (1H, br s), 7.4 (2H, d) 8.0 (2H, d)

B: 4-(3-(Cyclopropylmethyl)ureido)benzoic acid

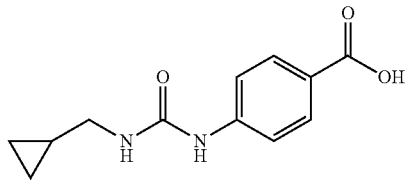 [SMILES: O=C(NCC1CC1)Nc1ccc(C(=O)O)cc1]

Ethyl 4-(3-(cyclopropylmethyl)ureido)benzoate (55.3 mmol, 14.5 g) was suspended in ethanol (400 mL) and 4M sodium hydroxide (332 mmol, 83 mL) added. The reaction was then refluxed until complete saponification was achieved. The ethanol was removed by evaporation and the reaction neutralised with concentrated hydrochloric acid. The white precipitate was collected and washed with water. The material was dried under vacuum to give the title compound (12.1 g).

¹H NMR ((CD₃)₂SO, 400 MHz): δ 0.2 (2H, m) 0.5, (2H, m) 0.95 (1H, m), 3.0 (2H, m), 6.35 (1H, br s) 7.4 (2H, d) 7.8 (2H, d) 8.9 (1H, br s)

C: 1-(4-(1,1,1,3,3,3-Hexafluoro-2-hydroxypropan-2-yl)benzyl)piperidin-4-yl(methyl)carbamate

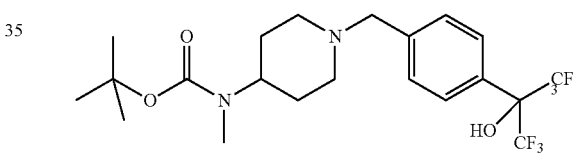

A mixture of tert-butyl methyl(piperidin-4-yl)carbamate (5.09 mmol, 1.09 g), 2-(4-(bromomethyl)phenyl)-1,1,1,3,3,3-hexafluoropropan-2-ol (5.09 mmol, 1.714 g) and sodium hydrogencarbonate (7.63 mmol, 0.641 g) in acetonitrile (20 mL) was refluxed for 2 hours. The reaction was concentrated under reduced pressure and dichloromethane added. The suspension was filtered and the filtrate was chromatographed on silica (eluting with a gradient of dichloromethane to ethyl acetate) to give the title compound (1.7 g). MS (ESI) m/z 471.1 [M+H]+

D: 1,1,1,3,3,3-Hexafluoro-2-(4-((4-(methylamino) piperidin-1-yl)methyl)phenyl)propan-2-ol

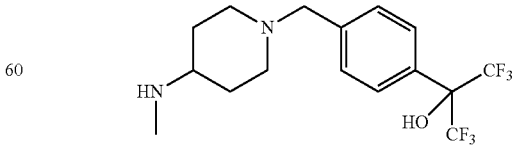

A mixture of tert-butyl 1-(4-(1,1,1,3,3,3-hexafluoro-2-hydroxypropan-2-yl)benzyl)-piperidin-4-yl(methyl)carbamate (3.19 mmol, 1.5 g), dichloromethane (5 mL) and trifluoroacetic acid (5 mL) was stirred for 20 hours. Purification by SCX chromatography gave the title compound (1.1 g). MS (ESI) m/z 371.4 [M+H]⁺

E: 4-(3-(Cyclopropylmethyl)ureido)-N-(1-(4-(1,1,1,3,3,3-hexafluoro-2-hydroxypropan-2-yl)benzyl)piperidin-4-yl)-N-methylbenzamide To a mixture of 4-(3-(cyclopropylmethyl)ureido)benzoic acid (0.810 mmol, 190 mg), 1,1,1,3,3,3-hexafluoro-2-(4-((4-(methylamino)piperidin-1-yl)methyl)phenyl)propan-2-ol (0.810 mmol, 300 mg) and triethylamine (1.944 mmol, 0.271 mL, 197 mg) in dichloromethane (50 mL) was added N1-((ethylimino)methylene)-N3,N3-dimethylpropane-1,3-diamine hydrochloride (0.972 mmol, 186 mg). The reaction was stirred for 24 hours. Chromatography on silica eluting with dichloromethane to dichloromethane/methanol (10%) gave the title compound (370 mg).
MS (ESI) m/z 587.2 [M+H]⁺

Example 22

4-(3-(Cyclopropylmethyl)ureido)-N-ethyl-N-(1-(4-(1,1,1,3,3,3-hexafluoro-2-hydroxypropan-2-yl)benzyl)piperidin-4-yl)benzamide

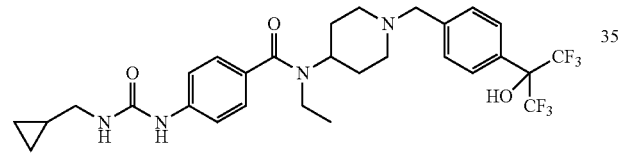

A: Ethyl(1-(4-(1,1,1,3,3,3-hexafluoro-2-hydroxypropan-2-yl)benzyl)piperidin-4-yl)carbamate

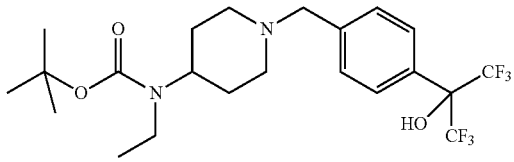 [SMILES: CCN(C(=O)OC(C)(C)C)C1CCN(Cc2ccc(C(O)(C(F)(F)F)C(F)(F)F)cc2)CC1]

A mixture of tert-butyl ethyl(piperidin-4-yl)carbamate (10.95 mmol, 2.5 g), 2-(4-(bromomethyl)phenyl)-1,1,1,3,3,3-hexafluoropropan-2-ol (10.95 mmol, 3.69 g) and sodium hydrogencarbonate (16.42 mmol, 1.380 g) in acetonitrile (40 ml) was refluxed for 2 hours. The reaction was concentrated under reduced pressure and dichloromethane was added. The suspension was filtered and the filtrate was chromatographed on silica (eluting with a gradient of dichloromethane to ethyl acetate) to give the title compound (3.3 g). MS (ESI) m/z 485.1 [M+H]⁺

B: 2-(4-((4-(Ethylamino)piperidin-1-yl)methyl)phenyl)-1,1,1,3,3,3-hexafluoropropan-2-ol

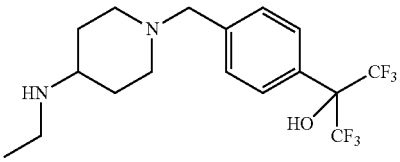 [SMILES: CCNC1CCN(Cc2ccc(C(O)(C(F)(F)F)C(F)(F)F)cc2)CC1]

A mixture of tert-butyl ethyl(1-(4-(1,1,1,3,3,3-hexafluoro-2-hydroxypropan-2-yl)benzyl)piperidin-4-yl)carbamate (6.61 mmol, 3.2 g), dichloromethane (10 mL) and trifluoroacetic acid (10 mL) was stirred for 20 hours. Purification by SCX chromatography gave the title compound (2.5 g). MS (ESI) m/z 385.1 [M+H]⁺

C: 4-(3-(Cyclopropylmethyl)ureido)-N-ethyl-N-(1-(4-(1,1,1,3,3,3-hexafluoro-2-hydroxypropan-2-yl)benzyl)piperidin-4-yl)benzamide To a mixture of 4-(3-(cyclopropylmethyl)ureido)benzoic acid (0.781 mmol, 183 mg), 2-(4-((4-(ethylamino)piperidin-1-yl)methyl)phenyl)-1,1,1,3,3,3-hexafluoropropan-2-ol (0.781 mmol, 300 mg) and triethylamine (1.873 mmol, 0.261 mL, 190 mg) in dichloromethane (50 mL) was added N1-((ethylimino)methylene)-N3,N3-dimethylpropane-1,3-diamine hydrochloride (0.937 mmol, 180 mg). The reaction was stirred for 24 hours. Chromatography on silica eluting with dichloromethane to dichloromethane/methanol (10%) gave the title compound (250 mg).
MS (ESI) m/z 601.2 [M+H]⁺

Example 23

4-(3-(Cyclopropylmethyl)ureido)-N-(1-(4-(1,1,1,3,3,3-hexafluoro-2-hydroxypropan-2-yl)benzyl)pyrrolidin-3-yl)-N-methylbenzamide

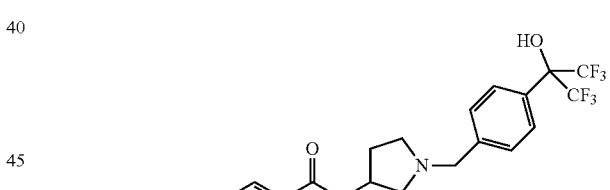

A: 4-(3-(Cyclopropylmethyl)ureido)-N-methyl-N-(pyrrolidin-3-yl)benzamide

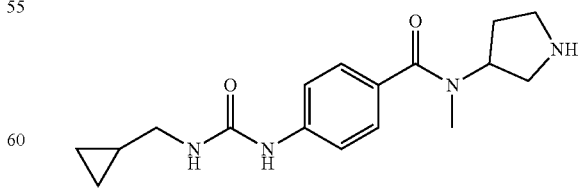

Step 1: To a stirred mixture of 4-(3-(cyclopropylmethyl)ureido)benzoic acid (4.99 mmol, 1.170 g), tert-butyl 3-(methylamino)pyrrolidine-1-carboxylate (4.99 mmol, 1 g) and triethylamine (11.98 mmol, 1.670 mL, 1.213 g) in dichloromethane (50 mL) was added N1-((ethylimino)methylene)-N3,N3-dimethylpropane-1,3-diamine hydrochloride (5.99 mmol, 1.149 g). The reaction was stirred for 20 hours. Chromatography on silica (eluting with a gradient of dichloromethane to ethyl acetate) gave the intermediate tert-butyl 3-(4-(3-(cyclopropylmethyl)ureido)-N-methylbenzamido)-pyrrolidine-1-carboxylate (2 g).

Step 2: A mixture of tert-butyl 3-(4-(3-(cyclopropylmethyl)ureido)-N-methyl-benzamido)pyrrolidine-1-carboxylate (4.80 mmol, 2 g), trifluoroacetic acid (10 mL) and dichloromethane (10 mL) were stirred for 20 hours. The reaction was concentrated under reduced pressure and purified by SCX chromatography to yield the title compound (1.5 g). MS (ESI) m/z 317.1 [M+H]+

B: 4-(3-(Cyclopropylmethyl)ureido)-N-(1-(4-(1,1,1,3,3,3-hexafluoro-2-hydroxypropan-2-yl)benzyl)pyrrolidin-3-yl)-N-methylbenzamide A mixture of 4-(3-(cyclopropylmethyl)ureido)-N-methyl-N-(pyrrolidin-3-yl)benzamide (4.74 mmol, 1.5 g), 2-(4-(bromomethyl)phenyl)-1,1,1,3,3,3-hexafluoropropan-2-ol (4.74 mmol, 1.598 g) and potassium carbonate (7.11 mmol, 0.983 g) in acetonitrile (40 mL) was refluxed for 5 hours. The reaction was concentrated under reduced pressure and dichloromethane/methanol was added. The suspension was filtered and the filtrate was concentrated under reduced pressure. Chromatography on silica eluting with a gradient of dichloromethane/methanol gave the title compound (400 mg). MS (ESI) m/z 573.2 [M+H]+

Example 24

4-(3-(Cyclopropylmethyl)ureido)-N-(1-(3-(1,1,1,3,3,3-hexafluoro-2-hydroxypropan-2-yl)benzyl)piperidin-4-yl)-N-methylbenzamide

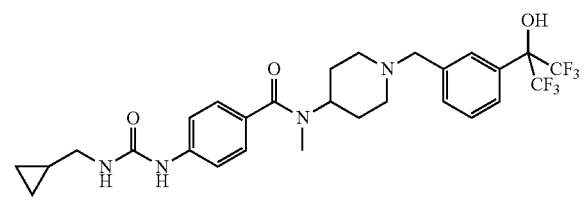 [SMILES: CN(C(=O)c1ccc(NC(=O)NCC2CC2)cc1)C1CCN(Cc2cccc(C(O)(C(F)(F)F)C(F)(F)F)c2)CC1]

A: 1,1,1,3,3,3-Hexafluoro-2-m-tolylpropan-2-ol

Cesium fluoride (8.328 g, 54.83 mmol) was added to a solution of ethyl 3-methylbenzoate (5.82 mL, 36.49 mmol) and (trifluoromethyl)trimethylsilane (23.35 mL, 146.36 mmol) in N,N-dimethylformamide (30 mL) at −78° C. The mixture was slowly allowed to warm to ambient temperature over 68 hours. The reaction mixture was washed with water, concentrated under reduced pressure, and purified by silica chromatography (eluting with a solvent gradient from heptane to 5% ethyl acetate/95% heptane) to afford the title compound (359 mg).

$^1$H NMR (CDCl$_3$, 400 MHz): δ 7.28-7.57 (4H, m), 2.40 (3H, s)

B: 2-(3-(Bromomethyl)phenyl)-1,1,1,3,3,3-hexafluoropropan-2-ol

N-Bromosuccinimide (207 mg, 1.162 mmol) was added to a solution of 1,1,1,3,3,3-hexafluoro-2-m-tolylpropan-2-ol (300 mg, 1.162 mmol) and 2,2'-azobis(isobutyronitrile) (0.191 mg, 1.162 μmol) in carbon tetrachloride (6 mL). The mixture was refluxed for 18 hours and then concentrated under reduced pressure. The crude material was dissolved in diethyl ether and heptane, filtered through dicalite, and purified by silica chromatography (eluting with a solvent gradient from 2% ethyl acetate/98% heptane to 10% ethyl acetate/90% heptane) to afford the title compound (84 mg).

$^1$H NMR (CDCl$_3$, 400 MHz): δ 7.39-7.78 (4H, m), 4.51 (2H, s)

C: tert-Butyl 4-(4-(3-(cyclopropylmethyl)ureido)-N-methylbenzamido)piperidine-1-carboxylate

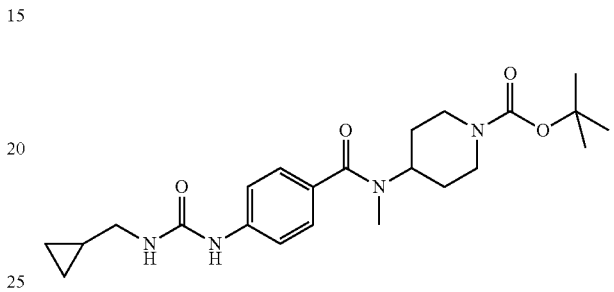

Propanephosphonic acid cyclic anhydride (3.74 mL, 6.40 mmol) was added to a solution of 4-(3-(cyclopropylmethyl)ureido)benzoic acid (500 mg, 2.134 mmol), tert-butyl 4-(methylamino)piperidine-1-carboxylate (457 mg, 2.134 mmol) and triethylamine (1.19 mL, 8.54 mmol) in dichloromethane (20 mL). The mixture was stirred at ambient temp for 3.5 hours and then concentrated under reduced pressure. The crude material was purified by silica chromatography (eluting with a solvent gradient from 2.5% methanol/97.5% dichloromethane to 5% methanol/95% dichloromethane) to afford the title compound (440 mg). MS (ESI) m/z 431.5 [M+H]+

D: 4-(3-(Cyclopropylmethyl)ureido)-N-methyl-N-(piperidin-4-yl)benzamide

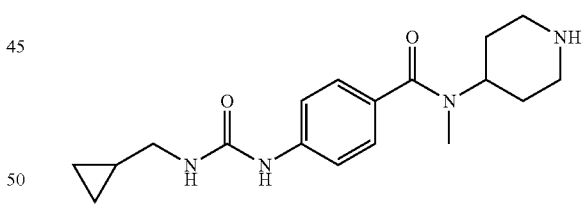

2,2,2-Trifluoroacetic acid (1.88 mL, 24.39 mmol) was added to a solution of tert-butyl 4-(4-(3-(cyclopropylmethyl)ureido)-N-methylbenzamido)piperidine-1-carboxylate (420 mg, 0.975 mmol) in dichloromethane (10 mL). The mixture was stirred at ambient temperature for 4 hours and then treated with strong cation exchange column chromatography to afford the title compound (300 mg). MS (ESI) m/z 331.1 [M+H]+

E: 4-(3-(Cyclopropylmethyl)ureido)-N-(1-(3-(1,1,1,3,3,3-hexafluoro-2-hydroxypropan-2-yl)benzyl)piperidin-4-yl)-N-methylbenzamide 2-(3-(Bromomethyl)phenyl)-1,1,1,3,3,3-hexafluoropropan-2-ol (84 mg, 0.249 mmol) was added to a solution of 4-(3-(cyclopropylmethyl)ureido)-N-methyl-N-(piperidin-4-yl)benzamide (82 mg, 0.249 mmol), sodium iodide (15 mg, 0.100 mmol), and potassium carbonate (103 mg, 0.748 mmol) in acetonitrile (3 mL) and the solution was stirred at ambient temperature overnight. The reaction mixture was concentrated under vacuum, dissolved in dichloromethane, washed with water, and purified by silica chromatography (eluting with a solvent gradient from dichloromethane to 3.5% methanol/96.5% dichloromethane) to afford the title compound (57 mg).

MS (ESI) m/z 587.2 [M+H]$^+$

Example 25

1-(4-(1-(4-(1,1,1,3,3,3-Hexafluoro-2-hydroxypropan-2-yl)benzyl)piperidin-4-yl)phenyl)-3-(pyridin-4-yl)urea

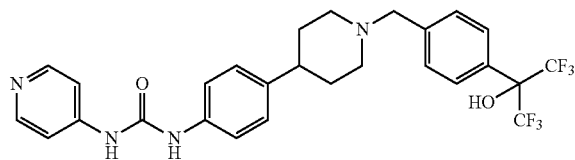 [SMILES: O=C(Nc1ccncc1)Nc1ccc(C2CCN(Cc3ccc(C(O)(C(F)(F)F)C(F)(F)F)cc3)CC2)cc1]

A: 2-(4-((4-(4-Aminophenyl)piperidin-1-yl)methyl)phenyl)-1,1,1,3,3,3-hexafluoropropan-2-ol

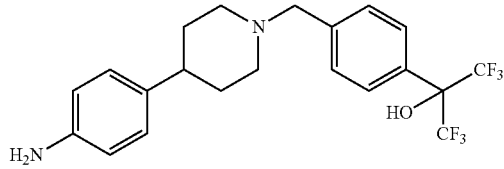 [SMILES: Nc1ccc(C2CCN(Cc3ccc(C(O)(C(F)(F)F)C(F)(F)F)cc3)CC2)cc1]

A mixture of 4-(piperidin-4-yl)aniline hydrochloride (14.10 mmol, 3 g), 2-(4-(bromomethyl)phenyl)-1,1,1,3,3,3-hexafluoropropan-2-ol (14.10 mmol, 4.75 g) and potassium carbonate (42.3 mmol, 5.85 g) in acetonitrile was heated to 60° C. (heating block temperature) for 20 hours. The reaction was concentrated under reduced pressure and dichloromethane was added. The mixture was chromatographed on silica (eluting with a gradient of dichloromethane to ethyl acetate) to give the title compound (770 mg). MS (ESI) m/z 433.3 [M+H]$^+$ B: 1-(4-(1-(4-(1,1,1,3,3,3-Hexafluoro-2-hydroxypropan-2-yl)benzyl)piperidin-4-yl)phenyl)-3-(pyridin-4-yl)urea Reaction 1: A mixture of 2-(4-((4-(4-aminophenyl)piperidin-1-yl)methyl)phenyl)-1,1,1,3,3,3-hexafluoropropan-2-ol (0.694 mmol, 300 mg) and phenyl pyridin-4-ylcarbamate (1.041 mmol, 223 mg) in dioxane was heated in a reactivial at 100° C. (heating block temperature) for 48 hours.

Reaction 2: A mixture of 2-(4-((4-(4-aminophenyl)piperidin-1-yl)methyl)phenyl)-1,1,1,3,3,3-hexafluoropropan-2-ol (0.925 mmol, 400 mg) and phenyl pyridin-4-ylcarbamate (1.388 mmol, 297 mg) in dioxane was heated in a reactivial at 100° C. (heating block temperature) for 48 hours.

The two reactions were then combined and concentrated under reduced pressure. The residue was purified by chromatography on silica (eluting with a gradient of dichloromethane to dichloromethane/methanol (15%)), then by reverse phase HPLC, to give the title compound (400 mg). MS (ESI) m/z 553.2 [M+H]$^+$ Example 26

1-(2-Fluoro-4-((1-(4-(1,1,1,3,3,3-hexafluoro-2-hydroxypropan-2-yl)benzyl)piperidin-4-yl)(hydroxy)methyl)phenyl)-3-((S)-tetrahydrofuran-3-yl)urea

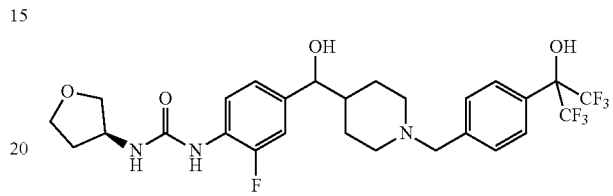

A: 2-(4-((4-((4-Amino-3-fluorophenyl)(hydroxy)methyl)piperidin-1-yl)methyl)phenyl)-1,1,1,3,3,3-hexafluoropropan-2-ol 2-(4-((4-(4-Amino-3-fluorobenzylidene)piperidin-1-yl)methyl)phenyl)-1,1,1,3,3,3-hexafluoropropan-2-ol (1.384 mmol, 0.64 g) was cooled to 0° C. and 1M diborane solution in tetrahydrofuran (5.54 mmol, 5.54 mL) added dropwise. The mixture was allowed to warm to room temperature and stirred overnight. The mixture was cooled to 0° C. and ethanol slowly added. Sodium hydroxide (8.30 mmol, 0.332 g) in water (20 mL) was then added slowly with stirring, followed by hydrogen peroxide (24.91 mmol, 2.421 g). The mixture was stirred at room temperature for 16 hours. The reaction mixture was poured into an aqueous solution of ammonium chloride (50 mL) and the mixture extracted with dichloromethane (3×100 mL). The combined organic phase was then washed with water (50 mL) and brine (50 mL) and the organic phase dried over magnesium sulfate, filtered, and concentrated under reduced pressure. The resulting residue was purified by silica gel column chromatography (eluting with 2% to 10% methanol/dichloromethane) to afford the title compound (60 mg).

MS (ESI) m/z 481.1 [M+H]$^+$

B: 1-(2-Fluoro-4-((1-(4-(1,1,1,3,3,3-hexafluoro-2-hydroxypropan-2-yl)benzyl)piperidin-4-yl)(hydroxy)methyl)phenyl)-3-((S)-tetrahydrofuran-3-yl)urea 2-(4-((4-((4-Amino-3-fluorophenyl)(hydroxy)methyl)piperidin-1-yl)methyl)phenyl)-1,1,1,3,3,3-hexafluoropropan-2-ol (0.125 mmol, 60 mg) and 4-nitrophenyl chloroformate (0.125 mmol, 25.2 mg) were combined in tetrahydrofuran (2 mL) and the reaction stirred at room temperature for 1 hour. (S)-Tetrahydrofuran-3-amine hydrochloride (0.125 mmol, 15.43 mg) and triethylamine (0.500 mmol, 50.6 mg) were added and the mixture stirred at room temperature overnight. The mixture was concentrated under reduced pressure and the resulting residue purified by silica gel column chromatography (eluting with dichloromethane to 10% methanol/dichloromethane) to afford the title compound (13 mg). MS (ESI) m/z 594.7 [M+H]$^+$

Example 27

1-(4-(1-(1-(4-(1,1,1,3,3,3-Hexafluoro-2-hydroxypropan-2-yl)benzyl)piperidin-4-yl)-1-hydroxyethyl)phenyl)-3-(2-hydroxy-2-methylpropyl)urea

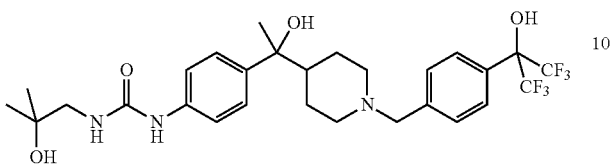

A: N-(4-(1-(4-(1,1,1,3,3,3-Hexafluoro-2-hydroxypropan-2-yl)benzyl)piperidine-4-carbonyl)phenyl)acetamide To a stirred mixture of N-(4-(piperidine-4-carbonyl)phenyl)acetamide (3.82 mmol, 0.94 g) and potassium carbonate (11.45 mmol, 1.582 g) in N-methyl-2-pyrrolidinone (5 mL) was added 2-(4-(bromomethyl)phenyl)-1,1,1,3,3,3-hexafluoropropan-2-ol (3.82 mmol, 1.286 g). The reaction was stirred at room temperature over the weekend. Methanol (30 mL) was added and the reaction was filtered. The filtrate was purified by strong cation exchange column chromatography to afford the title compound (1.51 g).
MS (ESI) m/z 503.0 [M+H]$^+$

B: N-(4-(1-(1-(4-(1,1,1,3,3,3-Hexafluoro-2-hydroxypropan-2-yl)benzyl)piperidin-4-yl)-1-hydroxyethyl)phenyl)acetamide N-(4-(1-(4-(1,1,1,3,3,3-Hexafluoro-2-hydroxypropan-2-yl)benzyl)piperidine-4-carbonyl)phenyl)acetamide (1.702 mmol, 855 mg) was dissolved in anhydrous tetrahydrofuran (20 mL) under nitrogen and cooled to −78° C. 3M Methylmagnesium bromide in diethyl ether (3.40 mmol, 1.134 mL) was added and the mixture stirred at −78° C. for 30 minutes before allowing to warm to room temperature and stirring for a further 4 hours. After this time, further 3M methylmagnesium bromide in diethyl ether (3.40 mmol, 1.134 mL) was added and the mixture stirred for 2 hours. The mixture was cooled to 0° C. and quenched with a saturated solution of ammonium chloride (30 mL). The mixture was extracted with ethyl acetate (100 mL) and washed with water (30 mL) then brine (30 mL). The organics were dried over magnesium sulfate, filtered and concentrated under reduced pressure. The resulting residue was purified by silica gel column chromatography (eluting with dichloromethane to 15% methanol/dichloromethane) to afford the title compound (300 mg). MS (ESI) m/z 519.2 [M+H]$^+$

C: 2-(4-((4-(1-(4-Aminophenyl)-1-hydroxyethyl)piperidin-1-yl)methyl)phenyl)-1,1,1,3,3,3-hexafluoropropan-2-ol N-(4-(1-(1-(4-(1,1,1,3,3,3-Hexafluoro-2-hydroxypropan-2-yl)benzyl)piperidin-4-yl)-1-hydroxyethyl)phenyl)acetamide (0.482 mmol, 250 mg) was dissolved in ethanol (5 mL) and 2M hydrochloric acid (12.00 mmol, 6 mL) added. The mixture was heated to 100° C. for 5 hours then cooled. The mixture was purified by strong cation exchange column chromatography and concentrated under reduced pressure. The resulting residue was purified by silica gel column chromatography (eluting with dichloromethane to 10% methanol/dichloromethane) to afford the title compound (120 mg). MS (ESI) m/z 477.2 [M+H]$^+$

D: 1-(4-(1-(1-(4-(1,1,1,3,3,3-Hexafluoro-2-hydroxypropan-2-yl)benzyl)piperidin-4-yl)-1-hydroxyethyl)phenyl)-3-(2-hydroxy-2-methylpropyl)urea 2-(4-((4-(1-(4-Aminophenyl)-1-hydroxyethyl)piperidin-1-yl)methyl)phenyl)-1,1,1,3,3,3-hexafluoropropan-2-ol (0.252 mmol, 120 mg) and 4-nitrophenyl chloroformate (0.252 mmol, 50.8 mg) were combined in tetrahydrofuran (2 mL) and the reaction stirred at room temperature for 1 hour. 1-Amino-2-methylpropan-2-ol (0.252 mmol, 22.45 mg) and triethylamine (0.756 mmol, 76 mg) were added and the mixture stirred at room temperature overnight. The mixture was concentrated under reduced pressure and the resulting residue purified by HPLC then treated with strong cation exchange column chromatography. The resulting product was purified by silica gel column chromatography (eluting with 2% to 15% methanol/dichloromethane) to afford the title compound (5 mg). MS (ESI) m/z 592.2 [M+H]$^+$

Example 28

1-(4-(1-(1-(4-(1,1,1,3,3,3-Hexafluoro-2-hydroxypropan-2-yl)benzyl)piperidin-4-yl)-1-methoxyethyl)phenyl)-3-(2-hydroxy-2-methylpropyl)urea

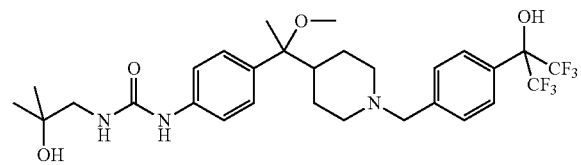 [SMILES: COC(C)(c1ccc(NC(=O)NCC(C)(C)O)cc1)C1CCN(Cc2ccc(C(O)(C(F)(F)F)C(F)(F)F)cc2)CC1]

A: N-(4-(1-(1-(4-(1,1,1,3,3,3-Hexafluoro-2-hydroxypropan-2-yl)benzyl)piperidin-4-yl)-1-hydroxyethyl)phenyl)acetamide N-(4-(1-(4-(1,1,1,3,3,3-Hexafluoro-2-hydroxypropan-2-yl)benzyl)piperidine-4-carbonyl)phenyl)acetamide (1.702 mmol, 855 mg) was dissolved in anhydrous tetrahydrofuran (20 mL) under nitrogen and cooled to −78° C. 3M methylmagnesium bromide in diethyl ether (3.40 mmol, 1.134 mL) was added and the mixture stirred at −78° C. for 30 minutes before allowing to warm to room temperature and stirring for a further 4 hours. After this time, further 3M methylmagnesium bromide in diethyl ether (3.40 mmol, 1.134 mL) was added and the mixture stirred for 2 hours. The mixture was cooled to 0° C. and quenched with a saturated solution of ammonium chloride (30 mL). The mixture was extracted with ethyl acetate (100 mL) and washed with water (30 mL) then brine (30 mL). The organics were dried over magnesium sulfate, filtered and concentrated under reduced pressure. The resulting residue was purified by silica gel column chromatography (eluting with dichloromethane to 15% methanol/dichloromethane) to afford the title compound (300 mg). MS (ESI) m/z 519.2 [M+H]$^+$ B: 2-(4-((4-(1-(4-Aminophenyl)-1-hydroxyethyl)piperidin-1-yl)methyl)phenyl)-1,1,1,3,3,3-hexafluoropropan-2-ol N-(4-(1-(1-(4-(1,1,1,3,3,3-Hexafluoro-2-hydroxypropan-2-yl)benzyl)piperidin-4-yl)-1-hydroxyethyl)phenyl)acetamide (0.482 mmol, 250 mg) was dissolved in ethanol (5 mL) and 2M hydrochloric acid (12.00 mmol, 6 mL) added. The mixture was heated to 100° C. for 5 hours then cooled. The mixture was purified by strong cation exchange column chromatography and concentrated under reduced pressure. The resulting residue was purified by silica gel column chromatography (eluting with dichloromethane to 10% methanol/dichloromethane) to afford the title compound (120 mg). MS (ESI) m/z 477.2 [M+H]$^+$ C: 1-(4-(1-(1-(4-(1,1,1,3,3,3-Hexafluoro-2-hydroxypropan-2-yl)benzyl)piperidin-4-yl)-1-methoxyethyl)phenyl)-3-(2-hydroxy-2-methylpropyl)urea 2-(4-((4-(1-(4-Aminophenyl)-1-hydroxyethyl)piperidin-1-yl)methyl)phenyl)-1,1,1,3,3,3-hexafluoropropan-2-ol (0.252 mmol, 120 mg) and 4-nitrophenyl chloroformate (0.252 mmol, 50.8 mg) were combined in tetrahydrofuran (2 mL) and the reaction stirred at room temperature for 1 hour. 1-Amino-2-methylpropan-2-ol (0.252 mmol, 22.45 mg) and triethylamine (0.756 mmol, 76 mg) were added and the mixture stirred at room temperature overnight. The mixture was concentrated under reduced pressure and the resulting residue purified by HPLC then treated with strong cation exchange column chromatography. The resulting product was purified by silica gel column chromatography (eluting with 2% to 15% methanol/dichloromethane) to afford the title compound (40 mg). MS (ESI) m/z 606.2 [M+H]$^+$ Example 29

1-(4-(1-(1-(4-(1,1,1,3,3,3-Hexafluoro-2-hydroxypropan-2-yl)benzyl)piperidin-4-yl)ethyl)phenyl)-3-(2-hydroxy-2-methylpropyl)urea

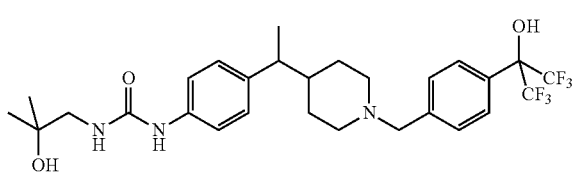 [SMILES: CC(c1ccc(NC(=O)NCC(C)(C)O)cc1)C1CCN(Cc2ccc(C(O)(C(F)(F)F)C(F)(F)F)cc2)CC1]

A: 2-(4-((4-(1-(4-Aminophenyl)ethylidene)piperidin-14)methyl)phenyl)-1,1,1,3,3,3-hexafluoropropan-2-ol N-(4-(1-(1-(4-(1,1,1,3,3,3-Hexafluoro-2-hydroxypropan-2-yl)benzyl)piperidin-4-yl)-1-hydroxyethyl)phenyl)acetamide (0.482 mmol, 250 mg) was dissolved in ethanol (5 mL) and 2M hydrochloric acid (12.00 mmol, 6 ml) added. The mixture was heated to 100° C. for 5 hours then cooled. The mixture was purified by strong cation exchange column chromatography and concentrated under reduced pressure. The resulting residue was purified by silica gel column chromatography (eluting with dichloromethane to 10% methanol/dichloromethane) to afford the title compound (100 mg). MS (ESI) m/z 459.0 [M+H]$^+$ B: 1-(4-(1-(1-(4-(1,1,1,3,3,3-Hexafluoro-2-hydroxypropan-2-yl)benzyl)piperidin-4-yl)ethyl)phenyl)-3-(2-hydroxy-2-methylpropyl)urea 2-(4-((4-(1-(4-Aminophenyl)ethyl)piperidin-1-yl)methyl)phenyl)-1,1,1,3,3,3-hexafluoro-propan-2-ol (0.178 mmol, 82 mg) and 4-nitrophenyl chloroformate (0.178 mmol, 35.9 mg) were combined in tetrahydrofuran (2 mL) and the reaction stirred at room temperature for 1 hour. 1-Amino-2-methylpropan-2-ol (0.178 mmol, 15.87 mg) and triethylamine (0.534 mmol, 54.1 mg) were added and the mixture stirred at room temperature overnight. The mixture was concentrated under reduced pressure and the resulting residue purified by silica gel column chromatography (eluting with dichloromethane to 10% methanol/dichloromethane) to afford the title compound (16 mg). MS (ESI) m/z 576.2 [M+H]$^+$ Example 30

1-(4-(1-(4-(1,1,1,3,3,3-Hexafluoro-2-hydroxypropan-2-yl)benzyl)piperidine-4-carbonyl)phenyl)-3-(oxetan-3-yl)urea

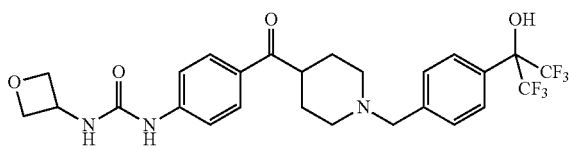 [SMILES: O=C(Nc1ccc(C(=O)C2CCN(Cc3ccc(C(O)(C(F)(F)F)C(F)(F)F)cc3)CC2)cc1)NC1COC1]

A: (4-Aminophenyl)(1-(4-(1,1,1,3,3,3-hexafluoro-2-hydroxypropan-2-yl)benzyl)piperidin-4-yl)methanone N-(4-(1-(4-(1,1,1,3,3,3-Hexafluoro-2-hydroxypropan-2-yl)benzyl)piperidine-4-carbonyl)phenyl)acetamide (1.128 mmol, 567 mg) was dissolved in ethanol (20 mL) and 2M hydrochloric acid (56.4 mmol, 28.2 mL) added. The mixture was heated to 100° C. overnight and cooled. The mixture was purified by strong cation exchange column chromatography and concentrated under reduced pressure to afford the title compound (338 mg). MS (ESI) m/z 461.2 [M+H]$^+$ B: 1-(4-(1-(4-(1,1,1,3,3,3-Hexafluoro-2-hydroxypropan-2-yl)benzyl)piperidine-4-carbonyl)phenyl)-3-(oxetan-3-yl)urea (4-Aminophenyl)(1-(4-(1,1,1,3,3,3-hexafluoro-2-hydroxypropan-2-yl)benzyl)piperidin-4-yl)methanone (0.367 mmol, 169 mg) and 4-nitrophenyl chloroformate (0.367 mmol, 74.0 mg) were combined in tetrahydrofuran (2 mL) and stirred at room temperature for 1 hour. Oxetan-3-amine (0.734 mmol, 53.7 mg) and triethylamine (1.101 mmol, 111 mg) were added and the mixture stirred at room temperature overnight. The mixture was concentrated under reduced pressure and the resulting residue purified by basic HPLC to afford the title compound (43 mg). MS (ESI) m/z 560.2 [M+H]$^+$.

The following compound was prepared in a similar manner:

30B: 1-(4-(1-(4-(1,1,1,3,3,3-Hexafluoro-2-hydroxypropan-2-yl)benzyl)piperidine-4-carbonyl)phenyl)-3-(2-hydroxy-2-methylpropyl)urea

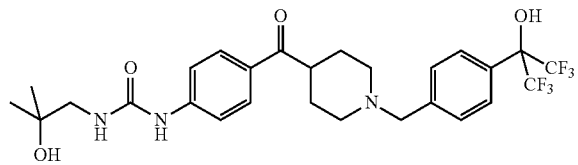 [SMILES: CC(C)(O)CNC(=O)Nc1ccc(C(=O)C2CCN(Cc3ccc(C(O)(C(F)(F)F)C(F)(F)F)cc3)CC2)cc1]

MS (ESI) m/z 576.2 [M+H]+

Example 31

1-(4-((1-(4-(1,1,1,3,3,3-Hexafluoro-2-hydroxypropan-2-yl)benzyl)piperidin-4-yl)(methyl)amino)phenyl)-3-(pyridin-4-yl)urea

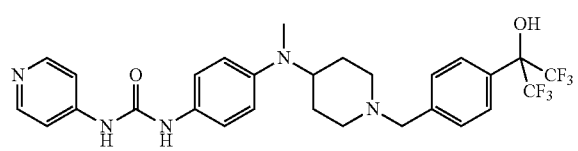 [SMILES: CN(c1ccc(NC(=O)Nc2ccncc2)cc1)C1CCN(Cc2ccc(C(O)(C(F)(F)F)C(F)(F)F)cc2)CC1]

A: N1-Methyl-N1-(piperidin-4-yl)benzene-1,4-diamine

Step 1: A mixture of 1-fluoro-4-nitrobenzene (12.24 mmol, 1.726 g), 1-benzyl-N-methylpiperidin-4-amine (12.24 mmol, 2.5 g) and potassium carbonate (12.24 mmol, 1.691 g) was heated at 100° C. using an oil bath for 48 hours. The reaction mixture was allowed to cool to room temperature, diluted with dichloromethane and filtered. The filtrate was concentrated under vacuum to give the intermediate 1-benzyl-N-methyl-N-(4-nitrophenyl)piperidin-4-amine (3.8 g).

Step 2: 1-Benzyl-N-methyl-N-(4-nitrophenyl)piperidin-4-amine (11.68 mmol, 3.8 g) and palladium on carbon (degussa) (0.117 mmol, 0.249 g) were hydrogenated in methanol (50 mL)/ethyl acetate (20 mL) at 5 bar at room temperature overnight. The reaction mixture was filtered through celite and concentrated under vacuum to give the title compound (2.6 g). MS (ESI) m/z 206.1 [M+H]+

B: 2-(4-((4-((4-Aminophenyl)(methyl)amino)piperidin-1-yl)methyl)phenyl)-1,1,1,3,3,3-hexafluoropropan-2-ol 2-(4-(Bromomethyl)phenyl)-1,1,1,3,3,3-hexafluoropropan-2-ol (1.948 mmol, 0.657 g), N1-methyl-N1-(piperidin-4-yl)benzene-1,4-diamine (1.948 mmol, 0.4 g) and potassium carbonate (5.84 mmol, 0.808 g) were combined and stirred at room temperature for 1 hour in acetonitrile (50 mL). The reaction mixture was filtered and concentrated under vacuum. The residue was dissolved in ethyl acetate and washed with saturated sodium bicarbonate solution. The organic layer was separated, dried and concentrated under vacuum. The residue was purified by silica column chromatography (eluent: dichloromethane to 8% methanol in dichloromethane) to afford the title compound (260 mg). MS (ESI) m/z 462.4 [M+H]+

C: 1-(4-((1-(4-(1,1,1,3,3,3-Hexafluoro-2-hydroxypropan-2-yl)benzyl)piperidin-4-yl)(methyl)amino)phenyl)-3-(pyridin-4-yl)urea 2-(4-((4-((4-Aminophenyl)(methyl)amino)piperidin-1-yl)methyl)phenyl)-1,1,1,3,3,3-hexafluoropropan-2-ol (0.260 mmol, 120 mg) and phenyl pyridin-4-ylcarbamate (0.390 mmol, 84 mg) were combined in tetrahydrofuran (1 mL) and dioxane (1 mL) and heated to 100° C. overnight. The reaction mixture was concentrated under vacuum. The residue was purified by prep-HPLC (acidic conditions) and SCX chromatography to give the title compound (44.2 mg). MS (ESI) m/z 582.2 [M+H]+

Example 32

1-(4-((1-(4-(1,1,1,3,3,3-Hexafluoro-2-hydroxypropan-2-yl)benzyl)piperidin-4-yl)(methyl)amino)phenyl)-3-(tetrahydro-2H-pyran-4-yl)urea

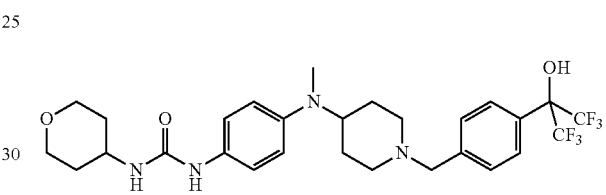

A solution of 2-(4-((4-((4-aminophenyl)(methyl)amino)piperidin-1-yl)methyl)phenyl)-1,1,1,3,3,3-hexafluoropropan-2-ol (0.303 mmol, 140 mg) and 4-nitrophenyl carbonochloridate (0.303 mmol, 61.2 mg) in dichloromethane (1 mL) was stirred at room temperature for 30 minutes. Tetrahydro-2H-pyran-4-amine (0.607 mmol, 61.4 mg) was added followed by triethylamine (0.910 mmol, 0.127 mL, 92 mg) and the reaction stirred at room temperature overnight. The reaction mixture was diluted with dichloromethane/saturated sodium bicarbonate solution and filtered through a hydrophobic frit. The organic layer was concentrated and the residue was purified by silica column chromatography (eluent: dichloromethane to 4% methanol in dichloromethane) to give the title compound (74.2 mg). MS (ESI) m/z 589.2 [M+H]+

Example 33

1-(3-Fluoro-4-((1-(4-(1,1,1,3,3,3-hexafluoro-2-hydroxypropan-2-yl)benzyl)piperidin-4-yl)(methyl)amino)phenyl)-3-(pyridin-4-yl)urea

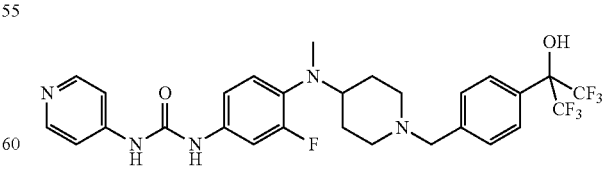

Step 1: tert-Butyl 4-((2-fluoro-4-nitrophenyl)(methyl)amino)piperidine-1-carboxylate (2.83 mmol, 1 g) was dissolved in dichloromethane (10 mL). Trifluoroacetic acid (3 mL) was added and the reaction mixture stirred at room temperature for 30 minutes. The reaction mixture was concentrated under vacuum and purified by SCX chromatography to afford the intermediate N-(2-fluoro-4-nitrophenyl)-N-methylpiperidin-4-amine (600 mg).

Step 2: 2-(4-(Bromomethyl)phenyl)-1,1,1,3,3,3-hexafluoropropan-2-ol (2.369 mmol, 1.141 mL, 798 mg), N-(2-fluoro-4-nitrophenyl)-N-methylpiperidin-4-amine (2.369 mmol, 600 mg) and potassium carbonate (7.11 mmol, 982 mg) were combined and stirred at 70° C. overnight in acetonitrile (50 mL). The reaction mixture was filtered and concentrated under vacuum. The residue was dissolved in ethyl acetate and washed with saturated sodium bicarbonate solution. The organic layer was separated, dried over magnesium sulfate and concentrated under vacuum to give the intermediate 1,1,1,3,3,3-hexafluoro-2-(4-((4-((2-fluoro-4-nitrophenyl)(methyl)amino)piperidin-1-yl)methyl)phenyl)propan-2-ol (1.5 g).

Step 3: 1,1,1,3,3,3-Hexafluoro-2-(4-((4-((2-fluoro-4-nitrophenyl)(methyl)amino)-piperidin-1-yl)methyl)phenyl)propan-2-ol (1.472 mmol, 750 mg) and palladium (10% on carbon, Degussa) (0.015 mmol, 31.3 mg) were hydrogenated in ethyl acetate (10 mL) at 5 bar for 1 hour at room temperature. The reaction mixture was filtered and concentrated under vacuum to give the intermediate 2-(4-((4-((4-amino-2-fluorophenyl)-(methyl)amino)piperidin-1-yl)methyl)phenyl)-1,1,1,3,3,3-hexafluoropropan-2-ol (300 mg).

Step 4: 2-(4-((4-((4-Amino-2-fluorophenyl)(methyl)amino)piperidin-1-yl)methyl)-phenyl)-1,1,1,3,3,3-hexafluoropropan-2-ol (0.209 mmol, 100 mg) and phenyl pyridin-4-ylcarbamate (0.313 mmol, 67.0 mg) were combined in tetrahydrofuran (1 mL) and dioxane (1 mL) and heated to 80° C. overnight. The reaction mixture was concentrated under vacuum. The residue was purified by prep-HPLC (acidic conditions) and SCX chromatography to afford title compound (83.9 mg). MS (ESI) m/z 600.2 [M+H]$^+$ Example 34

1-(3-(1-(4-(1,1,1,3,3,3-Hexafluoro-2-hydroxypropan-2-yl)benzyl)piperidin-4-yloxy)phenyl)-3-(2-hydroxy-2-methylpropyl)urea

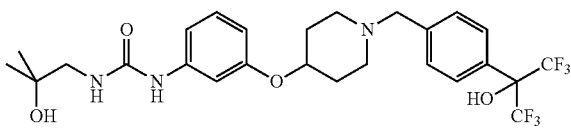 [SMILES: CC(C)(O)CNC(=O)Nc1cccc(OC2CCN(Cc3ccc(C(O)(C(F)(F)F)C(F)(F)F)cc3)CC2)c1]

A: 1,1,1,3,3,3-Hexafluoro-2-(4-((4-(3-nitrophenoxy)piperidin-1-yl)methyl)phenyl)propan-2-ol To a stirred mixture of 4-(3-nitrophenoxy)piperidine hydrochloride (11.87 mmol, 3.07 g) and triethylamine (35.6 mmol, 4.96 mL, 3.60 g) in dichloromethane was added 2-(4-(bromomethyl)phenyl)-1,1,1,3,3,3-hexafluoropropan-2-ol (11.87 mmol, 4.00 g). The reaction was stirred for 20 hours then was filtered. The filtrate was chromatographed on silica (eluting with a gradient of dichloromethane to ethyl acetate) to give the title compound (4 g). MS (ESI) m/z 479.0 [M+H]$^+$ B: 2-(4-((4-(3-Aminophenoxy)piperidin-1-yl)methyl)phenyl)-1,1,1,3,3,3-hexafluoropropan-2-ol A mixture of 1,1,1,3,3,3-hexafluoro-2-(4-((4-(3-nitrophenoxy)piperidin-1-yl)methyl)-phenyl)propan-2-ol (8.36 mmol, 4 g) and palladium on carbon (10%) (0.251 mmol, 0.267 g) in ethyl acetate was hydrogenated at 3 bar until the desired amount of hydrogen was consumed. The reaction was filtered through celite and concentrated under reduced pressure. Chromatography on silica, eluting with ethyl acetate, gave the title compound (3.7 g). MS (ESI) m/z 449.2 [M+H]$^+$ C: 1-(3-(1-(4-(1,1,1,3,3,3-Hexafluoro-2-hydroxypropan-2-yl)benzyl)piperidin-4-yloxy)phenyl)-3-(2-hydroxy-2-methylpropyl)urea To a stirred solution of 2-(4-((4-(3-aminophenoxy)piperidin-1-yl)methyl)phenyl)-1,1,1,3,3,3-hexafluoropropan-2-ol (1.115 mmol, 500 mg) in dichloromethane was added 4-nitrophenyl carbonochloridate (1.115 mmol, 225 mg) followed by triethylamine (1.115 mmol, 155 μl, 113 mg). The reaction was stirred for 30 minutes then 1-amino-2-methylpropan-2-ol (2.230 mmol, 199 mg) was added. The reaction was stirred for 2 hours then was chromatographed on silica (eluting with a gradient of dichloromethane to dichloromethane/methanol (8%)) to give the title compound (300 mg). MS (ESI) m/z 564.2 [M+H]$^+$ Example 35

1-(Cyclopropylmethyl)-3-(3-((1-(4-(1,1,1,3,3,3-hexafluoro-2-hydroxypropan-2-yl)benzyl)piperidin-4-yl)methyl)phenyl)urea

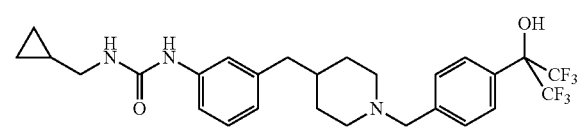 [SMILES: O=C(NCC1CC1)Nc1cccc(CC2CCN(Cc3ccc(C(O)(C(F)(F)F)C(F)(F)F)cc3)CC2)c1]

A: Diethyl 3-nitrobenzylphosphonate

A stirring suspension of 1-(bromomethyl)-3-nitrobenzene (46.3 mmol, 10 g) in triethyl phosphite (69.4 mmol, 12.08 mL, 11.54 g) was heated at 100° C. for 4 hours. The reaction mixture was cooled to room temperature and partitioned between water and dichloromethane. The organic layer was separated, dried and concentrated under vacuum. The residue was purified by silica column chromatography (eluent: 0-5% methanol in dichloromethane) to afford the title compound (8 g).

MS (ESI) m/z 274.0 [M+H]$^+$

B: tert-Butyl 4-(3-aminobenzyl)piperidine-1-carboxylate

Step 1: A suspension of sodium hydride (10.98 mmol, 0.439 g) in tetrahydrofuran (40 mL) was added to a stirred solution of diethyl 3-nitrobenzylphosphonate (7.32 mmol, 2 g) in tetrahydrofuran (40 mL) at 0° C. and the reaction stirred for 30 minutes. tert-Butyl 4-oxopiperidine-1-carboxylate (7.32 mmol, 1.459 g) was added and the reaction mixture stirred at room temperature overnight. The reaction mixture was concentrated under vacuum and the residue partitioned between dichloromethane and water. The organic layer was separated, dried and concentrated under vacuum. The residue was purified by silica column chromatography (eluent: 0-2% methanol in dichloromethane) to afford the intermediate tert-butyl 4-(3-nitrobenzylidene)-piperidine-1-carboxylate (2 g).

Step 2: tert-Butyl 4-(3-nitrobenzylidene)piperidine-1-carboxylate (6.28 mmol, 2 g) was hydrogenated with palladium on carbon (10%) (0.126 mmol, 0.134 g) in ethanol at 3 bar for 1.5 hours. The reaction mixture was filtered through celite and concentrated under vacuum to afford the title compound (1.77 g). MS (ESI) m/z 291.3 [M+H]+

C: 2-(4-((4-(3-Aminobenzyl)piperidin-1-yl)methyl)phenyl)-1,1,1,3,3,3-hexafluoropropan-2-ol Step 1: tert-Butyl 4-(3-aminobenzyl)piperidine-1-carboxylate (6.09 mmol, 1.77 g) was dissolved in dichloromethane (10 mL). Trifluoroacetic acid (5 mL) was added and the reaction mixture stirred at room temperature for 1 hour. The reaction mixture was concentrated under vacuum and purified by SCX chromatography to afford the intermediate 3-(piperidin-4-ylmethyl)aniline (1.27 g).

Step 2: 3-(Piperidin-4-ylmethyl)aniline (6.67 mmol, 1.27 g), 2-(4-(bromomethyl)-phenyl)-1,1,1,3,3,3-hexafluoropropan-2-ol (6.67 mmol, 2.250 g) and potassium carbonate (13.35 mmol, 1.845 g) were combined and stirred at room temperature in acetonitrile (20 mL) for 1 hour. The reaction mixture was filtered and filtrate was concentrated under vacuum. The residue was purified by silica column chromatography (eluent: 5-6% methanol in dichloromethane) to afford the title compound (900 mg). MS (ESI) m/z 447.0 [M+H]+

D: 1-(Cyclopropylmethyl)-3-(3-((1-(4-(1,1,1,3,3,3-hexafluoro-2-hydroxypropan-2-yl)benzyl)piperidin-4-yl)methyl)phenyl)urea A solution of 2-(4-((4-(3-aminobenzyl)piperidin-1-yl)methyl)phenyl)-1,1,1,3,3,3-hexafluoropropan-2-ol (0.224 mmol, 100 mg) and 4-nitrophenyl carbonochloridate (0.224 mmol, 45.1 mg) in tetrahydrofuran (5 mL) was stirred at room temperature for 30 minutes. Cyclopropylmethanamine (0.453 mmol, 46 µL, 32.2 mg) was added and the reaction was kept at room temperature overnight. The reaction mixture was concentrated under vacuum and residue purified by silica column chromatography (eluent: 2-10% methanol in dichloromethane) to afford the title compound (99 mg).
MS (ESI) m/z 544.2 [M+H]+

Example 36

1-(1-(1-(4-(1,1,1,3,3,3-Hexafluoro-2-hydroxypropan-2-yl)benzyl)piperidin-4-yl)-1H-benzo[d]imidazol-6-yl)-3-(pyridin-4-yl)urea

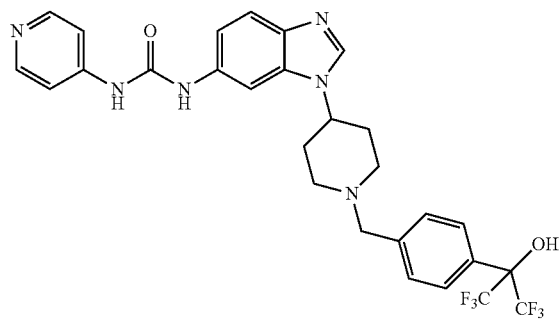 [SMILES: O=C(Nc1ccncc1)Nc1ccc2ncn(C3CCN(Cc4ccc(C(O)(C(F)(F)F)C(F)(F)F)cc4)CC3)c2c1]

A: tert-Butyl 4-(6-amino-1H-benzo[d]imidazol-1-yl)piperidine-1-carboxylate

Step 1: tert-Butyl 4-(methylsulfonyloxy)piperidine-1-carboxylate (30.6 mmol, 8.56 g), potassium carbonate (61.3 mmol, 8.47 g) and 5-nitro-1H-benzo[d]imidazole (30.6 mmol, 5 g) were combined and heated to 100° C. in N,N-dimethylformamide (30 mL) overnight. The reaction mixture was diluted with ethyl acetate and washed with water. The organic phase was dried over sodium sulfate and concentrated at reduced pressure to afford a mixture of the intermediate regioisomers tert-butyl 4-(6-nitro-1H-benzo[d]imidazol-1-yl)piperidine-1-carboxylate and tert-butyl 4-(6-nitro-1H-benzo[d]imidazol-1-yl)piperidine-1-carboxylate (5 g). MS (ESI) m/z 347.1 [M+H]+

Step 2: A mixture of regioisomers tert-butyl 4-(5-nitro-1H-benzo[d]imidazol-1-yl)piperidine-1-carboxylate and tert-butyl 4-(6-nitro-1H-benzo[d]imidazol-1-yl)piperidine-1-carboxylate (14.58 mmol, 5.05 g) and 10% palladium on carbon (0.5 g) were stirred under a hydrogen atmosphere in ethanol (50 mL) at 5 atmospheres for 1 hour. The catalyst was filtered off and the filtrate concentrated at reduced pressure. The resulting residue was purified by silica chromatography (eluting with a solvent gradient from dichloromethane to 5% methanol/dichloromethane) to afford the title compound (1.799 g). MS (ESI) m/z 317.1 [M+H]+

B: 1-(Piperidin-4-yl)-1H-benzo[d]imidazol-6-amine

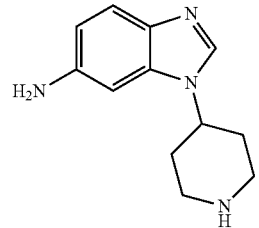 [SMILES: Nc1ccc2ncn(C3CCNCC3)c2c1]

tert-Butyl 4-(6-amino-1H-benzo[d]imidazol-1-yl)piperidine-1-carboxylate (5.69 mmol, 1.799 g) was stirred in dichloromethane (5 mL)/trifluoroacetic acid (5 mL) for 1 hour at room temperature. The reaction was concentrated at reduced pressure and passed down an SCX column to afford the title compound (1.01 g). MS (ESI) m/z 217.1 [M+H]+

C: 2-(4-((4-(6-Amino-1H-benzo[d]imidazol-1-yl)piperidin-1-yl)methyl)phenyl)-1,1,1,3,3,3-hexafluoropropan-2-ol

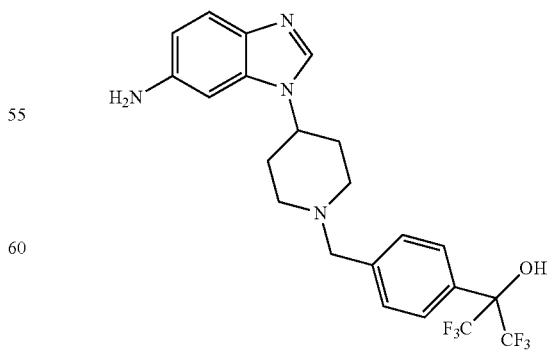

1-(Piperidin-4-yl)-1H-benzo[d]imidazol-6-amine (4.62 mmol, 1 g), 2-(4-(bromomethyl)phenyl)-1,1,1,3,3,3- hexafluoropropan-2-ol (4.62 mmol, 1.558 g) and potassium carbonate (9.25 mmol, 1.278 g) were combined and stirred in acetonitrile (25 mL) at room temperature for 3 days. The reaction mixture was concentrated at reduced pressure, taken up in dichloromethane, washed with water and concentrated under vacuum. The resulting residue was purified by silica chromatography (eluting with a solvent gradient from dichloromethane to 6% methanol/dichloromethane) to afford the title compound (784 mg). MS (ESI) m/z 473.2 [M+H]$^+$ D: 1-(1-(1-(4-(1,1,1,3,3,3-Hexafluoro-2-hydroxypropan-2-yl)benzyl)piperidin-4-yl)-1H-benzo[d]imidazol-6-yl)-3-(pyridin-4-yl)urea 2-(4-((4-(6-Amino-1H-benzo[d]imidazol-1-yl)piperidin-1-yl)methyl)phenyl)-1,1,1,3,3,3-hexafluoropropan-2-ol (0.212 mmol, 0.1 g) and phenyl pyridin-4-ylcarbamate (0.318 mmol, 0.068 g) were combined and heated in a Reactivial in dioxane (2 mL) for 2 days. The solvent was removed and the resulting residue purified by silica chromatography (eluting with a solvent gradient from dichloromethane to 8% methanol/dichloromethane) to afford the title compound (16 mg). MS (ESI) m/z 593.2 [M+H]$^+$ Example 37

1-(1-(1-(4-(1,1,1,3,3,3-Hexafluoro-2-hydroxypropan-2-yl)benzyl)piperidin-4-yl)-1H-benzo[d]imidazol-5-yl)-3-(pyridin-4-yl)urea

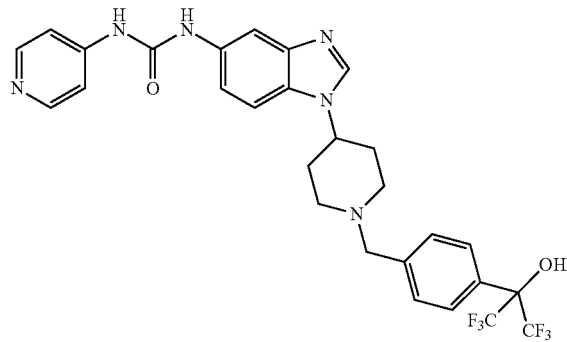 [SMILES: O=C(Nc1ccncc1)Nc1ccc2c(c1)ncn2C1CCN(Cc2ccc(C(O)(C(F)(F)F)C(F)(F)F)cc2)CC1]

A: tert-Butyl 4-(5-amino-1H-benzo[d]imidazol-1-yl)piperidine-1-carboxylate

Step 1: tert-Butyl 4-(methylsulfonyloxy)piperidine-1-carboxylate (30.6 mmol, 8.56 g), potassium carbonate (61.3 mmol, 8.47 g) and 5-nitro-1H-benzo[d]imidazole (30.6 mmol, 5 g) were combined and heated to 100° C. in N,N-dimethylformamide (30 mL) overnight. The reaction mixture was diluted with ethyl acetate and washed with water. The organic was dried over sodium sulfate and concentrated at reduced pressure to afford a mixture of the intermediate regioisomers tert-butyl 4-(6-nitro-1H-benzo[d]imidazol-1-yl)piperidine-1-carboxylate and tert-butyl 4-(6-nitro-1H-benzo[d]imidazol-1-yl)piperidine-1-carboxylate (5 g). MS (ESI) m/z 347.1 [M+H]$^+$ Step 2: A mixture of regioisomers tert-butyl 4-(5-nitro-1H-benzo[d]imidazol-1-yl)-piperidine-1-carboxylate and tert-butyl 4-(6-nitro-1H-benzo[d]imidazol-1-yl)piperidine-1-carboxylate (14.58 mmol, 5.05 g) and 10% palladium on carbon (0.5 g) were stirred under a hydrogen atmosphere in ethanol (50 mL) at 5 atmospheres for 1 hour. The catalyst was filtered off and the filtrate concentrated at reduced pressure. The resulting residue was purified by silica chromatography (eluting with a solvent gradient from dichloromethane to 5% methanol/dichloromethane). Fractions were collected and combined to afford the title compound (1.187 g). MS (ESI) m/z 317.1 [M+H]$^+$ B: 1-(Piperidin-4-yl)-1H-benzo[d]imidazol-5-amine

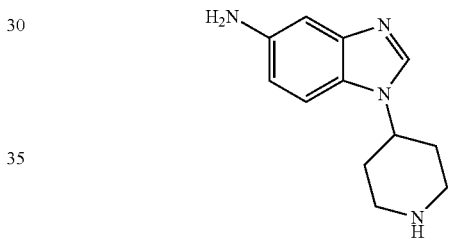

tert-Butyl 4-(5-amino-1H-benzo[d]imidazol-1-yl)piperidine-1-carboxylate (3.75 mmol, 1.187 g) was stirred in dichloromethane (5 mL)/trifluoroacetic acid (5 mL) for 1 hour at room temperature. The reaction was concentrated under vacuum and passed down an SCX column to afford the title compound (1.042 g). MS (ESI) m/z 217.1 [M+H]$^+$ C: 2-(4-((4-(5-Amino-1H-benzo[d]imidazol-1-yl)piperidin-1-yl)methyl)phenyl)-1,1,1,3,3,3-hexafluoropropan-2-ol

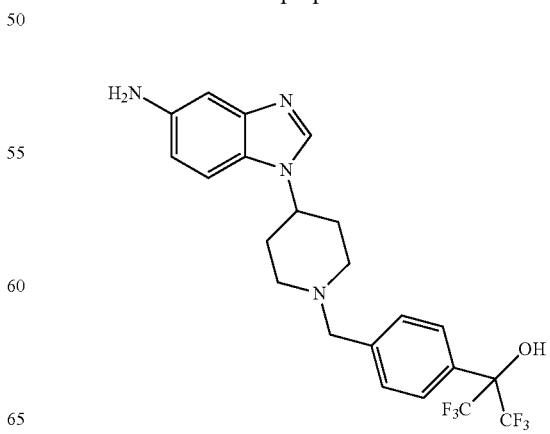

1-(Piperidin-4-yl)-1H-benzo[d]imidazol-5-amine, 2-(4-(bromomethyl)phenyl)-1,1,1,3,3,3-hexafluoropropan-2-ol (4.82 mmol, 1.624 g) and potassium carbonate (9.64 mmol, 1.332 g) were combined and stirred in acetonitrile (25 mL) at room temperature for 3 days. The reaction mixture was concentrated under vacuum, taken up in dichloromethane, washed with water and concentrated under vacuum. The resulting residue was purified by silica chromatography (eluting with a solvent gradient from dichloromethane to 6% methanol/dichloromethane) to afford the title compound (594 mg). MS (ESI) m/z 473.0 [M+H]+

D: 1-(1-(1-(4-(1,1,1,3,3,3-Hexafluoro-2-hydroxypropan-2-yl)benzyl)piperidin-4-yl)-1H-benzo[d]imidazol-5-yl)-3-(pyridin-4-yl)urea 2-(4-((4-(5-Amino-1H-benzo[d]imidazol-1-yl)piperidin-1-yl)methyl)phenyl)-1,1,1,3,3,3-hexafluoropropan-2-ol (0.212 mmol, 0.1 g) and phenyl pyridin-4-ylcarbamate (0.318 mmol, 0.068 g) were combined and heated in a Reactivial in dioxane (2 mL) for 2 days. The solvent was removed and the resulting residue purified by silica chromatography (eluting with a solvent gradient from dichloromethane to 8% methanol/dichloromethane) to afford the title compound (14 mg). MS (ESI) m/z 593.2 [M+H]+

Example 38

1-(2-(1-(4-(1,1,1,3,3,3-Hexafluoro-2-hydroxypropan-2-yl)benzyl)piperidin-4-yl)-2H-indazol-5-yl)-3-(pyridin-4-yl)urea

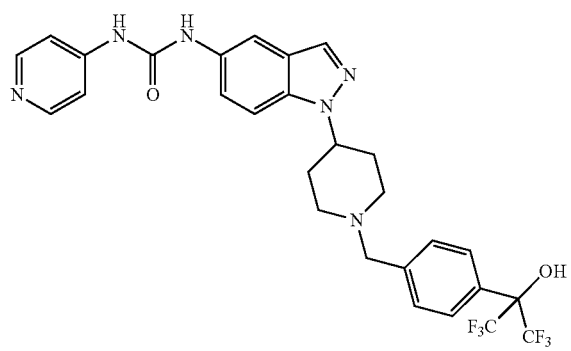 [SMILES: O=C(Nc1ccncc1)Nc1ccc2c(cnn2C2CCN(Cc3ccc(C(O)(C(F)(F)F)C(F)(F)F)cc3)CC2)c1]

A: tert-Butyl 4-(5-nitro-1H-indazol-1-yl)piperidine-1-carboxylate

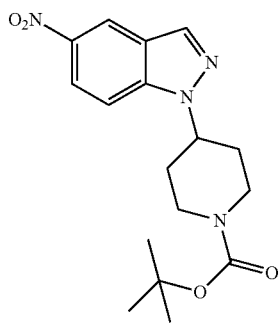

tert-Butyl 4-(methylsulfonyloxy)piperidine-1-carboxylate (30.6 mmol, 8.56 g), potassium carbonate (61.3 mmol, 8.47 g) and 5-nitro-1H-indazole (30.6 mmol, 5 g) were combined and heated to 100° C. in N,N-dimethylformamide (30 mL) for 3 hours. The reaction mixture was diluted with ethyl acetate and washed with water. The organic phase was dried over sodium sulfate and concentrated at reduced pressure. The resulting residue was purified by silica chromatography (eluting with a solvent gradient from dichloromethane to 30% ethyl acetate/heptane to 50% ethyl acetate/heptane) to afford the title compound (2.35 g). MS (ESI) m/z 291.0 [M+H]+

B: tert-Butyl 4-(5-amino-1H-indazol-1-yl)piperidine-1-carboxylate

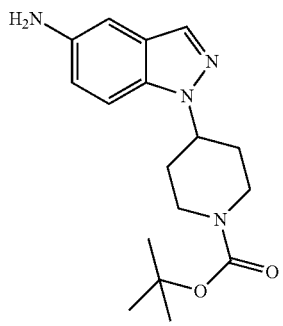 [SMILES: CC(C)(C)OC(=O)N1CCC(n2ncc3cc([N+](=O)[O-])ccc32)CC1]

tert-Butyl 4-(5-nitro-1H-indazol-1-yl)piperidine-1-carboxylate (6.78 mmol, 2.35 g) and 10% palladium on carbon (0.136 mmol, 0.144 g) were combined and stirred in ethanol (50 mL) under 5 bar hydrogen for 1 hour. The reaction mixture was filtered and the filtrate concentrated under vacuum to afford the title compound (2.1 g).

MS (ESI) m/z 317.2 [M+H]+

C: 1-(Piperidin-4-yl)-1H-indazol-6-amine

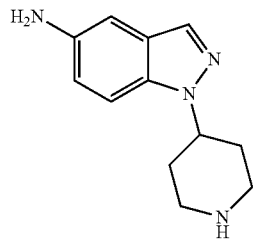 [SMILES: Nc1ccc2c(cnn2C2CCNCC2)c1]

tert-Butyl 4-(6-amino-1H-indazol-1-yl)piperidine-1-carboxylate (6.64 mmol, 2.1 g) was stirred at room temperature in dichloromethane (10 mL)/trifluoroacetic acid (10 mL) for 1 hour. The reaction mixture was concentrated under vacuum. The resulting residue was purified by SCX column to afford the title compound (1.05 g).

MS (ESI) m/z 217.3 [M+H]+

D: 2-(4-((4-(5-Amino-1H-indazol-1-yl)piperidin-1-yl)methyl)phenyl)-1,1,1,3,3,3-hexafluoropropan-2-ol

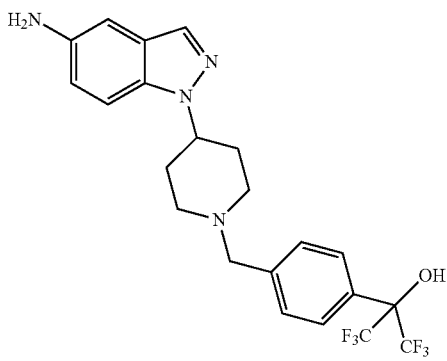 [SMILES: Nc1ccc2c(cnn2C2CCN(Cc3ccc(C(O)(C(F)(F)F)C(F)(F)F)cc3)CC2)c1]

1-(Piperidin-4-yl)-1H-indazol-5-amine (4.85 mmol, 1.05 g), 2-(4-(bromomethyl)phenyl)-1,1,1,3,3,3-hexafluoropropan-2-ol (4.85 mmol, 1.636 g) and potassium carbonate (9.71 mmol, 1.342 g) were combined and stirred in acetonitrile (15 mL) at room temperature for 3 days. The reaction mixture was concentrated under vacuum. The resulting residue was purified by silica chromatography (eluting with a solvent gradient from dichloromethane to 5% methanol/dichloromethane) to afford the title compound (332 mg). MS (ESI) m/z 473.0 [M+H]$^+$

E: 1-(2-(1-(4-(1,1,1,3,3,3-Hexafluoro-2-hydroxypropan-2-yl)benzyl)piperidin-4-yl)-2H-indazol-5-yl)-3-(pyridin-4-yl)urea 2-(4-((4-(5-Amino-2H-indazol-2-yl)piperidin-1-yl)methyl)phenyl)-1,1,1,3,3,3-hexafluoropropan-2-ol (0.212 mmol, 0.1 g) and phenyl pyridin-4-ylcarbamate (0.318 mmol, 0.068 g) were combined and stirred in dioxane (2 mL) at 100° C. in a Reactivial. The solvent was removed and the resulting residue was purified by silica chromatography (eluting with a solvent gradient from dichloromethane to 8% methanol/dichloromethane) to afford the title compound (14 mg).

MS (ESI) m/z 593.2 [M+H]$^+$

Example 39

1-(Cyclopropylmethyl)-3-(1-(1-(4-(1,1,1,3,3,3-hexafluoro-2-hydroxypropan-2-yl)benzyl)piperidin-4-yl)-1H-indazol-6-yl)urea

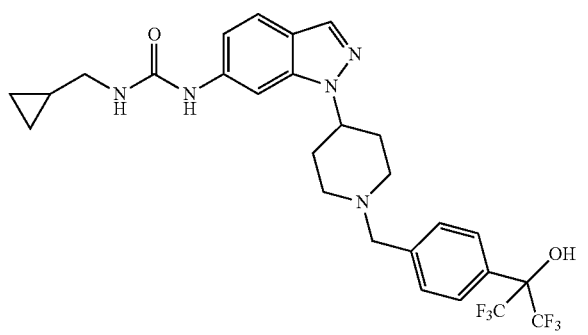 [SMILES: O=C(NCC1CC1)Nc1ccc2cnn(C3CCN(Cc4ccc(C(O)(C(F)(F)F)C(F)(F)F)cc4)CC3)c2c1]

A: tert-Butyl 4-(6-nitro-1H-indazol-1-yl)piperidine-1-carboxylate

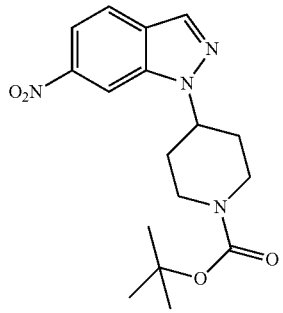

6-Nitro-1H-indazole (12.26 mmol, 2 g), tert-butyl 4-(methylsulfonyloxy)piperidine-1-carboxylate (12.26 mmol, 3.42 g) and potassium carbonate (24.52 mmol, 3.39 g) were combined and heated to 100° C. in N,N-dimethylformamide (40 mL) for 4 hours. The reaction mixture was diluted with ethyl acetate and washed with water. The organic phase was dried over sodium sulfate and concentrated at reduced pressure. The resulting residue was purified by silica chromatography (eluting with a solvent gradient from 20% ethyl acetate/heptane to 60% ethyl acetate/heptane) to afford the title compound (1.045 g). MS (ESI) m/z 347.2 [M+H]$^+$

B: tert-Butyl 4-(6-amino-1H-indazol-1-yl)piperidine-1-carboxylate

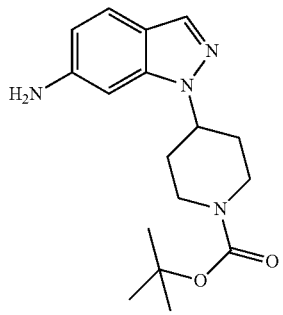 [SMILES: CC(C)(C)OC(=O)N1CCC(n2ncc3ccc([N+](=O)[O-])cc32)CC1]

tert-Butyl 4-(6-nitro-1H-indazol-1-yl)piperidine-1-carboxylate (3.00 mmol, 1.04 g) and palladium (10% on C) (0.150 mmol, 0.160 g) in ethanol (30 mL) were stirred under a hydrogen atmosphere at 5 bar for 1 hour. The reaction mixture was filtered and concentrated at reduced pressure to afford the title compound (1.4 g). MS (ESI) m/z 317.2 [M+H]$^+$

C: 1-(Piperidin-4-yl)-1H-indazol-6-amine

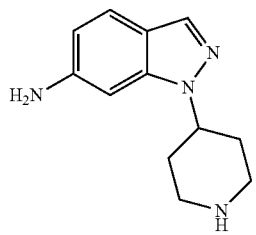 [SMILES: Nc1ccc2cnn(C3CCNCC3)c2c1]

tert-Butyl 4-(6-amino-1H-indazol-1-yl)piperidine-1-carboxylate (4.42 mmol, 1.399 g) and trifluoroacetic acid (5 mL)/dichloromethane (5 mL) were stirred at room temperature for 1 hour. The reaction mixture was concentrated at reduced pressure.

The resulting residue was passed down a SCX column to afford the title compound (77 mg). MS (ESI) m/z 217.4 [M+H]$^+$

D: 2-(4-((4-(6-Amino-1H-indazol-1-yl)piperidin-1-yl)methyl)phenyl)-1,1,1,3,3,3-hexafluoropropan-2-ol

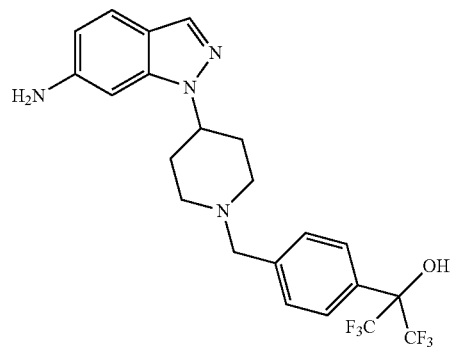 [SMILES: Nc1ccc2cnn(C3CCN(Cc4ccc(C(O)(C(F)(F)F)C(F)(F)F)cc4)CC3)c2c1]

1-(Piperidin-4-yl)-1H-indazol-6-amine (3.33 mmol, 0.721 g), 2-(4-(bromomethyl)phenyl)-1,1,1,3,3,3-hexafluoropropan-2-ol (3.33 mmol, 1.124 g) and potassium carbonate (6.67 mmol, 0.921 g) were combined and stirred overnight at room temperature in acetonitrile (15 mL). The reaction mixture was concentrated at reduced pressure and the resulting residue taken up in dichloromethane. The organic phase was washed with water and dried over sodium sulfate. The solvent was removed and the resulting residue was purified by silica chromatography (eluting with a solvent gradient from dichloromethane to 8% methanol/dichloromethane) to afford the title compound (664 mg). MS (ESI) m/z 473.5 [M+H]$^+$

E: 1-(Cyclopropylmethyl)-3-(1-(1-(4-(1,1,1,3,3,3-hexafluoro-2-hydroxypropan-2-yl)benzyl)piperidin-4-yl)-1H-indazol-6-yl)urea 2-(4-((4-(6-Amino-1H-indazol-1-yl)piperidin-1-yl)methyl)phenyl)-1,1,1,3,3,3-hexafluoropropan-2-ol (0.212 mmol, 0.1 g) and 4-nitrophenyl carbonochloridate (0.212 mmol, 0.043 g) were combined and stirred in dichloromethane (2 mL) for 1 hour. Cyclopropylmethanamine (0.423 mmol, 0.037 mL, 0.030 g) was added and the reaction stirred at room temperature for 2 hours. The organic was washed with water and dried over sodium sulfate. The solvent was removed and the resulting residue was purified by silica chromatography (eluting with a solvent gradient from dichloromethane to 6% methanol/dichloromethane) to afford the title compound (93 mg). MS (ESI) m/z 570.0 [M+H]$^+$

Example 40

1-(Cyclopropylmethyl)-3-(1-(1-(4-(1,1,1,3,3,3-hexafluoro-2-hydroxypropan-2-yl)benzyl)piperidin-4-yl)-1H-indol-6-yl)urea

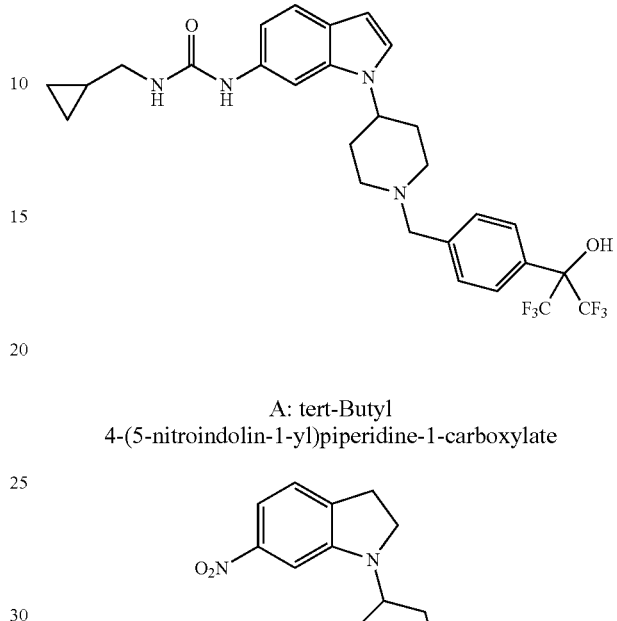

A: tert-Butyl 4-(5-nitroindolin-1-yl)piperidine-1-carboxylate

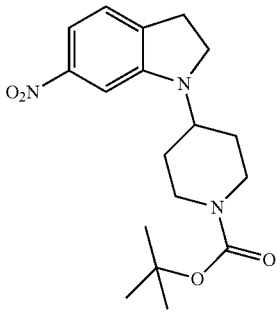 [SMILES: CC(C)(C)OC(=O)N1CCC(N2CCc3ccc([N+](=O)[O-])cc32)CC1]

5-Nitroindoline (12.18 mmol, 2 g) was stirred in acetic acid (50 mL) in an ice bath. tert-Butyl 4-oxopiperidine-1-carboxylate (14.62 mmol, 2.91 g) was added, followed by the portionwise addition of sodium triacetoxyhydroborate (18.27 mmol, 3.87 g). The reaction mixture was stirred for 1 hour at room temperature. The reaction mixture was concentrated at reduced pressure. The resulting residue was taken up in ethyl acetate and washed with saturated sodium bicarbonate solution. The organic phase was concentrated at reduced pressure to afford the title compound (5.2 g).

MS (ESI) m/z 348.1 [M+H]$^+$

B: tert-Butyl 4-(5-nitro-1H-indol-1-yl)piperidine-1-carboxylate

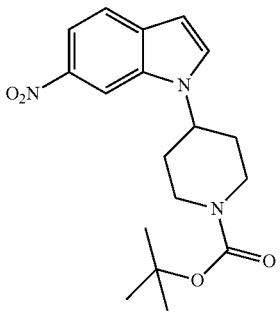 [SMILES: CC(C)(C)OC(=O)N1CCC(n2ccc3ccc([N+](=O)[O-])cc32)CC1]

tert-Butyl 4-(5-nitroindolin-1-yl)piperidine-1-carboxylate (9.72 mmol, 3.377 g) was stirred at 0° C. in tetrahydrofuran (25 mL). 2,3-Dichloro-5,6-dicyano-1,4-benzoquinone (10.69 mmol, 2.427 g) in tetrahydrofuran was added dropwise. The reaction was stirred at <10° C. for 1 hour. The reaction was stirred for 2 hours at room temperature. Ethyl acetate was added and the reaction washed with saturated sodium bicarbonate solution. The mixture was passed through a celite plug before being separated. The organic phase was concentrated at reduced pressure to afford the title compound (3.123 g). MS (ESI) m/z 290.3 [M-Boc+H]$^+$ C: tert-Butyl 4-(5-amino-1H-indol-1-yl)piperidine-1-carboxylate

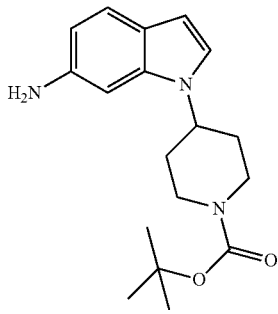

tert-Butyl 4-(5-nitro-1H-indol-1-yl)piperidine-1-carboxylate (9.04 mmol, 3.123 g) and 10% palladium on carbon (0.452 mmol, 0.481 g) were combined and stirred under a hydrogen atmosphere at 5 bar at room temperature in ethanol (25 mL) for 1 hour. The reaction mixture was filtered and concentrated at reduced pressure to afford the title compound. (2.506 g). MS (ESI) m/z 316.1 [M+H]$^+$ D: 1-(Piperidin-4-yl)-1H-indol-5-amine

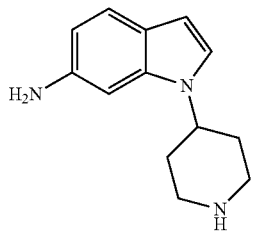 [SMILES: Nc1ccc2ccn(C3CCNCC3)c2c1]

tert-Butyl 4-(5-amino-1H-indol-1-yl)piperidine-1-carboxylate (7.95 mmol, 2.506 g) was stirred in tetrahydrofuran (10 mL)/trifluoroacetic acid (10 mL) at room temperature for 1 hour. The solvent was removed at reduced pressure. The resulting residue was passed down an SCX column to afford the title compound (660 mg).

MS (ESI) m/z 216.8 [M+H]$^+$

E: 2-(4-((4-(5-Amino-1H-indol-1-yl)piperidin-1-yl)methyl)phenyl)-1,1,1,3,3,3-hexafluoropropan-2-ol

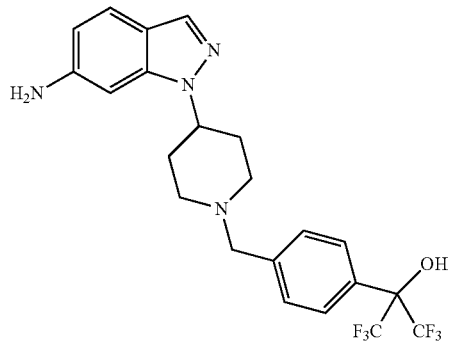 [SMILES: Nc1ccc2cnn(C3CCN(Cc4ccc(C(O)(C(F)(F)F)C(F)(F)F)cc4)CC3)c2c1]

2-(4-(Bromomethyl)phenyl)-1,1,1,3,3,3-hexafluoropropan-2-ol (3.07 mmol, 1.033 g), 1-(piperidin-4-yl)-1H-indol-5-amine (3.07 mmol, 0.66 g) and potassium carbonate (9.20 mmol, 1.271 g) were combined in acetonitrile (20 mL) and stirred at room temperature overnight. The reaction mixture was concentrated at reduced pressure. The resulting residue was taken up in dichloromethane and washed with water. The organic phase was dried over sodium sulfate and concentrated at reduced pressure. The solvent was removed and the resulting residue was purified by silica chromatography (eluting with a solvent gradient from dichloromethane to 3% methanol/dichloromethane) to afford the title compound (332 mg). MS (ESI) m/z 472.9 [M+H]$^+$ F: 1-(Cyclopropylmethyl)-3-(1-(1-(4-(1,1,1,3,3,3-hexafluoro-2-hydroxypropan-2-yl)benzyl)piperidin-4-yl)-1H-indol-6-yl)urea 2-(4-((4-(6-Amino-1H-indol-1-yl)piperidin-1-yl)methyl)phenyl)-1,1,1,3,3,3-hexafluoropropan-2-ol (0.350 mmol, 0.165 g) and 4-nitrophenyl carbonochloridate (0.350 mmol, 0.071 g) were combined and stirred in tetrahydrofuran (2 mL) for 1 hour. Cyclopropylmethanamine (0.700 mmol, 0.061 mL, 0.050 g) was added and the reaction stirred at room temperature for 2 hours. The organic phase was washed with water and dried over sodium sulfate. The solvent was removed and the resulting residue was purified by silica chromatography (eluting with a solvent gradient from dichloromethane to 3% methanol/dichloromethane) to afford the title compound (24 mg). MS (ESI) m/z 569.2 [M+H]$^+$ Example 41

Radioligand Competition Binding Scintillation Proximity Assay (SpA) Using Recombinant Human LXRα or LXRβ Protein These assays are used to evaluate the potency of compounds in their ability to compete with the binding of the agonist radioligand [$^3$H]T0901317. These assays utilise the purified ligand binding domain (LBD) of Liver X Receptor alpha (LXRα) or Liver X Receptor beta (LXRβ) fused to glutathione-5-transferase (GST) tagged protein (LXRα-LBD-GST and LXRβ-LBD-GST respectively) and scintillation proximity assay (SpA) technology to determine binding affinities (pKi) of compounds at the ligand binding domain (LBD) of the human nuclear hormone receptor LXRα or LXRβ.

Preparation of Recombinant Human LXRα and LXRβ

Human LXRα and LXRβ were expressed as GST-fusion proteins in *E. coli*.

The LBD of LXRα or LXRβ was amplified by PCR and sub-cloned into the prokaryotic expression vector pGEX-4T-1 (GE Healthcare). Expression of LXRα or LXRβ from the pGEX-4T-1 plasmid in *E. Coli* resulted in the production of the recombinant glutathione-5-transferase (GST) LXRα-LBD or LXRβ-LBD fusion proteins. *E. coli*, containing either the LXRα or LXRβ pGEX-4T-1 plasmid, were propagated, induced, and harvested by centrifugation. The bacterial pellets were resuspended in lysis buffer containing 50 mM tris (Hydroxymethyl)aminomethane (TRIS)-pH 8.0, 100 mM Sodium Chloride (NaCl), 1 mM ethylenediaminetetraacetic acid (EDTA) and one tablet of Proteinase inhibitor cocktail complete/EDTA free (Roche) (per 50 mL of buffer). The mixtures were sonicated on ice with a Branson sonifier. The suspensions were centrifuged and dithiothreitol (DTT) added to the supernatants to obtain a final concentration of 25 mM. Recombinant human LXRα-LBD-GST or LXRβ-LBD-GST proteins were purified from the resulting supernatants by affinity chromatography on Glutathione-Sepharose Fast flow (Amersham), and the proteins eluted with buffer containing glutathione (50 mM tris pH 8.0, 2 mM DTT, 10 mM glutathione). Proteins were stored in 20 mM N2-hydroxyethylpiperazine-N'-2-ethanesulfonic acid (HEPES), 2 mM DTT with 10% glycerol at −80° C.

Binding to LXRα or LXRβ LBDs

For LXRα or LXRβ assays, an aliquot of recombinant human LXRα-LBD-GST or LXRβ-LBD-GST protein was diluted to 0.5 µg/mL and incubated in a final volume of 100 µL SpA buffer (10 mM potassium hydrogen phosphate anhydrous [$K_2HPO_4$], 10 mM potassium Phosphate Monobasic [$KH_2PO_4$], 2 mM EDTA pH 7.1, 50 mM NaCl, 1 mM DTT, 2 mM 3-[(3-cholamidopropyl)dimethylammonio]-1-propanesulfonate (CHAPS)) containing Protein-A coupled scintillant filled YtSi SpA beads (GE Healthcare), to a final concentration of 1 mg/mL and Goat anti-GST antibody (GE Healthcare) to a final concentration of 5 µg/mL. T0901317 ($K_d$=10 nM) was used as a reference in each assay. To the assay mixture, 50 nM [$^3$H]T0901317 (50 Ci/mmol), ±test compound was added and the mixture incubated at 15° C. on a plate shaker for 2 hours. Test compounds were assayed over a concentration range. After incubation, the assay plates were read on a Packard TopCount. The pKi value for T0901317 in LXRα and LXRβ binding assays is: pKi=8.4±0.2. T0901317 at a concentration of 5 µM was used as the maximum binding control. Compounds of the invention show pKi values >5.0 or show >50% activity at 10 µM at LXRα and/or LXRβ and preferred compounds show pKi values of >7 at LXRα and/or LXRβ using these assay protocols. Table I shows the LXRβ pKi values for a number of the preferred compounds of the invention.

TABLE 1

| Ex. | Chemical name | Chemical structure | LXRβ pKi |
|---|---|---|---|
| 1C | 1-(4-(1-(4-(1,1,1,3,3,3-hexa-fluoro-2-hydroxy-propan-2-yl)benzyl)piperidin-4-yloxy)-phenyl)-3-(tetrahydro-2H-pyran-4-yl)urea | 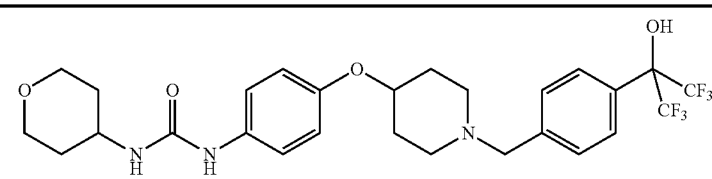 | 8.01 |
| 1D | 1-(4-(1-(4-(1,1,1,3,3,3-hexa-fluoro-2-hydroxy-propan-2-yl)benzyl)piperidin-4-yloxy)-phenyl)-3-(2-hydroxy-2-methyl-propyl)urea | 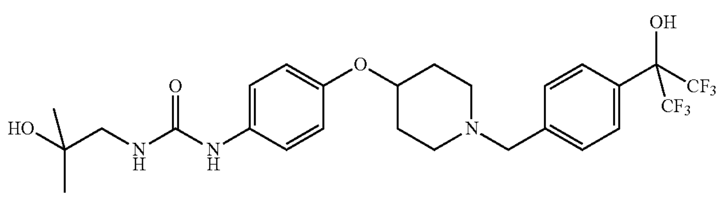 [SMILES: CC(C)(O)CNC(=O)Nc1ccc(OC2CCN(Cc3ccc(C(O)(C(F)(F)F)C(F)(F)F)cc3)CC2)cc1] | 7.94 |
| 1F | 1-(4-(1-(4-(1,1,1,3,3,3-hexa-fluoro-2-hydroxy-propan-2-yl)benzyl)piperidin-4-yloxy)-phenyl)-3-(pyrazin-4-yl)urea | 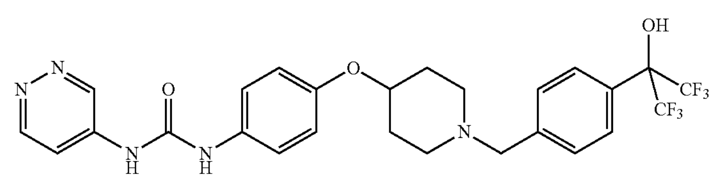 [SMILES: O=C(Nc1ccc(OC2CCN(Cc3ccc(C(O)(C(F)(F)F)C(F)(F)F)cc3)CC2)cc1)Nc1ccnnc1] | 8.23 |
| 2 | 1-(4-(1-(4-(1,1,1,3,3,3-hexa-fluoro-2-hydroxy-propan-2-yl)benzyl)piperidin-4-yloxy)-phenyl)-3-(pyridin-4-yl)urea | 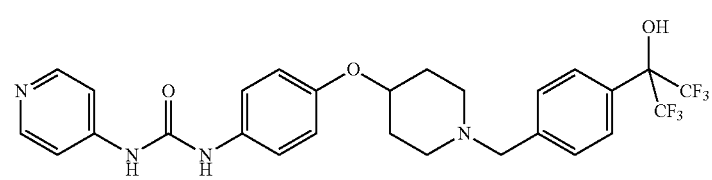 [SMILES: O=C(Nc1ccncc1)Nc1ccc(OC2CCN(Cc3ccc(C(O)(C(F)(F)F)C(F)(F)F)cc3)CC2)cc1] | 8.69 |
| 2C | 1-(3-fluoropyridin-4-yl)-3-(4-(1-(4-(1,1,1,3,3,3-hexafluoro-2-hydroxy-propan-2-yl)benzyl)-piperidin-4-yloxy)phenyl)urea | 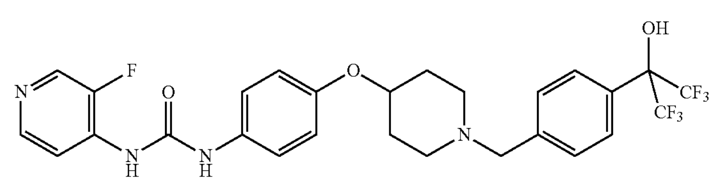 [SMILES: O=C(Nc1ccc(OC2CCN(Cc3ccc(C(O)(C(F)(F)F)C(F)(F)F)cc3)CC2)cc1)Nc1ccncc1F] | 8.70 |

TABLE 1-continued

| Ex. | Chemical name | Chemical structure | LXRβ pKi |
|---|---|---|---|
| 2E | 1-(4-(1-(4-(1,1,1,3,3,3-hexa-fluoro-2-hydroxy-propan-2-yl)-benzyl)piperidin-4-yloxy)-phenyl)-3-(pyrimidin-4-yl)urea | 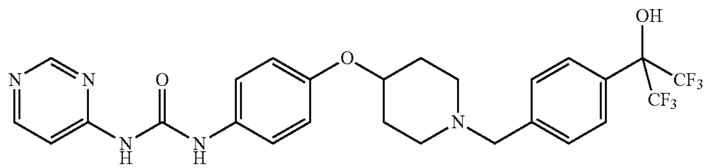 [SMILES: O=C(Nc1ccc(OC2CCN(Cc3ccc(C(O)(C(F)(F)F)C(F)(F)F)cc3)CC2)cc1)Nc1ccncn1] | 8.52 |
| 6P | 1-(4-((1-(4-(1,1,1,3,3,3-hexa-fluoro-2-hydroxy-propan-2-yl)-benzyl)piperidin-4-yl)methyl)-phenyl)-3-(oxetan-3-yl)urea | 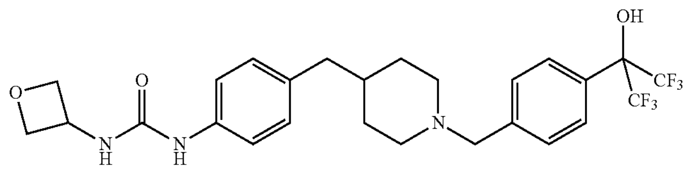 [SMILES: O=C(Nc1ccc(CC2CCN(Cc3ccc(C(O)(C(F)(F)F)C(F)(F)F)cc3)CC2)cc1)NC1COC1] | 8.04 |
| 6S | 1-(3-fluoropyridin-4-yl)-3-(4-((1-(4-(1,1,1,3,3,3-hexafluoro-2-hydroxypropan-2-yl)benzyl)-piperidin-4-yl)methyl)phenyl)-urea | 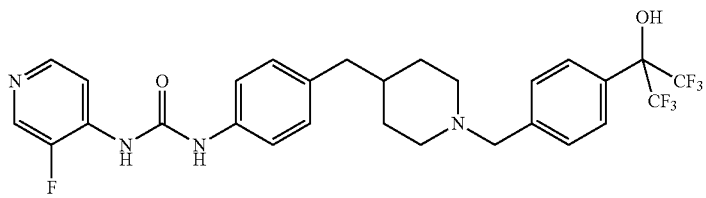 [SMILES: O=C(Nc1ccc(CC2CCN(Cc3ccc(C(O)(C(F)(F)F)C(F)(F)F)cc3)CC2)cc1)Nc1ccncc1F] | 8.13 |
| 7 | 1-(4-((1-(4-(1,1,1,3,3,3-hexa-fluoro-2-hydroxy-propan-2-yl)-benzyl)piperidin-4-yl)methyl)-phenyl)-3-(pyridin-4-yl)urea | 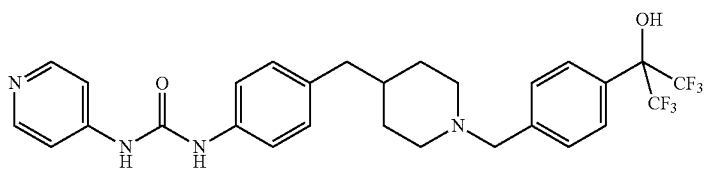 [SMILES: O=C(Nc1ccncc1)Nc1ccc(CC2CCN(Cc3ccc(C(O)(C(F)(F)F)C(F)(F)F)cc3)CC2)cc1] | 8.10 |
| 7B | 1-(4-((1-(4-(1,1,1,3,3,3-hexa-fluoro-2-hydroxy-propan-2-yl)benzyl)piperidin-4-yl)-methyl)phenyl)-3-(pyrimidin-4-yl)urea | 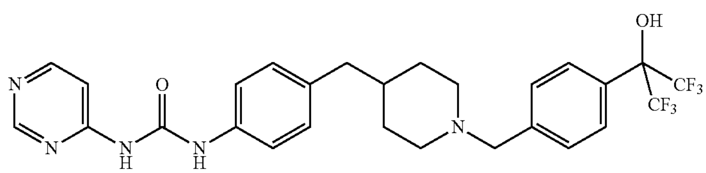 [SMILES: O=C(Nc1ccc(CC2CCN(Cc3ccc(C(O)(C(F)(F)F)C(F)(F)F)cc3)CC2)cc1)Nc1ccncn1] | 8.37 |
| 12D | 1-(2-(fluoro-4-((1-(4-(1,1,1,3,3,3-hexafluoro-2-hydroxypropan-2-yl)benzyl)piperidin-4-yl)methyl)phenyl)-3-(isoxazol-4-yl)urea | 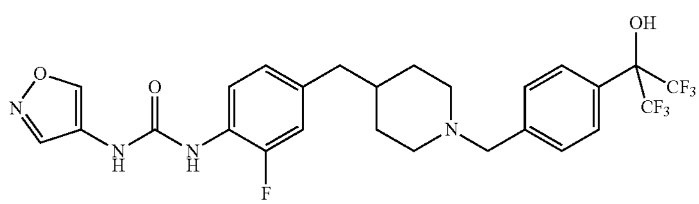 [SMILES: O=C(Nc1cnoc1)Nc1ccc(CC2CCN(Cc3ccc(C(O)(C(F)(F)F)C(F)(F)F)cc3)CC2)cc1F] | 8.31 |
| 12E | 1-(2-fluoro-4-((1-(4-(1,1,1,3,3,3-hexafluoro-2-hydroxy-propan-2-yl)benzyl)piperidin-4-yl)methyl)phenyl)-3-(5-methyl-isoxazol-3-yl)urea | 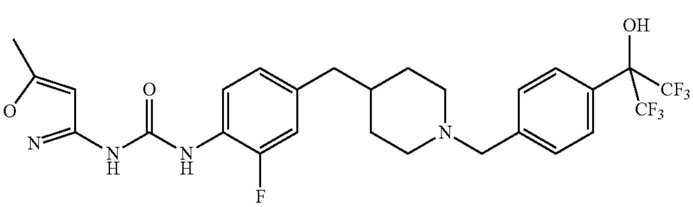 [SMILES: C/C(O)=C/C(=N)NC(=O)Nc1ccc(CC2CCN(Cc3ccc(C(O)(C(F)(F)F)C(F)(F)F)cc3)CC2)cc1F] | 8.02 |
| 12F | (S)-1-(2-fluoro-4-((1-(4-(1,1,1-3,3,3-hexafluoro-2-hydroxy-propan-2-yl)benzyl)piperidin-4-yl)methyl)phenyl)-3-(tetra-hydrofuran-3-yl)urea | 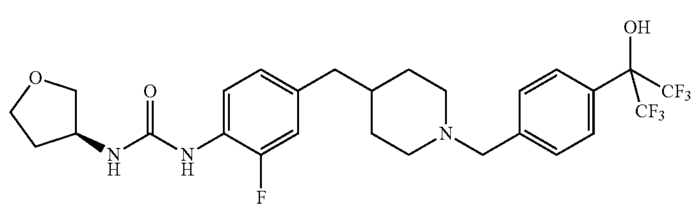 [SMILES: O=C(Nc1ccc(CC2CCN(Cc3ccc(C(O)(C(F)(F)F)C(F)(F)F)cc3)CC2)cc1F)N[C@H]1CCOC1] | 7.77 |

TABLE 1-continued

| Ex. | Chemical name | Chemical structure | LXRβ pKi |
|---|---|---|---|
| 12I | 1-(2-fluoro-4-((1-(4-(1,1,1,3,3,3-hexafluoro-2-hydroxy-propan-2-yl)benzyl)piperidin-4-yl)methyl)phenyl)-3-(3,3,3-trifluoro-2-hydroxy-propyl)urea | 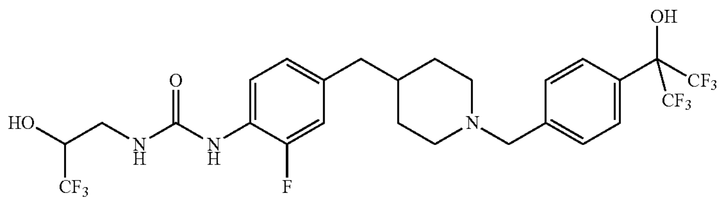 [SMILES: O=C(NCC(O)C(F)(F)F)Nc1ccc(CC2CCN(Cc3ccc(C(O)(C(F)(F)F)C(F)(F)F)cc3)CC2)cc1F] | 8.56 |
| 12AA | 1-(2-fluoro-4-((1-(4-(1,1,1,3,3,3-hexafluoro-2-hydroxypropan-2-yl)benzyl)piperidin-4-yl)methyl)phenyl)-3-(3,3,3-trifluoro-2-hydroxy-2-methyl-propyl)urea | 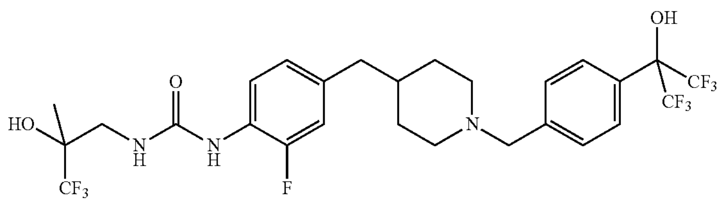 [SMILES: CC(O)(CNC(=O)Nc1ccc(CC2CCN(Cc3ccc(C(O)(C(F)(F)F)C(F)(F)F)cc3)CC2)cc1F)C(F)(F)F] | 8.24 |
| 12AC | 1-(2-fluoro-4-((1-(4-(1,1,1,3,3,3-hexafluoro-2-hydroxypropan-2-yl)benzyl)piperidin-4-yl)methyl)phenyl)-3-(2-hydroxy-2-methylpropyl)urea | 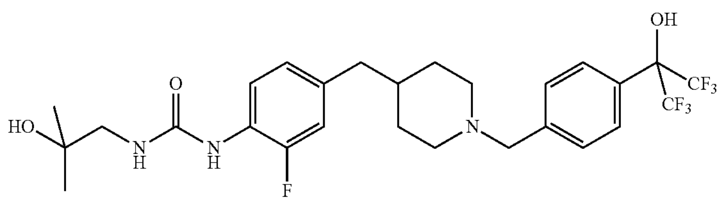 [SMILES: CC(C)(O)CNC(=O)Nc1ccc(CC2CCN(Cc3ccc(C(O)(C(F)(F)F)C(F)(F)F)cc3)CC2)cc1F] | 7.77 |
| 12AE | 1-(2-fluoro-4-((1-(4-(1,1,1,3,3,3-hexafluoro-2-hydroxypropan-2-yl)benzyl)piperidin-4-yl)methyl)phenyl)-3-(oxetan-3-yl)-urea | 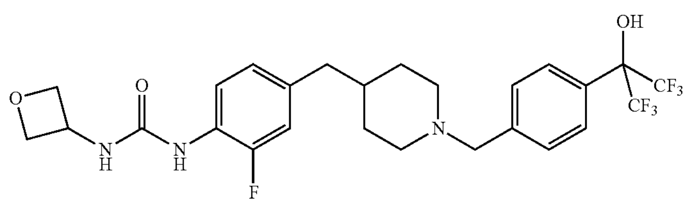 [SMILES: O=C(Nc1ccc(CC2CCN(Cc3ccc(C(O)(C(F)(F)F)C(F)(F)F)cc3)CC2)cc1F)NC1COC1] | 7.66 |
| 12AG | 1-(2-fluoro-4-((1-(4-(1,1,1,3,3,3-hexafluoro-2-hydroxypropan-2-yl)benzyl)piperidin-4-yl)methyl)phenyl)-3-(tetrahydro-2H-pyran-4-yl)urea | 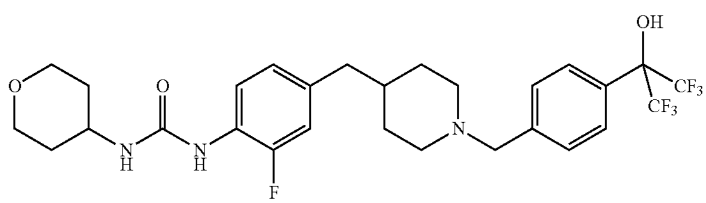 [SMILES: O=C(Nc1ccc(CC2CCN(Cc3ccc(C(O)(C(F)(F)F)C(F)(F)F)cc3)CC2)cc1F)NC1CCOCC1] | 7.66 |
| 13 | 1-(2-fluoro-4-((1-(4-(1,1,1,3,3,3-hexafluoro-2-hydroxypropan-2-yl)benzyl)piperidin-4-yl)methylphenyl)-3-(pyridin-4-yl)urea | 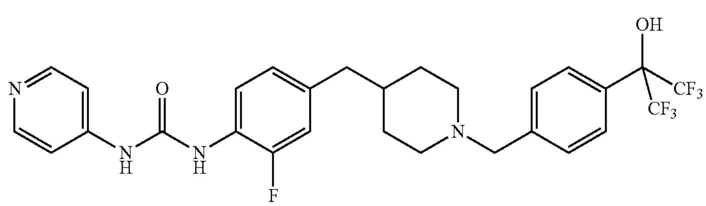 [SMILES: O=C(Nc1ccncc1)Nc1ccc(CC2CCN(Cc3ccc(C(O)(C(F)(F)F)C(F)(F)F)cc3)CC2)cc1F] | 8.26 |
| 13B | 1-(2-fluoro-4-((1-(4-(1,1,1,3,3,3-hexafluoro-2-hydroxypropan-2-yl)benzyl)piperidin-4-yl)methyl)phenyl)-3-(pyrimidin-4-yl)urea | 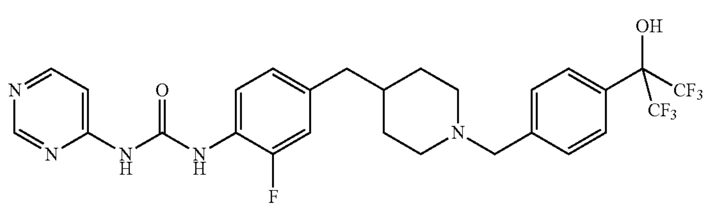 [SMILES: O=C(Nc1ccncn1)Nc1ccc(CC2CCN(Cc3ccc(C(O)(C(F)(F)F)C(F)(F)F)cc3)CC2)cc1F] | 8.01 |

TABLE 1-continued

| Ex. | Chemical name | Chemical structure | LXRβ pKi |
|---|---|---|---|
| 16 | 1-(2,5-difluoro-4-((1-(4-(1,1,1,3,3,3-hexafluoro-2-hydroxy-propan-2-yl)benzyl)piperidin-4-yl)methyl)phenyl)-3-(2-hydroxy-2-methylpropyl)urea | 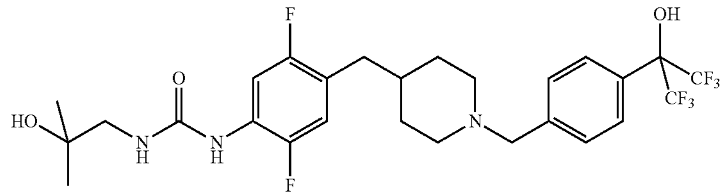 [SMILES: CC(C)(O)CNC(=O)Nc1cc(F)c(CC2CCN(Cc3ccc(C(O)(C(F)(F)F)C(F)(F)F)cc3)CC2)cc1F] | 7.61 |
| 16B | 1-(2,5-difluoro-4-((1-(4-(1,1,13,3,3-hexafluoro-2-hydroxy-propan-2-yl)benzyl)piperidin-4-yl)methyl)phenyl)-3-(3,3,3-trifluoro-2-hydroxy-2-methyl-propyl)urea | 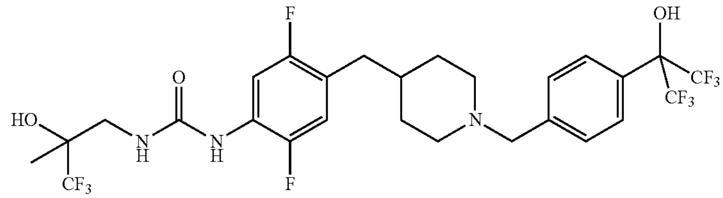 [SMILES: CC(O)(CNC(=O)Nc1cc(F)c(CC2CCN(Cc3ccc(C(O)(C(F)(F)F)C(F)(F)F)cc3)CC2)cc1F)C(F)(F)F] | 8.10 |
| 17 | 1-(2-chloro-4-((1-(4-(1,1,1,3,3,3-hexafluoro-2-hydroxy-propan-2-yl)benzyl)piperidin-4-yl)methyl)phenyl)-3-(2-hydroxy-2-methyl-propyl)urea | 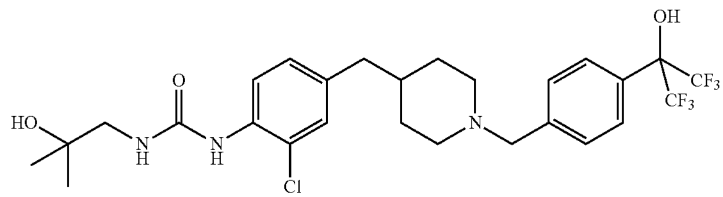 [SMILES: CC(C)(O)CNC(=O)Nc1ccc(CC2CCN(Cc3ccc(C(O)(C(F)(F)F)C(F)(F)F)cc3)CC2)cc1Cl] | 8.22 |

LXRα and LXRβ Transactivation assays

Intracellular agonist activity at LXRα and LXRβ was measured in vitro using recombinant chinese hamster ovary K1 (CHO.K1) cells stably expressing a natural estrogen responsive element (ERE)-containing luciferase reporter construct and either the human Estrogen receptor α (ERα)/LXRα or ERα/LXRβ chimeric receptor protein respectively from a eukaryotic expression construct. The ERα/LXRα and ERα/LXRβ chimeric receptor proteins contain the human LXRα or human LXRβ receptor LBD fused to the human ERα receptor DNA binding domain (DBD). In these assays compounds that can bind to the LBD of the human LXRα or LXRβ receptor, are able to activate the chimeric receptor protein intracellularly. Following activation, the ERα DBD can induce ERE-mediated luciferase expression via the natural ERE present in the rat oxytocin promoter luciferase construct (pROLUC). Using this system LXRα and LXRβ agonist-induced luciferase assays were generated using T0901317 as the agonist control.

Constructs

Expression constructs were prepared by inserting the ligand binding domain (LBD) of human LXRα or human LXRβ cDNA adjacent to the human ERα transcription factor DNA binding domain (DBD) to create pNGV1.ERαDBD-LXRαLBD and pNGV1.ERαDBD-LXRβLBD. The pNGV1 mammalian expression construct (EMBL nucleotide sequence database file ASPNGV1, acc. # X99274) carries a selection marker for Neomycin (G418). The ERα responsive element of the rat oxytocin promoter (RO) was used to generate the promoter construct, pROLUC which contains several copies of the ERα response element (ERE) placed adjacent to the luciferase reporter gene. Construction of the promoter construct was based on the RO promoter region (position −363/+16) excised as a HindIII/MboI restriction enzyme fragment and linked to the firefly luciferase encoding sequence (Ivell and Richter, Proc Natl Acad Sci USA. 7: 2006-2010 (1984)). Stable CHO.K1 cell lines expressing pNGV1.ERαDBD-LXRαLBD or pNGV1.ERαDBD-LXRβLBD in combination with pROLUC were generated following transfection and selection of positive expressing clones using Neomycin. The best cell lines (CHO.K1 LXRα and CHO.K1 LXRβ) were selected on the basis of agonist window in response to 3 μM T0901317 and stability of response up to 20 passages.

Assay of Agonist Activity of Test Compounds in LXRα and LXRβ Transactivation Assays For LXRα and LXRβ transactivation assays CHO.K1 LXRα or CHO.K1 LXRβ cells respectively were seeded at a density of 25000 cells/well in 96 well plates in 200 μL of Dulbecco's Modified Eagle Medium (phenol red free) containing 5% charcoal treated bovine calf serum at 37° C. in a humidified atmosphere of 5% $CO_2$. After 6 hours post-seeding, compounds were characterised by incubation with cells for 16 hours across a concentration range. T0901317 at a concentration of 3 μM was used as the maximum agonist control in each assay. Luciferase activity was determined using a Luciferase assay kit (Perkin Elmer). Determination of luciferase activity was initiated by addition of lysis buffer to each well and light emission measured using a Packard Topcount reader. The $pEC_{50}$ values for T0901317 in the LXRα and LXRβ transactivation assays are: $pEC_{50}$=7.3±0.2 and 7.4±0.2 respectively. Agonist activities of test compounds were compared against the maximum agonist control. Selected compounds of the invention were shown to have LXRα and/or LXRβ agonist activity using these assay protocols.

The invention claimed is:

1. A (1,1,1,3,3,3-hexafluoro-2-hydroxypropan-2-yl)phenyl derivative having the general Formula I Formula I

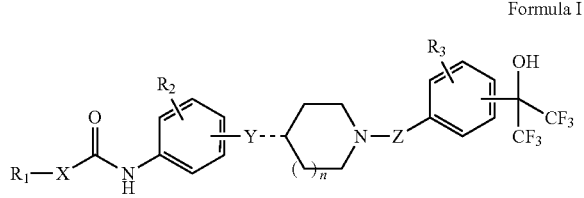

wherein
n is 1;
X is $NR_4$;
Y is O and the dotted bond represents a single bond; or
Y has a meta or para substitution pattern on the phenyl ring in relation to the phenyl-NH position;
Z is $CH_2$;
the hexafluoroispopropanol substituent has an ortho, meta or para substitution pattern on the phenyl ring in relation to the phenyl-Z position;
$R_1$ is a 4-, 5- 6-membered saturated or unsaturated heterocycle ring, comprising 1 or 2 heteroatoms selected from $NR_{10}$, O, S, SO and $SO_2$, the ring being optionally substituted by $(C_{1-3})$alkyl, hydroxy, oxo, $NR_{11}R_{12}$ or $R_9OCO$, and the ring being optionally linked to X via a $(C_{1-3})$alkylene group which is optionally substituted by hydroxy; or
when X is $NR_4$, $R_1$ may together with $R_4$ and the N to which they are bonded form a 4-8 membered ring, which can be optionally substituted with hydroxyl or hydroxymethyl;
$R_2$ is H or 1-3 halogens; or
$R_3$ is H or $(C_{1-3})$alkyl;
$R_4$, when present, is H or $(C_{1-3})$alkyl;
$R_9$, when present, is H or $(C_{1-3})$alkyl;
$R_{10}$, when present, is H or $(C_{1-3})$alkyl;
$R_{11}$ and $R_{12}$, when present, are independently H or $(C_{1-3})$alkyl;
or a pharmaceutically acceptable salt thereof.

2. The (1,1,1,3,3,3-hexafluoro-2-hydroxypropan-2-yl) phenyl derivative of claim 1, or a pharmaceutically acceptable salt thereof, wherein X is NH.

3. The (1,1,1,3,3,3-hexafluoro-2-hydroxypropan-2-yl) phenyl derivative of claim 2, or a pharmaceutically acceptable salt thereof, wherein $R_3$ is H and the hexaflouroisopropanol substituent has the para substitution pattern on the phenyl ring in relation to the phenyl-Z position.

4. The (1,1,1,3,3,3-hexafluoro-2-hydroxypropan-2-yl) phenyl derivative of claim 3, or a pharmaceutically acceptable salt thereof, wherein $R_2$ represents H or 1 or 2 halogens selected from F and Cl.

5. The (1,1,1,3,3,3-hexafluoro-2-hydroxypropan-2-yl) phenyl derivative of claim 1 which is selected from the group consisting of:
1-(4-(1-(4-(1,1,1,3,3,3-Hexafluoro-2-hydroxypropan-2-yl)benzyl)piperidin-4-yloxy)phenyl)-3-(tetrahydro-2H-pyran-4-yl)urea;
1-(4-(1-(4-(1,1,1,3,3,3-Hexafluoro-2-hydroxypropan-2-yl)benzyl)piperidin-4-yloxy)phenyl)-3-(pyridazin-4-yl)urea;
1(3-fluoropyridin-4-yl)-3-(4-(1-(4-(1,1,1,3,3,3-hexafluoro-2-hydroxypropan-2-yl)benzyl)piperidin-4-yloxy)phenyl)urea; and
1-(4-(1-(4-(1,1,1,3,3,3-Hexafluoro-2-hydroxypropan-2-yl)benzyl)piperidin-4-yloxy)phenyl)-3-(pyridin-4-yl)urea;
or a pharmaceutically acceptable salt thereof.

6. A pharmaceutical composition comprising a (1,1,1,3,3,3-hexafluoro-2-hydroxypropan-2-yl)phenyl derivative of claim 1 and pharmaceutically acceptable auxiliaries.

7. A method of treating a disorder associated with cholesterol and bile acids transport and metabolism selected from hypercholesterolemia, cholesterol gallstones, a lipid storage disease, diabetes or obesity in a patient comprising administering a therapeutically effective amount of a compound of claim 1 or a pharmaceutically acceptable salt thereof.

* * * * *